(12) United States Patent
Kosmides et al.

(10) Patent No.: US 11,986,538 B2
(45) Date of Patent: May 21, 2024

(54) IMMUNOSWITCH NANOPARTICLES FOR REPROGRAMMED T CELL RESPONSES

(71) Applicant: The Johns Hopkins University, Baltimore, MD (US)

(72) Inventors: Alyssa K. Kosmides, Balitmore, MD (US); Jonathan P. Schneck, Silver Spring, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 17/557,886

(22) Filed: Dec. 21, 2021

(65) Prior Publication Data
US 2022/0111069 A1    Apr. 14, 2022

Related U.S. Application Data

(63) Continuation of application No. 16/327,508, filed as application No. PCT/US2017/048196 on Aug. 23, 2017, now abandoned.

(60) Provisional application No. 62/515,810, filed on Jun. 6, 2017, provisional application No. 62/378,406, filed on Aug. 23, 2016.

(51) Int. Cl.
| | |
|---|---|
| *A61K 47/00* | (2006.01) |
| *A61K 9/00* | (2006.01) |
| *A61K 9/51* | (2006.01) |
| *A61K 39/395* | (2006.01) |
| *A61K 47/68* | (2017.01) |
| *A61K 47/69* | (2017.01) |
| *A61P 35/00* | (2006.01) |
| *C07K 16/28* | (2006.01) |
| *C12N 5/0783* | (2010.01) |
| *A61K 39/00* | (2006.01) |

(52) U.S. Cl.
CPC ........ *A61K 47/6939* (2017.08); *A61K 9/0009* (2013.01); *A61K 9/0019* (2013.01); *A61K 9/5161* (2013.01); *A61K 39/395* (2013.01); *A61K 39/3955* (2013.01); *A61K 47/6849* (2017.08); *A61K 47/6873* (2017.08); *A61P 35/00* (2018.01); *C07K 16/2827* (2013.01); *C07K 16/2878* (2013.01); *C12N 5/0638* (2013.01); *A61K 2039/507* (2013.01); *C07K 2317/75* (2013.01); *C07K 2317/76* (2013.01)

(58) Field of Classification Search
None
See application file for complete search history.

(56) References Cited

U.S. PATENT DOCUMENTS

| | | |
|---|---|---|
| 2009/0175885 A1 | 7/2009 | Wang et al. |
| 2015/0190506 A1 | 7/2015 | Cheung et al. |
| 2015/0344525 A1 | 12/2015 | Luo et al. |
| 2016/0145350 A1* | 5/2016 | Lonberg ........... A61K 39/39558 435/69.6 |

FOREIGN PATENT DOCUMENTS

| | | |
|---|---|---|
| WO | WO 2011/038031 | 3/2011 |
| WO | WO 2016/034085 | 3/2016 |

OTHER PUBLICATIONS

Dai et al. Curing Mice with Large Tumors by Locally Delivering Combinations of Immunomodulatory Antibodies. Clin Cancer Res; 2014, 21(5); 1127-38.*
Kosmides et al. Journal for ImmunoTherapy of Cancer 2014 2(Suppl 3):P108),.*
Ahmad et al., Escape from immunotherapy: Possible mechanisms that influence tumor regression/progression. Cancer Immunol Immunother. Oct. 2004;53(10):844-54.
Arruebo et al., Antibody-Conjugated Nanoparticles for Biomedical Applications. Journal of Nanomaterials. 2009;Article ID 439389, 24 pages.
Ascierto et al., 2015: The Year of Anti-PD-1/PDL1s Against Melanoma and Beyond. EBioMedicine. Jan. 19, 2015;2(2):92-3.
Barrett et al., Chimeric Antigen Receptor Therapy for Cancer. Annu Rev Med. 2014;65:333-47.
Barthkowiak et al., 4-1BB Agonists: Multi-Potent Potentiators of Tumor Immunity. Front Oncol. Jun. 8, 2015;5:117.
Beyersdorf et al., Superagonistic anti-CD28 antibodies: potent activators of regulatory T cells for the therapy of autoimmune diseases. Ann Rheum Dis. Nov. 2005;64 Suppl 4(Suppl 4):iv91-5.
Black et al., Apoptosis-Regulated Low-Avidity Cancer-Specific CD8+ T Cells Can Be Rescued to Eliminate HER2/neu-Expressing Tumors by Costimulatory Agonists in Tolerized Mice. Cancer Immunol Res. Apr. 2014;2(4):307-19.
Bono et al., CD73 and CD39 ectonucleotidases in T cell differentiation: Beyond immunosuppression. FEBS Lett. Nov. 14, 2015;589(22):3454.

(Continued)

*Primary Examiner* — Nianxiang Zou
(74) *Attorney, Agent, or Firm* — Casimir Jones, S.C.; Thomas A. Isenbarger

(57) ABSTRACT

The presently disclosed subject matter relates to immunoswitch particles that switch off immunosuppressive pathways on tumor cells or immunosuppressive molecules induced by tumor cells in the tumor microenvironment, or virus infected cells or immunosuppressive molecules induced by virus infected cells in the microenvironment surrounding the virus infected cells, while simultaneously switching on co-stimulatory or co-inhibitory pathways on T cells, as well as method for converting immunosuppressive signals in cells, tissues, and subjects into stimulatory signals, and immunotherapy-based methods for treating cancer and chronic viral infections.

18 Claims, 28 Drawing Sheets

(56) References Cited

OTHER PUBLICATIONS

Brahmer et al., Safety and activity of anti-PDL1 antibody in patients with advanced cancer. J Urol. Dec. 2012;188(6):2148-9.
Callahan et al., At the bedside: CTLA-4- and PD-1-blocking antibodies in cancer immunotherapy. J Leukoc Biol. Jul. 2013;94(1):41-53.
Carreno et al., A dendritic cell vaccine increases the breadth and diversity of melanoma neoantigen-specific T cells. Science. May 15, 2015;348(6236):803-8.
Chen et al., Oncology Meets Immunology: The Cancer-Immunity Cycle. Immunity. Jul. 25, 2013;39(1):1-10.
Dal Porto et al., A soluble divalent class I major histocompatibility complex molecule inhibits alloreactive T cells at nanomolar concentrations. Proc Natl Acad Sci U S A. Jul. 15, 1993;90(14):6671-5.
De Paoli et al., Microenvironmental abnormalities induced by viral cooperation: Impact on lymphomagenesis. Semin Cancer Biol. Oct. 2015;34:70-80.
Freeman et al., Protect the killer: CTLs need defenses against the tumor. Nat Med. Aug. 2002;8(8):787-9.
Gajewski et al., Innate and adaptive immune cells in the tumor microenvironment. Nat Immunol. Oct. 2013;14(10):1014-22.
Gubin et al., Checkpoint blockade cancer immunotherapy targets tumour- specificmutant antigens. Nature. Nov. 27, 2014;515(7528):577-8.
Gubin et al., Tumor neoantigens : building a framework for personalized cancer immunotherapy. J Clin Invest. Sep. 2015;125(9):3413-21.
He et al., Agonist anti-human CD27 monoclonal antibody induces T cell activation and tumor immunity in human CD27-transgenic mice. J Immunol. Oct. 15, 2013;191(8):4174-83.
Herrmann et al., CTLA4 aptamer delivers STAT3 siRNA to tumor-associated and malignant T cells. The J Clin Invest. Jul. 2014;124(7):2977-87.
Hurwitz et al., T cell avidity and tumor immunity: Problems and solutions. Cancer Microenviron. Aug. 2014;7(1-2):1-9.
Iwai et al., Involvement of PDL1 on tumor cells in the escape from host immune system and tumor immunotherapy by PDL1 blockade. Proc Natl Acad Sci U S A. Sep. 17, 2002;99(19):12293-7.
Kamphorst et al., Manipulating the PD-1 pathway to improve immunity. Curr Opin Immunol. Jun. 2013;25(3):381-8.
Karwacz et al., PDL1 co-stimulation contributes to ligand-induced T cell receptor down-modulation on CD8+ T cells. EMBO Mol Med. Oct. 2011;3(10):581-92.
Khong et al., Selection of tumor variants in the generation of [ldquo]tumor escape[rdquo] phenotypes. Nat Immunol. Nov. 2002;3(11):999-1005.
Kosmides et al., Dual targeting nanoparticle stimulates the immune system to inhibit tumor growth. ACS Nano. Jun. 27, 2017;11(6):5417-5429.
Kosmides et al., Dual-targeting nanoparticles for reprogrammed T cell responses in the tumor microenvironment. J Immunother Cancer. 2014; 2(Suppl 3):P108.
Mathan et al., Human Plasmacytoid Dendritic Cells: From Molecules to Intercellular Communication Network. Front Immunol. Nov. 12, 2013;4:372.
Meyer et al., Biodegradable Nanoellipsoidal Artificial Antigen Presenting Cells for Antigen Specific T-Cell Activation. Small. Apr. 2015;11(13):1519-25.
Oelke et al., Overview of a HLA-Ig Based "Lego-like System" for T Cell Monitoring, Modulation and Expansion. Immunol Res . Jul. 2010;47(1-3):248-56.
Peggs et al., PD-1 blockade: promoting endogenous anti-tumor immunity. Expert Rev Anticancer Ther. Oct. 2012;12(10):1279-82.
Perica et al., Nanoscale artificial antigen presenting cells for T cell immunotherapy. Nanomedicine. Jan. 2014;10(1):119-29.
Pilon-Thomas et al., Blockade of programmed death ligand 1 enhances the therapeutic efficacy of combination immunotherapy against melanoma. J Immunol. Apr. 1, 2010;184(7):3442-9.
Prodeus et al., Targeting the PD-1/PD-L1 Immune Evasion Axis With DNA Aptamers as a Novel Therapeutic Strategy for the Treatment of Disseminated Cancers. Mol Ther Nucleic Acids. Apr. 28, 2015;4(4):e237.
Rabinovich et al., Immunosuppressive strategies that are mediated by tumor cells. Annu Rev Immunol. 2007;25:267-96.
Robert et al., Anti-programmed-death-receptor-1 treatment with pembrolizumab in ipilimumab-refractory advanced melanoma: a randomised dose-comparison cohort of a phase 1 trial. Lancet. Sep. 20, 2014;384(9948):1109-17.
Robert et al., Nivolumab in previously untreated melanoma without BRAF mutation. N Engl J Med. Jan. 22, 2015;372(4):320-30.
Rosenberg et al., Adoptive cell transfer as personalized immunotherapy for human cancer. Science. Apr. 3, 2015;348(6230):62-8.
Santulli-Marotto et al., Multivalent RNA aptamers that inhibit CTLA-4 and enhance tumor immunity. Cancer Res. Nov. 1, 2003;63(21):7483-9.
Sasawatari et al., Efficient priming and expansion of antigen-specific CD8+ T cells by a novel cell-based artificial APC. Immunol Cell Biol. Dec. 2006;84(6):512-21.
Shen et al., Latex bead-based artificial antigen-presenting cells induce tumor-specific CTL responses in the native T-cell repertoires and inhibit tumor growth. Immunol Lett. Feb. 2013;150(1-2):1-11.
Shindo et al., Combination Immunotherapy with 4-1BB Activation and PD-1 Blockade Enhances Antitumor Efficacy in a Mouse Model of Subcutaneous Tumor. Anticancer Res. Jan. 2015;35(1):129-36.
Shuford et al., 4-1BB costimulatory signals preferentially induce CD8+ T cell proliferation and lead to the amplification in vivo of cytotoxic T cell responses. J Exp Med. Jul. 7, 1997;186(1):47-55.
Soldevilla et al., Aptamers: A Feasible Technology in Cancer Immunotherapy. J Immunol Res. 2016;2016:1083738.
Topalian et al., Safety, Activity, and Immune Correlates of Anti-PD-1 Antibody in Cancer. N Engl J Med. Jun. 28, 2012;366(26):2443-54.
Turtle et al., Artificial antigen presenting cells for use in adoptive immunotherapy. Cancer J. Jul.-Aug. 2010;16(4):374-81.
Vasievich et al., The suppressive tumor microenvironment: a challenge in cancer immunotherapy. Mol Pharm. Jun. 6, 2011;8(3):635-41.
Weder et al., Testing for HLA/peptide tetramer-binding to the T cell receptor complex on human T lymphocytes. Results Immunol. May 10, 2012;2:88-96.
Yadav et al., Predicting immunogenic tumour mutations by combining mass spectrometry and exome sequencing. Nature. Nov. 27, 2014;515(7528):572-6.
Zhou et al., Blockade of programmed death-1 pathway rescues the effector function of tumor-infiltrating T cells and enhances the antitumor efficacy of lentivector immunization. J Immunol. Nov. 1, 2010;185(9):5082-92.
International Search Report and Written Opinion for PCT/US2017/048196, dated Dec. 4, 2017, 13 pages.
Examination Report for IL App. No. 264999, dated Feb. 16, 2022, 4 pages.

\* cited by examiner

IMMUNOSWITCH NANOPARTICLES FOR REPROGRAMMED T CELL RESPONSES

CROSS-REFERENCE TO RELATED APPLICATIONS

This application is a continuation of U.S. patent application Ser. No. 16/327,508, filed Feb. 22, 2019, which is a 371 national stage entry of Int'l Pat. App. No. PCT/US2017/048196, filed Aug. 23, 2017, which claims the benefit of U.S. Provisional Application Nos. 62/378,406, filed Aug. 23, 2016, and 62/515,810, filed Jun. 6, 2017, each of which is incorporated herein by reference in its entirety.

STATEMENT REGARDING FEDERALLY SPONSORED RESEARCH

This invention was made with government support under grant DGE-1232825 awarded by the National Science Foundation; grant 2T32CA153952-06 awarded by the National Institutes of Health; grant F31CA206344 awarded by the National Cancer Institute of the National Institutes of Health; grant P01-AI072677 awarded by the National Institutes of Health; grant R01-CA108835 awarded by the National Institutes of Health, and grant R21-CA185819 awarded by the National Institutes of Health. The government has certain rights in the invention.

INTRODUCTION

Recent work in cancer immunology has revealed the important interplay between cancer and the immune system. Cancer can lead to the expression of neoantigens and subsequently initiate the activation of tumor-antigen specific T cells and tumor cell death in what is known as the Cancer-Immunity Cycle. (Chen, et al., 2013) Cancer occurs when there is a blockade of one of these steps, and current therapeutics aim to take down these barriers.

Many developing immunotherapies, including adoptive cell transfer (ACT), (Rosenberg, et al., 2015) T cell activation with artificial antigen presenting cells (aAPCs), (Oelke, et al., 2010; Turtle, et al., 2011; Meyer, et al., 2014; Sasawatari, et al., 2006; Shen, et al., 2013; Perica, et al., 2014) vaccination, (Gubin, et al., 2014; Yadav, et al., 2014) and chimeric-antigen receptors, (Barrett, et al., 2014) stimulate an adaptive immune response against antigens known to be uniquely expressed or upregulated by a patient's tumor. However, these approaches require a priori knowledge of the tumor antigen to activate against (Gubin, et al., 2015; Carreno, et al., 2015; Weder, et al., 2012) which can be difficult to determine based on patient-to-patient mutation variability. Additionally, T cells are stimulated through the interaction of the T cell receptor (TCR) with peptide in the context of the major histocompatibility complex which is the most polymorphic gene in the human genome. These approaches are therefore considered personalized cancer therapeutics (Rosenberg, et al., 2015) which increases the cost, time, and difficulty in using them as a widespread approach. Finally, activating a clonal population of T cells against a single tumor antigen has been hypothesized to enable antigenic escape and the growth of resistant tumor cell mutants. (Khong, et al., 2002)

Even when tumor-targeting T cells are present, the tumor microenvironment often upregulates immunosuppressive cytokines and surface antigens that diminish their cytotoxic effects. (Freeman, et al., 2002; Ahmad, et al., 2004; Bono, et al., 2015; Rabinovich, et al., 2007; Vasievich, et al., 2011; Zhou, et al., 2010) Programmed death ligand 1 (PDL1) is one such cell surface checkpoint molecule upregulated on many cancers including melanoma, ovarian cancer, renal-cell cancer, and nonsmall-cell lung cancer (Kamphorst, et al., 2013). This is paired with a large proportion of tumor-infiltrating lymphocytes (TILs) expressing PDL1's receptor, programmed death 1 (PD-1) (Peggs, et al., 2012), which upon ligation suppresses the effector functions of these tumor-targeting lymphocytes. Tumor cells with higher PDL1 expression decrease tumor cell lysis and secretion of IFN-γ, a proinflammatory cytokine, by CD8+ T cells. (Iwai, et al., 2002) The interaction between PD-1 and PDL1 also causes a downregulation in TCR expression on CD8+ T cells, (Karwacz, et al., 2011) thereby reducing their activation potential. Checkpoint blockade with monoclonal antibodies against PD-1 and PDL1 delay tumor growth in mouse melanoma and myeloma models, (Iwai, et al., 2002; Pilon-Thomas, et al., 2010) and FDA approved monoclonal anti-PD-1 and anti-CTLA-4 antibodies have shown overall response rates of up to approximately 30%. (Callahan, et al., 2013; Ascierto, et al., 2015; Robert, et al., 2015; Robert, et al., 2014) However, expression of PDL1 within the tumor microenvironment correlates with but cannot predict response, (Topalian, et al., 2012) indicating that there are other mechanisms at play. Complete response rates in these patients have been as low as 5% (Brahmer, et al., 2012) and demonstrates the need for improvement of checkpoint blockade.

SUMMARY

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning. A Laboratory Manual*, 3$^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange 10$^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, www.ncbi.nlm.nih.gov/omim/ and in Online Mendelian Inheritance in Animals (OMIA), a database of genes, inherited disorders and traits in animal species (other than human and mouse), at www.omia.angis.org.au/contact.shtml.

One of the largest obstacles to overcome in cancer immunotherapy is the suppressive actions of the tumor microenvironment. Combination therapies that activate an immune response as well as block inhibitory pathways have potential in creating a prolonged and effective anti-tumor response. The presently disclosed subject matter provides, in one embodiment, an immunoswitch particle that combines an inhibitory checkpoint signal, PDL1, in the tumor microenvironment with a co-stimulatory, 4-1BB, signal to T cells for efficient stimulation. By combining targeting molecules (ligands) against both molecules on a single platform, the particles can physically link effector and target cells and switch off the inhibitory PDL1 pathway on tumor cells while simultaneously switching on the stimulatory 4-1BB pathway on murine CD8 cells. The presently disclosed immunoswitch particles bypass the requirement for a priori knowledge of tumor antigens to activate T cells against tumors. The presently disclosed immunoswitch particles also increase activation of CD8 cells in vitro in the presence of cognate tumor target cells, and enhance effector-target cell conjugation. The presently disclosed subject matter demonstrates that immunoswitch particles can treat pre-established tumors and extend survival in two in vivo models of murine melanoma and colon cancer. Immunoswitch particle efficacy is dependent on the presence of both targeting moieties on the same nanoparticle. The presently disclosed subject matter shows the potential of a new genre of immunomodulatory signal-switching approaches.

In an aspect, the presently disclosed subject matter provides an immunotherapy method of treating a cancer or a chronic viral infection in a subject in need thereof, the method comprising administering an effective amount of an immunoswitch particle to the subject, wherein the immunoswitch particle comprises a nanoparticle comprising a first agent that targets an immunosuppressive pathway in a tumor cell or an immunosuppressive molecule induced by the tumor in the tumor microenvironment, or the first agent targets a virus infected cell or an immunosuppressive molecule induced by the virus infected cell in microenvironment surrounding the virus infected cell, and a second agent that targets a co-stimulatory or co-inhibitory pathway in a T cell, thereby simultaneously targeting in the subject the immunosuppressive pathway in the tumor cell or tumor microenvironment, or the virus infected cell or microenvironment surrounding the virus infected cell, and the co-stimulatory or co-inhibitory pathway in the T cell, wherein simultaneously targeting the immunosuppressive pathway in the tumor cell or tumor microenvironment, or virus infected cell or microenvironment surrounding the virus infected cell, and the co-stimulatory or co-inhibitory pathway in the T cell enhances the subject's immune system and treats the cancer or chronic viral infection in the subject.

In particular embodiments, the first agent targets the immunosuppressive pathway in a tumor cell and the method inhibits growth of the subject's tumor compared to growth of the subject's tumor in the absence of administration of the immunoswitch particle. In particular embodiments, the first agent targets the immunosuppressive pathway in virus infected cells and the method inhibits multiplicity of infection of the virus infected cells compared to the multiplicity of infection of the viral infected cells in the absence of administration of the immunoswitch particle.

In particular embodiments, the first agent targets the immunosuppressive pathway in a tumor cell and the method extends the length of survival of the subject compared to length of survival of the subject in the absence of administration of the immunoswitch particle. In particular embodiments, the first agent targets the immunosuppressive pathway in a virus infected cell and the method extends latency of the virus in the subject compared to latency of the virus in the subject in the absence of administration of the immunoswitch particle.

In particular embodiments, the first agent comprises an agent that targets an immune checkpoint protein. In particular embodiments, the immune checkpoint receptor is selected from the group consisting of PDL1 and PDL2. In particular embodiments, the first agent comprises an antibody or functional fragment thereof conjugated to the nanoparticle, wherein the antibody is selected from the group consisting of a PDL1 antagonist antibody or functional variant thereof, a PDL2 antagonist antibody or functional variant thereof, and combinations thereof.

In particular embodiments, the T cell co-stimulatory pathway is selected from the group consisting of the 4-1BB signaling pathway, the CD27 signaling pathway, the CD28 signaling pathway, the ICOS signaling pathway, the CD226 signaling pathway, the CRTAM signaling pathway, the TIM1 signaling pathway, the CD2 signaling pathway, the SLAM signaling pathway, the CD84 signaling pathway, the Ly9 signaling pathway, the Ox40 signaling pathway, and the CRACC signaling pathway.

In particular embodiments, the T cell co-inhibitory pathway is selected from the group consisting of the CTLA4 signaling pathway, the PD1 signaling pathway, the PD1H signaling pathway, the BTLA signaling pathway, the B71 signaling pathway, the PDL1 signaling pathway, the TIGIT signaling pathway, the TIM2 signaling pathway, the TIM3 signaling pathway, the LAIR1 signaling pathway, the LAG3 signaling pathway, and the CD160 signaling pathway.

In particular embodiments, the second agent comprises an antibody or functional variant thereof conjugated to the nanoparticle, wherein the antibody is selected from the group consisting of a 4-1BB agonist antibody or functional variant thereof, a CD27 agonist antibody or a functional variant thereof, a CD28 agonist antibody or functional variant thereof, a ICOS agonist antibody or functional variant thereof, a CD226 agonist antibody or functional variant thereof, a CRTAM agonist antibody or functional variant thereof, a TIM1 agonist antibody or functional variant thereof, a CD2 agonist antibody or functional variant thereof, a SLAM agonist antibody or functional variant thereof, a CD84 agonist antibody or functional variant thereof, a Ly9 agonist antibody or functional variant thereof, an Ox40 agonist antibody or functional variant thereof, a CRACC agonist antibody or functional variant thereof, and combinations thereof.

In particular embodiments, the second agent comprises an antibody or functional variant thereof conjugated to the nanoparticle, wherein the antibody is selected from the group consisting of a CTLA4 antagonist antibody or functional variant thereof, a PD1 antagonist antibody or functional variant thereof, a PD1H antagonist antibody or functional variant thereof, a BTLA antagonist antibody or functional variant thereof, a B71 antagonist antibody or functional variant thereof, a PDL1 antagonist antibody or functional variant thereof, a TIGIT antagonist antibody or functional variant thereof, a TIM2 antagonist antibody or functional variant thereof, a TIM3 antagonist antibody or functional variant thereof, a LAIR1 antagonist antibody or functional variant thereof, a LAG3 antagonist antibody or functional variant thereof, a CD160 antagonist antibody or functional variant thereof, and combinations thereof.

In particular embodiments, the first agent is a PDL1 antagonist antibody and the second agent is a 4-1BB agonist antibody. In particular embodiments, the first agent is a PDL1 antagonist antibody and the second agent is a CD28 agonist antibody. In particular embodiments, the first agent is a CD73 antagonist antibody and the second agent is a 4-1BB agonist antibody. In particular embodiments, the first agent is a PD-L1 antagonist antibody and the second agent is a CD27 agonist antibody. In particular embodiments, the first agent is a CD73 antagonist antibody and the second agent is a CD27 agonist antibody. In particular embodiments, the first agent is a CD73 antagonist antibody and the second agent is a CD28 agonist antibody.

In particular embodiments, the T cell is selected from the group consisting of a CD4+ T cell and a CD8+ T cell.

In particular embodiments, the tumor is selected from the group consisting of melanoma and colon cancer.

In particular embodiments, the chronic viral infection is due to a virus selected from the group consisting of human immunodeficiency virus (HIV), hepatitis B virus (HBV), and hepatitis C virus (HCV).

In particular embodiments, the subject is a human subject.

In particular embodiments, administration of the immunoswitch nanoparticle to the subject comprises intratumoral injection.

In particular embodiments, the nanoparticle has a diameter ranging from about 50 nm to about 100 nm. In particular embodiments, the nanoparticle has a diameter of about 80 nm.

In an aspect, the presently disclosed subject matter provides an immunoswitch particle comprising a nanoparticle comprising a first agent that targets an immunosuppressive pathway in a tumor cell or immunosuppressive molecule induced by the tumor cell in the tumor microenvironment, or a virus infected cell or immunosuppressive molecule induced by the virus infected cell in the microenvironment surrounding the virus infected cell, and a second agent that simultaneously targets a co-stimulatory pathway or co-inhibitory pathway in a T cell.

In an aspect, the presently disclosed subject matter provides a method of converting an immune inhibitory signal in a subject in need thereof into an immune stimulatory signal comprising administering an effective amount of the immunoswitch particle to the subject, wherein the first agent targets the immunosuppressive pathway in the tumor cell or immunosuppressive molecule induced by the tumor cell in the tumor microenvironment, or virus infected cell or immunosuppressive molecule induced by the virus infected cell in the microenvironment surrounding the virus infected cell in the subject, and the second agent simultaneously targets the co-stimulatory pathway or co-inhibitory pathway in the subject's T cells, thereby converting an immune inhibitory signal in the subject into an immune stimulatory signal.

In some embodiments, the nanoparticle has an increased retention time in the subject relative to soluble first and second agents, or relative to separate nanoparticles comprising the first agent and the second agent.

In some embodiments, administration of the nanoparticle reduces or prevents tumor metastasis. In some embodiments, administration of the nanoparticle inhibits the growth of tumor metastases. In some embodiments, the tumor metastasis expresses the same antigen as the tumor cell. In some embodiments, the same antigen comprises Her2/Neu, BRCA1, BRCA2, or K-Ras. In some embodiments, tumor-specific CD8+ T cells activation is increased.

In some embodiments, the nanoparticle is administered to the subject intratumorally. In some embodiments, the nanoparticle is administered to the subject intravenously. In some embodiments, administration of the nanoparticle induces a local immune response. In some embodiments, administration of the nanoparticle induces a systemic immune response. In some embodiments, administration of the nanoparticle induces T cell memory, CD4 cell memory, or CD8 cell memory, or a combination thereof. In some embodiments, administration of the nanoparticle induces T cell memory, inhibits tumor growth, prevents tumor growth, or delays tumor growth.

In another aspect, provided is a T cell produced during a method of treatment as detailed herein.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

Having thus described the presently disclosed subject matter in general terms, reference will now be made to the accompanying Figures, which are not necessarily drawn to scale, and wherein:

FIG. 1A, FIG. 1B, FIG. 1C, FIG. 1D, FIG. 1E, FIG. 1F, FIG. 1G, FIG. 1H, FIG. 1I, FIG. 1J, FIG. 1K, FIG. 1L, FIG. 1M, and FIG. 1N show immunoswitch particles present both anti-4-1BB and anti-PDL1 antibodies. FIG. 1A shows iron-dextran nanoparticle platform is 80 nm in diameter. Unconjugated iron-dextran nanoparticles size was measured by nanoparticle tracking analysis. Error bars represent SEM of 3 separate captures of a single sample. The mode of the dataset is 81.1+/−1.6 nm and the mean of the dataset is 96.0+/−1.9 nm. Immunoswitch particles link PDL1 checkpoint blockade with 4-1BB co-stimulation. FIG. 1B shows immunoswitch particle synthesis schematic. Antagonistic anti-PDL1 and agonistic anti-4-1BB antibodies are conjugated to the surface of 80 nm iron-dextran nanoparticles. FIG. 1C shows average number of anti-4-1BB and anti-PDL1 molecules per particle, as measured by fluorescently labeled secondary antibody. Mean+/−SEM is shown, averaged across 3 independent experiments. No significant differences in antibody level per each particle type, as measured by two-way ANOVA with Bonferroni posttest. Particles have equimolar ratios of antibodies as measured by fluorescently labeled secondary antibody. FIG. 1D shows schematic showing immunoswitch particle interaction with CD8 cell and cognate target cell. FIG. 1E shows flow cytometry plots of PD-1 and 4-1BB expression on CD8 cells on day 0 (dotted) and day 8 after aAPC stimulation on days 0 and 4 (solid), as compared with isotype (grey, filled). PD-1 and 4-1BB are upregulated on day 0 activated 2C CD8 cells, as measured by flow cytometry. Grey—isotype, dotted—naïve, solid—activated. FIG. 1F shows flow cytometry plot of PDL1 expression by B16-SIY cells on day 0 (dotted) and 48 hours after IFN-γ treatment (solid), as compared with isotype (grey). PDL1 is upregulated on IFN-γ treated B16-SIY cells. Grey—isotype, dotted naïve, solid—treated. FIG. 1G and FIG. 1H show B16-SIY and B16-F10 upregulate PDL1 but not PD-L2 in response to IFN-γ incubation. FIG. 1G shows B16-F10 cells were cultured in media supplemented with 20 ng/ml IFN-γ for 48 hours, and PDL1 and PD-L2 expression was assessed by flow cytometry. PDL1 (left) but not PD-L2 (right) is upregulated in IFN-γ treated (solid) vs. untreated (dotted) cells. FIG. 1H shows B16-SIY cells were cultured in media supplemented with 20 ng/ml IFN-γ for 48 hours, and PD-L2 expression was assessed by flow cytometry. PD-L2 was not upregulated in treated (solid) vs. untreated (dotted) cells. Isotypes are shown in grey. FIG.

1I and FIG. 1J show soluble anti-4-1BB and anti-PDL1 antibody increase PD-1$^{hi}$ CD8 cell activation when co-incubated with PDL1$^{hi}$ target cells. PD-1$^{hi}$ 2C CD8 cells and PDL1$^{hi}$ cognate B16-SIY cells were co-incubated at a 1:1 ratio in the presence of titrating amounts of soluble anti-4-1BB (FIG. 1I) or anti-PDL1 (FIG. 1J) antibody. IFN-γ secretion by CD8 cells was measured by ELISA after 18 hours. Both antibodies induced a significant increase in the level of IFN-γ secretion as compared to isotype at concentrations at and above 10 ng/ml. Mean+/−SEM are shown of three replicates. Significance measured by one-way ANOVA with Dunnett's posttest, comparing each condition to isotype (*p<0.05, *p<0.001). FIG. 1K and FIG. 1L show immunoswitch efficacy in vitro. FIG. 1K shows IFN-γ secretion from PD-1$^{hi}$ CD8 cells co-incubated with PDL1$^{hi}$ B16-SIY cells and immunoswitch particles, isotype particles, or an soluble antibody. Concentrations refer to total antibody in culture. Mean+/−SEM from 3 samples is shown. Significance measured by two-way ANOVA with Bonferroni posttest. Antibody functionality is not lost when antibodies are conjugated to nanoparticles, as immunoswitch particles stimulate CD8+ T cells at least as well as soluble antibody, as measured by ELISA. FIG. 1L shows IFN-γ secretion from PD-1$^{hi}$ CD8 cells co-incubated with PDL1$^{hi}$ B16-SIY or B16-F10 cells (FIG. 1M) and the indicated particle type. Concentrations refer to total antibody in culture. Mean+/−SEM from 3 samples is shown. Significance measured by two-way ANOVA with Bonferroni posttest, and only shown for bead comparisons (i.e. not concentration comparisons) (*p<0.001, **p<0.01, *p<0.05). FIG. 1L shows both anti-4-1BB and anti-PDL1 must be conjugated to the particle for greatest CD8 stimulation, as measured by ELISA. Significance measured by two-way ANOVA (*p<0.001, p<0.01). FIG. 1N the percent specific lysis of B16-SIY cells by 2C CD8+ T cells when co-incubated for 4 hours at a 1:1 effector-target ratio in the presence of immunoswitch particles and 100 μg/ml anti-Kb blocking mAb or isotype control. Significance was measured by two-tailed t-test.

FIG. 2A, FIG. 2B, FIG. 2C, and FIG. 2D show immunoswitch particles increase effector-target cell conjugation. PD-1$^{hi}$ 2C CD8 cells and PDL1$^{hi}$ B16-F10 cells were labeled with a red and green membrane dye, respectively. Cells were co-incubated for 1 hour with immunoswitch or isotype particles, then washed, fixed and read by confocal microscopy or flow cytometry. FIG. 2A shows representative confocal images from each condition showing conjugate formation (green arrows). Amount refers to total mass of antibody during incubation. PD-1$^{hi}$ 2 C CD8 cells (red) and PDL1$^{hi}$ B16-F10 cells (green) were co-incubated with immunoswitch or isotype particles. Conjugate formation was quantified by confocal microscopy, as indicated by green arrows (FIG. 2A, FIG. 2B), or flow cytometry. FIG. 2B shows percent of total CD8 cells forming conjugates were counted. Each data point represents an independent image taken across three independent experiments. 50 ng of immunoswitch particles significantly increased conjugation rate over isotype particles as measured by one-way ANOVA with Dunnett's posttest. FIG. 2C shows Conjugate formation was also measured by gating on double red and green positive cells by flow cytometry. Each data point represents an independent experiment. 50 ng of immunoswitch particles significantly increased conjugation rate over isotype particles as measured by one-way ANOVA with Dunnett's posttest. Dunnett's posttests were used to determine which immunoswitch doses result in higher effector-target cell conjugation than background with isotype particles. (p<0.01, *p<0.001). Combined data from 3 independent experiments are shown. Significance measured by one-way ANOVA with Dunnett's post-test comparing all conditions to isotype (*p<0.001, p<0.01). FIG. 2D shows that conjugate formation was measured by gating on double red and green positive cells by flow cytometry. Each data point represents an independent experiment. 50 ng of immunoswitch particles significantly increased conjugation rate as measured by two-tailed paired t-test.

FIG. 3A, FIG. 3B, and FIG. 3C show immunoswitch particle treatment delays tumor growth in an in vivo B16 murine melanoma model with co-adoptive transfer of PD-1$^{hi}$ specific CD8 cells. Immunoswitch particles decrease tumor growth in vivo. FIG. 3A shows schematic showing in vivo model setup. C57BL/6 mice (n=4 isotype group, n=8 immunoswitch group, n=9/other groups) were injected with 1×10$^6$ B16-SIY cells subcutaneously (s.c.) on day 0. 2C CD8 cells were isolated on day 0, stimulated with aAPC on days 0 and 4, and isolated from the aAPC and injected intravenously (IV) on day 8. Particle and antibody treatments were given intratumorally (IT) on days 8, 11, and 15. In vivo schematic. FIG. 3B shows tumor growth curves show only immunoswitch treatment significantly delayed tumor growth as compared to no treatment, past day 12. Black arrows indicate treatment days. Significance measured by two-way ANOVA with Bonferroni posttest. FIG. 3C shows only immunoswitch treatment significantly extended survival as compared to no treatment. Significance measured by log-rank test. (*p<0.001). Results from two independent experiments are combined. FIG. 3B and FIG. 3C show only immunoswitch particles significantly delay tumor growth and extend survival as compared to no treatment. Significance measured by two-way ANOVA and log-rank test (*p<0.001, *p<0.05).

FIG. 4A, FIG. 4B, FIG. 4C, FIG. 4D, FIG. 4E, FIG. 4F, FIG. 4G, and FIG. 4H illustrate that immunoswitch particles delay tumor growth in the absence of adoptive transfer by linking both anti-4-1BB and anti-PDL1 on the same particle and stimulating a CD8 cell response. FIG. 4A illustrates that C57BL/6 mice (n=6 separate particle treatment, n=11/other groups) were injected with B16-SIY cells s.c. on day 0. Treatment—either immunoswitch particles or a co-injection of anti-4-1BB and anti-PDL1 particles—was injected IT on days 8, 11, and 15. No adoptive transfer of tumor-specific cells was given. FIG. 4B illustrates that immunoswitch particles, but not separate anti-4-1BB and anti-PDL1 particles, delayed tumor growth as compared to no treatment at all time points past day 11. Arrows indicate treatment days. Significance was measured by two-way ANOVA with Bonferroni posttest. FIG. 4C illustrates that only immunoswitch particle treatment significantly extended survival. Significance was measured by log-rank test. D) C57BL/6 mice (n=5/group) were injected with B16-SIY cells as above, and half were treated with immunoswitch particles IT on days 8 and 11. On day 14 TILs and tumor draining lymph nodes (tdLNs) were harvested and analyzed. The non-treated group had significantly larger tumors and a lower CD8 T cell density within the tumor on day 14. Significance was measured by two-tailed t-test. CD4 density within the tumor microenvironment is unchanged with immunoswitch treatment. FIG. 4E illustrates that C57BL/6 mice (n=5/group) were injected with B16-SIY cells s.c. on day 0, and half were treated with immunoswitch particles IT on days 8 and 11. On day 14 TILs were harvested and analyzed. CD4 density with the tumor was unchanged with treatment. Significance measured by one-way ANOVA. FIG. 4F illustrates that CD8 cells within the tdLNs of immunoswitch-treated mice had higher KbSIY (expressed by tumor) specificity (**p<0.01,

*p<0.05). (A-C) Results from two independent experiments are combined. FIG. 4G shows that immunoswitch particles, but not separate anti-4-1BB and anti-PD-L1 mAb particles, delayed tumor growth compared to no treatment at all time points past day 11. Arrows indicate treatment days. Significance was measured by two-way ANOVA with Bonferroni posttest (p=0.007). FIG. 4H shows representative flow plots showing Kb-SIY specificity of CD8+ T cells from tumor draining lymph nodes of immunoswitch (left) or non-treated (right) mice.

FIG. 5A and FIG. 5B show immunoswitch particles remain at injection site longer than soluble antibody. FIG. 5A shows IR images of mice injected with IR-labeled particles or soluble antibody in the right flank at t=0 hours. Nude mice (n=3/group) were injected with IR-labeled soluble antibody or immunoswitch particles. Mice were imaged with a full body IR imager at t=3, 24, 48, and 72 hours post injection. All images from an individual mouse are normalized to each other. FIG. 5B shows change in mean gray value over time in target region of interest. Images from individual mice were normalized to the mean gray value at t=3 hours (see Materials and Methods). An immediate decrease is observed after injection followed by a consistent clearance rate. Clearance from the injection site is greater with soluble antibody than immunoswitch particles at all time points. Significance measured by two-way ANOVA with Bonferroni posttest (***p<0.001).

FIG. 6A, FIG. 6B, and FIG. 6C show immunoswitch particles reverse tumor growth and extend survival in an MC38 murine colon cancer model. FIG. 6A shows C57BL/6 mice (n=6 in isotype group, n=10/other groups) were injected with MC38-OVA cells s.c. on day 0. Treated mice received intratumoral injections on days 8, 11, 15, and 18 and tumors were measured every 2-3 days. FIG. 6B shows only immunoswitch particles significantly delayed and reversed tumor growth as compared with no treatment, past day 22. Significance was measured by two-way ANOVA with Bonferroni posttest. Arrows indicate treatment days. FIG. 6C shows only immunoswitch particles significantly extended survival as compared as compared to no treatment, as measured by the log-rank test (***p<0.001).

FIG. 7A and FIG. 7B show that checkpoint blockade and co-stimulatory antibodies presented on the same nanoparticle. FIG. 7A shows an in vivo schematic. FIG. 7B shows that only immunoswitch particles significantly delay tumor growth and extend survival as compared to no treatment. Significance measured by two-way ANOVA and log-rank test (**p<0.01, *p<0.05).

(FIG. 9A) Flow plots of Kb-SIY staining on CD8+ T cells from the spleens of immunoswitch-treated and non-treated mice. (FIG. 9B) Percent of Kb-SIY+/CD8+ T cells in the peripheral blood of immunoswitch-treated and non-treated mice.

Figure 10A:
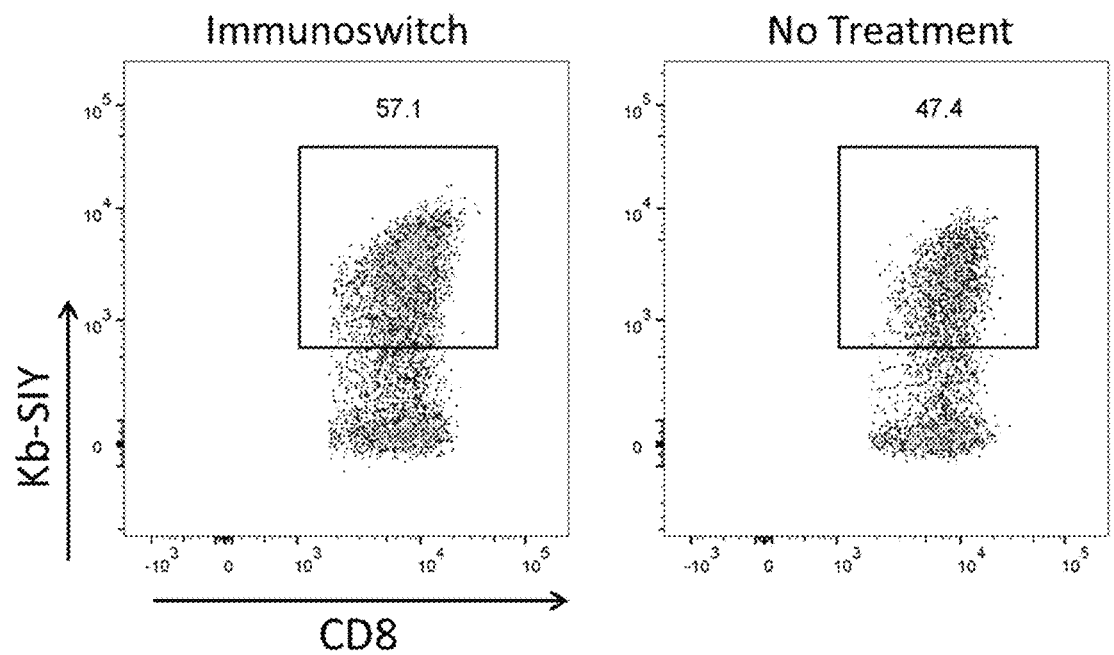
Figure 10B:
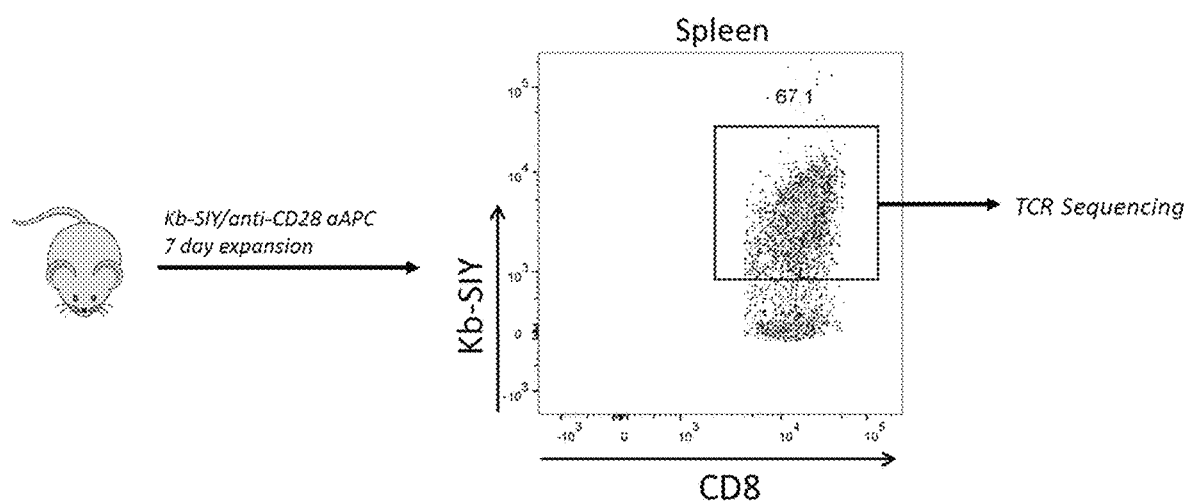

FIG. 10A and FIG. 10B show that a significant portion of the anti-tumor response in the presence and absence of immunoswitch treatment is Kb-SIY specific. (FIG. 10A) Representative flow plots of Kb-SIY staining on CD8+ T cells from the TILS of immunoswitch-treated and non-treated mice. (FIG. 10B) Expansion protocol used to sequence the Kb-SIY specific CD8+ T cell response. Splenocytes from non-tumor bearing C57BL/6 mice were expanded with Kb-SIY/anti-CD28 aAPC for 7 days. Kb-SIY+ cells were sorted and sequenced after 7 days.

Figure 11A:
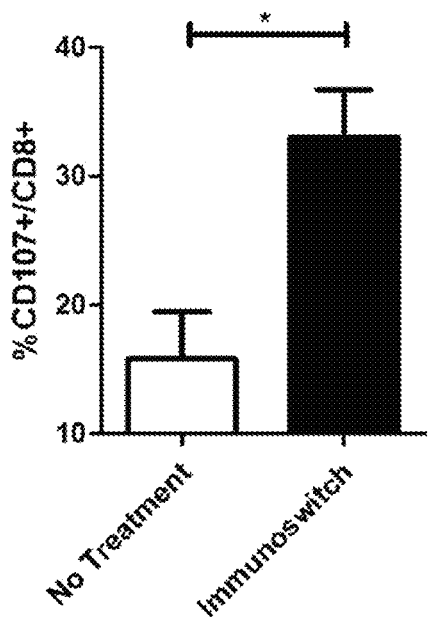
Figure 11B:
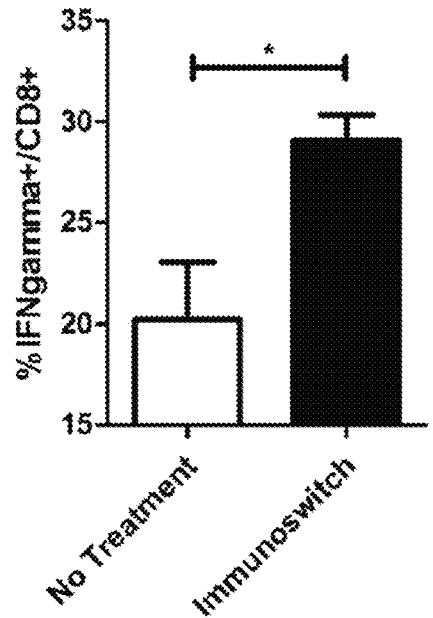
Figure 11C:
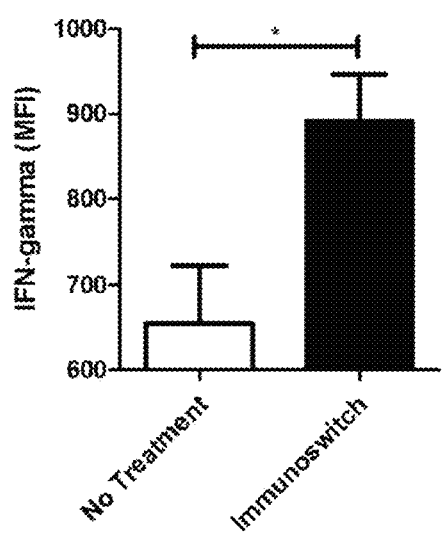

FIG. 11A, FIG. 11B, and FIG. 11C show tumor-specific CD8+ tumor-infiltrating lymphocytes of immunoswitch treated mice have increased functionality. (FIG. 11A) C57BL/6 mice (n=3/group) were injected with B16-SIY cells SC on day 0. Immunoswitch particles were injected IT on days 8 and 11. On day 14 tumor-infiltrating lymphocytes were harvested and re-stimulated with SIY pulsed RMA-S cells. Intracellular cytokine staining indicated an increased frequency of CD107 producing (FIG. 11A) and IFN-γ producing (FIG. 11B) CD8+ T cells following immunoswitch treatment. The mean fluorescence intensity (MFI) of IFN-γ+ cells was increased in treated mice. Significance was measured by one-tailed t-test (*p<0.05).

Figure 12A:
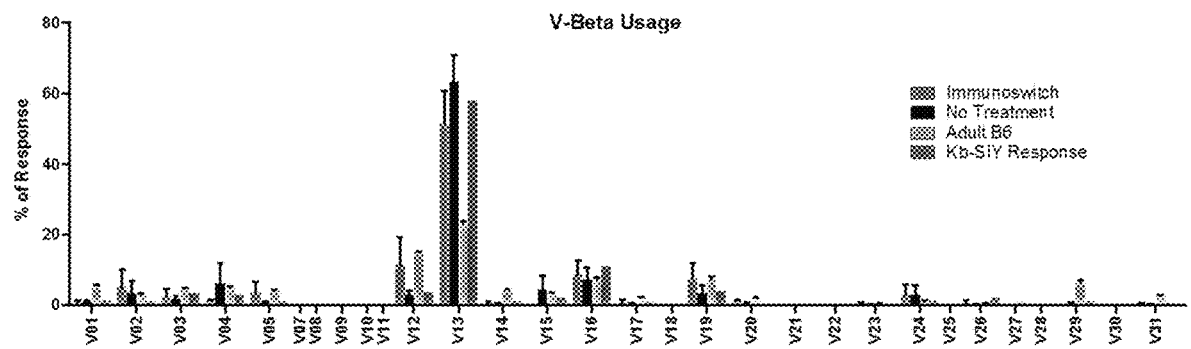
Figure 12B:
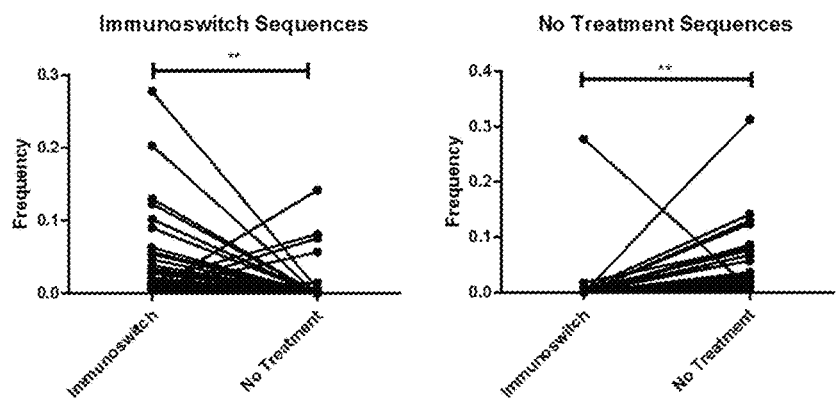
Figure 12C:
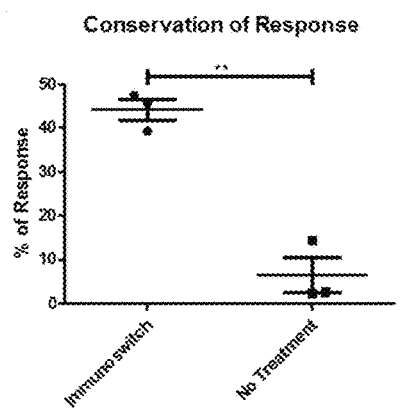

FIG. 12A, FIG. 12B, and FIG. 12C show immunoswitch treatment alters the CD8+ T cell repertoire. (FIG. 12A) T cell receptor V-beta usage in CD8+ tumor-infiltrating lymphocytes from immunoswitch-treated, non-treated, non-tumor bearing adult B6 mice, or a Kb-SIY-specific CD8+ T cell response. C57BL/6 mice (n=3/group) were injected with B16-SIY cells SC on day 0. Immunoswitch particles were injected IT into treated mice on days 8 and 11, and tumor-infiltrating lymphocytes were isolated on day 14. Immunoswitch treated and non-treated mice skew towards T cell receptor V-beta 13, as is seen in a Kb-SIY specific response. (FIG. 12B) T cell receptor clones present in the CD8+ tumor-infiltrating lymphocytes of immunoswitch-treated mice are present at significantly higher frequencies than in the tumor-infiltrating lymphocytes of non-treated mice (left). T cell receptor clones present in the CD8+ tumor-infiltrating lymphocytes of non-treated mice are present at significantly higher frequencies than in the tumor-infiltrating lymphocytes of immunoswitch-treated mice (right). Significance measured by two-tailed paired t test (p<0.01). (FIG. 12C) CD8+ T cell receptor clones are conserved to a significantly higher extent in immunoswitch-treated mice. Each point represents the percent of overlapping clonal response between two mice of the same group. Significance measured by two-tailed t test (p<0.01).

Figure 13:
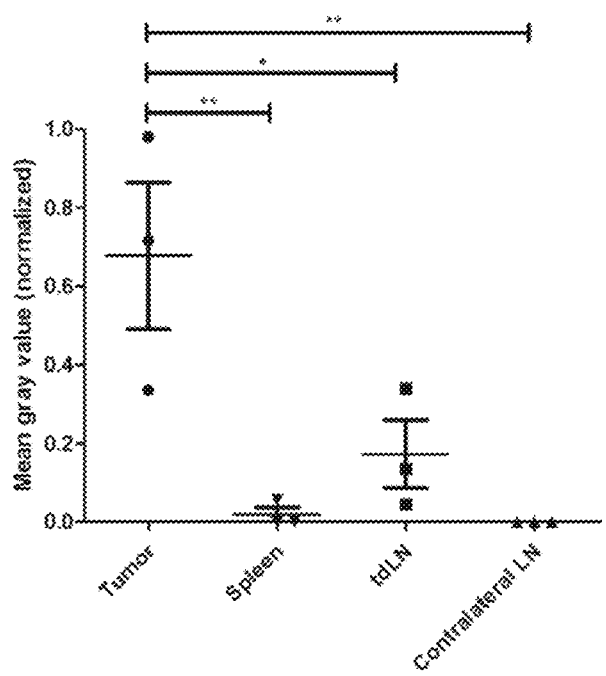

FIG. 13 shows C57BL/6 mice (n=3) were injected with IR-labeled immunoswitch particles 8 days after B16-SIY inoculation. Tumor, spleen, tumor draining lymph node, and contralateral lymph node were harvested 48 hours after treatment. Immunoswitch particles are retained primarily in the tumor and tumor draining lymph node. Values were recorded relative to the sensor's maximum (i.e. 0-1 scale). Significance measured by two-way ANOVA with Tukey's posttest.

Figure 14:
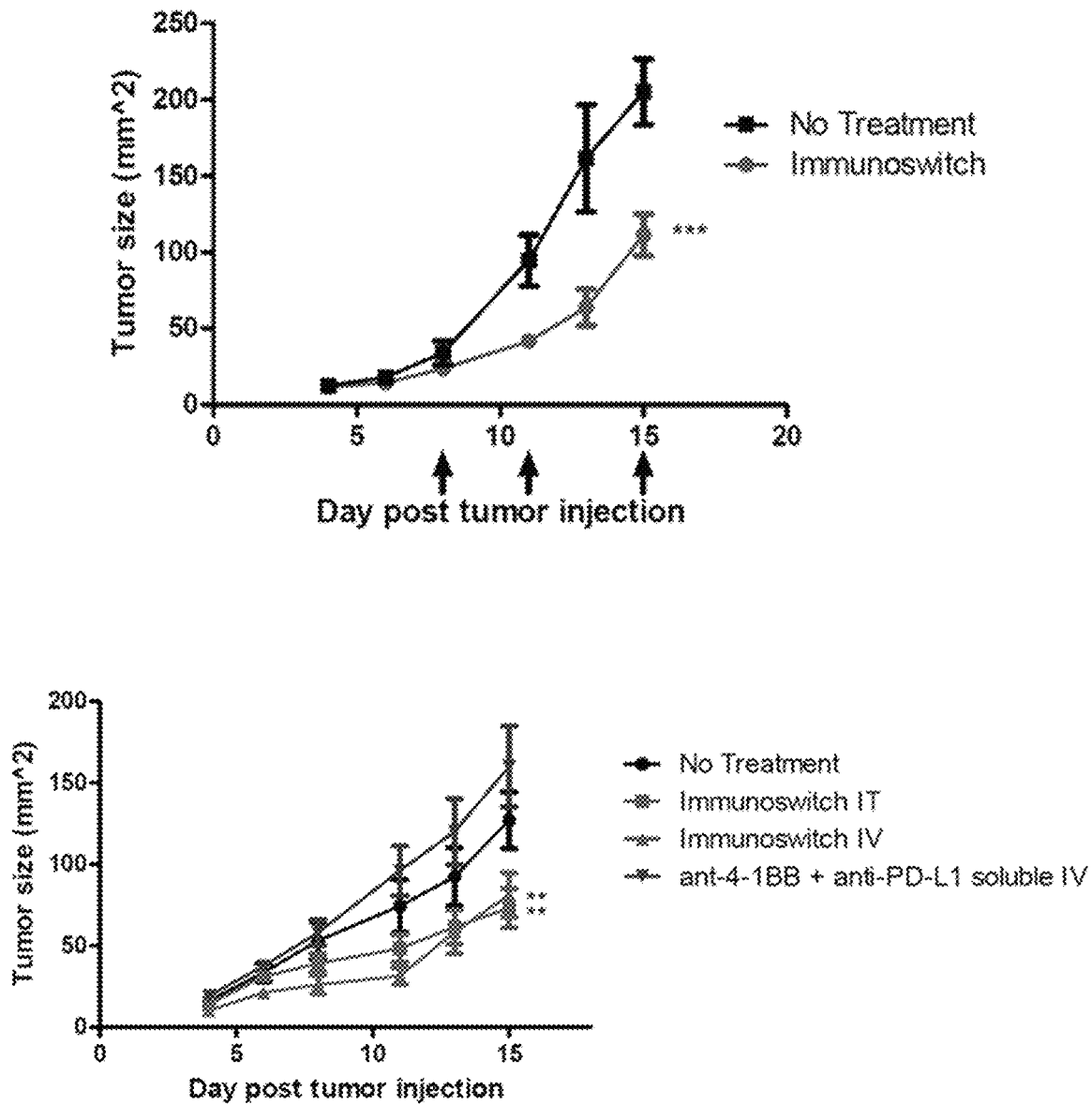

FIG. 14 shows C57BL/6 mice (n=5/group) were injected with B16-F10 cells SC on day 0. Treated mice received IT injections on days 8, 11, and 15. Immunoswitch treatment delayed tumor growth as compared to no treatment, past day 11. Significance was measured by two-way ANOVA with Bonferroni posttest. Arrows indicate treatment days. C57BL/6 mice (n>5/group) were injected with B16-SIY cells SC on day 0. IV immunoswitch particles were administered on days 4, 8, 11, and 15 and days 8, 11, and 15 by IT. Immunoswitch particles injected either IT or IV delay tumor growth past day 13 compared to no treatment (p<0.01). Soluble injected antibody has no effect on tumor growth. Significance was measured by two-way ANOVA with Bonferroni posttest.

Figure 15:
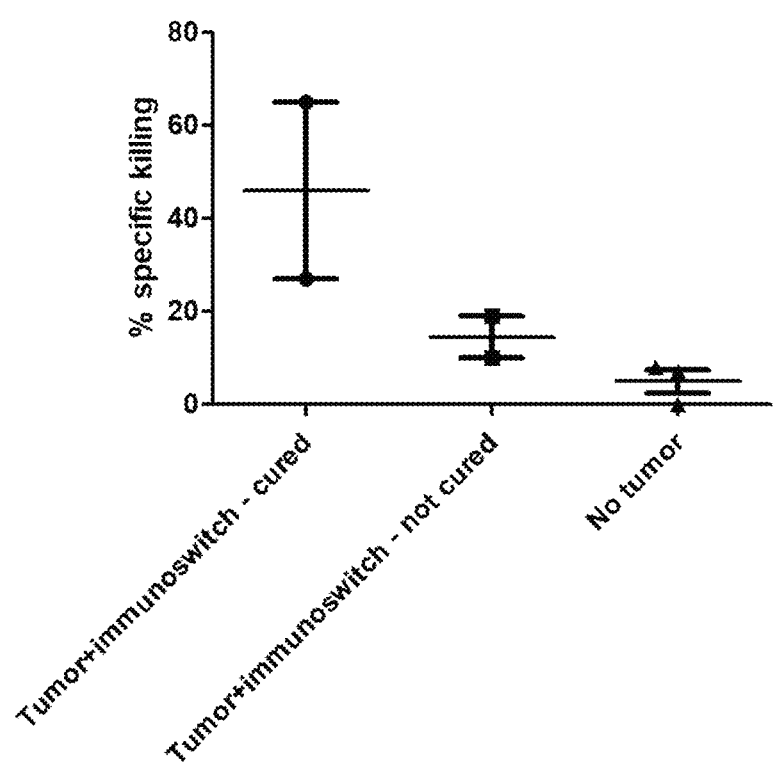

FIG. 15 is a graph of specific killing for mice inoculated with 1×10$^6$ MC38-OVA murine colon cancer cells and immunoswitch particles, showing that immunoswitch particle treatment results in systemic immunity in cured animals.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The immune system is able to target pathogenic and tumor cells through recognition of antigens (e.g., overexpressed, mutant antigens, etc.) expressed by the pathogenic and tumor cells. However, because cancer is derived from self-tissue, most high-avidity T cell clones are deleted in the thymus, leaving only low-avidity tumor-specific T cells. Checkpoint molecules expressed by tumor cells then act to further suppress these T cells and result in a blockade in the cancer-immunity cycle and a non-functional anti-tumor response.

Blocking antibodies against checkpoint molecules such as PD-1 and PDL1 have resulted in responses in a fraction of patients. However, complete response rates in these patients have been as low as 5% indicating that checkpoint blockade alone is not an optimized therapy. Checkpoint blockade can enhance the activity of PD-1 infiltrating lymphocytes within the tumor microenvironment, but will not induce a response in T cells that require additional co-stimulation to mount a response. For activation of T cells with a greater activation threshold, it has been shown that agonistic antibodies against 4-1BB can rescue the function of such low-avidity tumor-specific T cells. Combination therapies that combine checkpoint blockade with other immune-stimulants therefore have the greatest potential to induce and maintain an anti-tumor immune response and jump-start the cancer immunity cycle.

The presently disclosed subject matter describes an immunoswitch nanoparticle that targets immunosuppressive pathways in tumor and viral cells while simultaneously targeting co-stimulatory pathways in T cells utilizing a single injectable platform. For example, a presently disclosed immunoswitch nanoparticle can target the immunosuppressive PDL1 pathway while simultaneously targeting the 4-1BB co-stimulatory pathway. The presence of both antibodies on the particle surface is more effective at inducing CD8 cell stimulation than either antibody alone which confirmed previous data on the combination of soluble antibodies against these pathways.

However, immunoswitch particles also enhance CD8 cell activation and delay tumor growth as compared to an equivalent amount of soluble anti-PDL1 and anti-4-1BB antibody both in vitro and in vivo. Tethering the antibodies to a rigid particle platform increases avidity for their ligand and may result in increased binding. While higher avidity of the antibodies for their receptor may play a role in the increased efficacy of immunoswitch particles, we identified at least two additional mechanisms that demonstrate that immunoswitch-based CD8 activation is not caused by avidity alone.

Combining both immunosuppressive targeting and co-stimulatory targeting agents (e.g., anti-PDL1 and anti-4-1BB monoclonal antibodies) on a single platform physically links the effector and target cells and may result in switching off and on their respective signaling pathways. This was directly shown in vitro by confocal microscopy and flow cytometry. The physical link is also important in vivo despite the complexity of the tumor microenvironment. This was assessed by comparing tumor control in mice treated with immunoswitch particles or a co-injection of anti-4-1BB mAb only particles and anti-PDL1 mAb only particles—if the physical link between effector and target cells did not play a role, both treatments should work equivalently. Indeed, only immunoswitch particles were able to control tumor growth at the dose studied, indicating that it is not only the fact that the antibodies are bound to a rigid nanoparticle that leads to their efficacy. Additionally, we showed that the nanoparticles, being larger than soluble antibody, diffuse from the injection site more slowly than their soluble counterpart. When injected intratumorally, this means a higher local concentration of the bio-active particles integrated over time and consequently a decreased concentration at off-target sites.

The immunoswitch platform was also shown to be signal 1 dependent, although a priori knowledge of the tumor antigen to target is not necessary—the signal 1 is derived from the tumor cell itself. This was demonstrated in vitro where transgenic 2C CD8 cells were not stimulated by immunoswitch particles in the presence of non-cognate target cells. Thus, immunoswitch particles have the additional benefit to be able to activate a polyclonal T cell response and reduce the chance of antigenic escape, a common fear in targeted immunotherapies. Accordingly, in some aspects the presently disclosed immunoswitch nanoparticles can be used to target patient-specific neoantigens without knowing the neoantigenic determinants of those neoantigens.

In vivo, tumor growth is delayed in mice with established B16-SIY tumors when given immunoswitch particle treatment intratumorally while no anti-tumor effect is evident with the same amount of soluble antibody. This effect is not due to the nanoparticles themselves, as isotype particles also had no anti-tumor effect. Soluble antibody likely had no effect because the doses studied were nearly 100-fold less total antibody than is typically used for treatment when soluble antibody is injected intraperitoneally. Accordingly, in some aspects the presently disclosed immunoswitch nanoparticles can be administered at doses that are significantly less than is typically used for treatment when checkpoint blockade antibodies are administered individually in combination.

Tumor control and extended survival was observed both in the presence and absence of adoptively transferred tumor-specific CD8 cells. Because tumor growth was also delayed in the absence of adoptive transfer, we sought to define the T cell subset responsible for the effect. We showed that CD8 cells, but not CD4 cells, increased in density within the tumor microenvironment of immunoswitch treated mice.

Additionally, CD8 cells within the tumor draining lymph nodes had a higher specificity for the KbSIY tumor antigen after immunoswitch treatment. Thus, it was evident that immunoswitch particles exert their effect on CD8 cells by increasing cell density and specificity for tumor cells. Even in the absence of adoptive transfer, immunoswitch treatment significantly increased the specificity of endogenous CD8 cells for tumor antigens. Finally, immunoswitch treatment efficacy is not specific to the B16 melanoma cell line or the KbSIY peptide-MHC complex—even greater tumor control was evident when evaluated in an MC38-OVA colon cancer tumor model. Again, tumor growth was significantly delayed and survival extended in the absence of any adoptive transfer, indicating that immunoswitch particles can activate the endogenous T cell repertoire against a variety of tumor antigens.

This novel approach to combination therapy results in a single, all-encompassing injectable therapeutic for immunotherapy, including immunotherapy for treating cancer and chronic viral infections. By decreasing the effective antibody dose and combining therapies on a single platform, the presently disclosed immunoswitch nanoparticles can reduce cost and complexity of a multi-faceted cancer and viral immunotherapy treatment.

Additionally, the presently disclosed subject matter has shown proof of concept of a novel "signal-switching" approach that links two signaling pathways. This type of approach can be extended to other inhibitory-to-stimulatory pathways, such as Lag-3, CTLA-4, or anti-CD28. Our data shows the applicability of a new type of combination therapy and builds a framework for further mechanistic studies and extensions on a novel platform.

I. Methods for Converting Immune Inhibitory Signals into Immune Stimulatory Signals Aspects of the presently disclosed subject matter relate to using the presently disclosed immunoswitch particles to convert immune inhibitory signals into immune stimulatory signals.

In an aspect, the presently disclosed subject matter provides a method of converting an immune inhibitory signal in a cell, tissue, or subject into an immune stimulatory signal in the cell, tissue, or subject, comprising administering an effective amount of a presently disclosed immunoswitch particle to the cell, tissue, or subject, wherein the immunoswitch particle targets an immunosuppressive pathway in the cell or tissue of the subject and simultaneously targets a T cell co-stimulatory or T-cell co-inhibitory pathway in the subject, thereby converting an immune inhibitory signal in the cell, tissue, or subject into an immune stimulatory signal.

In some embodiments, the immunoswitch particle targets an immunosuppressive pathway in the cell or tissue and simultaneously targets a T cell co-stimulatory pathway in the subject. In some embodiments, the immunoswitch particle targets an immunosuppressive pathway in the cell or tissue and simultaneously targets a T cell co-inhibitory pathway in the subject. In some embodiments, the immunoswitch particle targets an immunosuppressive pathway in the cell or tissue and simultaneously targets a T cell co-inhibitory pathway and a T cell co-stimulatory pathway in the subject. It should be appreciated that multiple immunosuppressive pathways in a cell or tissue can be simultaneously targeted together with multiple T cell co-inhibitory and/or multiple T cell co-stimulatory pathways. For example, at least one, at least two, or at least three immunosuppressive pathways in a cell or tissue can be simultaneously targeted together with at least one, at least two, or at least three T cell co-inhibitory and/or T cell co-stimulatory pathways.

The presently disclosed subject matter contemplates converting immune inhibitory signals into immune stimulatory signals in any cell or tissue in which such conversion is desired. In some embodiments, the cell or tissue comprises a tumor cell or tumor. In some embodiments, the cell comprises a non-tumor cell in the tumor microenvironment which expresses an immunosuppressive molecule that is induced by a tumor cell in the tumor microenvironment. In some embodiments, the cell or tissue comprises a virus infected cell or tissue. In some embodiments, the cell or tissue comprises a non-virus infected cell in the microenvironment surrounding the virus infected cell that expresses an immunosuppressive molecule that is induced by the virus infected cell. In some embodiments, an immune inhibitor signal in or originating from a tumor microenvironment is converted into an immune stimulatory signal in the tumor microenvironment. In some embodiments, an immune inhibitor signal in or originating from a virus infected cell is converted into an immune stimulatory signal.

In some embodiments, the tumor cell comprises a melanoma tumor cell or cell line. In some embodiments, the tumor cell comprises a colon cancer tumor cell or cell line. In some embodiments, the T cell is a CD8+ T cell.

II. Immunotherapy Methods for Treating Cancer

Aspects of the presently disclosed subject matter relate to using the presently disclosed immunoswitch particles as an immunotherapy for the treatment of cancer.

In an aspect, the presently disclosed subject matter provides an immunotherapy method of treating a cancer in a subject in need thereof comprising administering an effective amount of a presently disclosed immunoswitch particle to the subject, thereby simultaneously targeting in the subject an immunosuppressive pathway in tumor cells or immunosuppressive molecules induced by the tumor in the tumor microenvironment and a co-stimulatory pathway in T cells, thereby enhancing the subject's immune system and treating the cancer in the subject. It is believed that targeting the immunosuppressive pathway in tumor cells or immunosuppressive molecules induced by the tumor in the tumor microenvironment and the co-stimulatory pathway in T cells blocks, switches off, or weakens the immunosuppressive ability of the tumor cells (and/or the immunosuppressive molecules induced by the tumor in the tumor microenvironment) while simultaneously activating, switching on, or magnifying the ability of T cells to target tumors and inhibit their growth.

Those skilled in the art will appreciate that the immunoswitch particles may target immunosuppressive pathways in tumor cells, for example, by targeting the immunosuppressive molecules expressed on the surface of those tumor cells, or immunosuppressive pathways activated via immunosuppressive molecules induced by the tumor in the tumor microenvironment, for example, by targeting the immunosuppressive molecules expressed on non-tumor cells in the tumor microenvironment, such as dendritic cells (e.g., plasmacytoid dendritic cells). Examples of other non-tumor cells in the tumor microenvironment on which the immunosuppressive molecules could be expressed are known in the art (see, e.g., Gajewski et al. 2013).

In another aspect, the presently disclosed subject matter provides an immunotherapy method of treating a cancer in a subject in need thereof comprising administering an effective amount of a presently disclosed immunoswitch particle to the subject, thereby simultaneously targeting in the subject an immunosuppressive pathway in tumor cells or immunosuppressive molecules induced by the tumor in the tumor microenvironment and a co-inhibitory pathway in T cells, thereby enhancing the subject's immune system and treating the cancer in the subject. It is believed that targeting the immunosuppressive pathway in tumor cells or immunosuppressive molecules induced by the tumor in the tumor microenvironment and the co-inhibitory pathway in T cells blocks, switches off, or weakens the immunosuppressive ability of the tumor cells while simultaneously preventing the deactivation, switching off, and/or weakening of the ability of T cells to target tumors and inhibit their growth.

In some embodiments, an immunotherapy method of treating a cancer in a subject in need thereof comprises administering an effective amount of a presently disclosed immunoswitch particle to the subject, thereby simultaneously targeting in the subject an immunosuppressive pathway in tumor cells or immunosuppressive molecules induced by the tumor in the tumor microenvironment and both a co-inhibitory and a co-stimulatory pathway in T cells, thereby enhancing the subject's immune system and treating the cancer in the subject.

In some embodiments, the presently disclosed method for treating cancer comprises administering multiple immunoswitch nanoparticles, e.g., at least one, at least two, or at least three immunoswitch nanoparticles to a subject in need of treatment for a cancer. In such embodiments, each immunoswitch nanoparticle can target different immunosuppressive pathways and T cell co-stimulatory and/or co-inhibitory pathways. In some embodiments, the presently disclosed method for treating cancer comprises administering an immunoswitch nanoparticle that targets multiple immunosuppressive pathways in tumor cells or immunosuppressive molecules induced by the tumor cells in the microenvironment in which the tumor cells reside while simultaneously targeting multiple T cell co-stimulatory and/or co-inhibitory pathways.

As used herein, "target", "targeting" and the like, refer to bringing an agent (e.g., antibody conjugated to an immunoswitch nanoparticle) that has affinity for a cell-surface expressed molecule (e.g., immune checkpoint protein) into sufficient proximity, alignment, and/or conformation with the cell-surface expressed molecule to interfere with a signaling pathway in which the cell-surface expressed molecule is involved. An agent that targets an immunosuppressive pathway, for example, may bind to the cell-surface expressed molecule (e.g., immune checkpoint co-inhibitory receptor), however, binding is not required as long as the agent is in sufficient proximity, alignment, and/or conformation with the cell-surface expressed molecule to interfere with the signaling pathway. It is to be understood that the agents that target the immunosuppressive pathways and/or T cell co-inhibitory or co-stimulatory pathways may switch off or on the respective pathways alone or in combination with the nanoparticle itself. The agents and/or the nanoparticle may directly or indirectly target the immunosuppressive pathways and/or T cell co-inhibitory or co-stimulatory pathways, for example, by virtue of their direct proximity, alignment, and/or conformation with respect to the cell-surface expressed molecules or by virtue of their proximity, alignment and/or conformation with respect to another molecule that is itself brought into sufficient proximity, alignment and/or conformation with the cell-surface expressed molecule to interfere with the signaling pathway. The agents (e.g., antibodies) can be conjugated to nanoparticles by various means well-known in the art, including adsorption and covalent coupling. In some embodiments, the agents (e.g., antibodies) are conjugated to the nanoparticles via a linker. Examples of suitable linkers of use herein include, without limitation, organic linkers, peptide linkers (e.g., small and functional peptide linkers), heterofunctional linkers, bifunctional cross-linkers, etc. (see, e.g., Arruebo et al. 2009).

As used herein, "immunotherapy" in the context of cancer refers to ameliorating, treating, or preventing a malignancy e.g., cancer in a subject (e.g., human), for example, by assisting or boosting the subject's immune system in eradicating cancerous cells. As used herein, the term "treating" in the context of cancer can include reversing, alleviating, inhibiting the progression of, preventing or reducing the likelihood of the disease, disorder, or condition to which such term applies, or one or more symptoms or manifestations of such disease, disorder or condition (e.g., cancer).

The immunotherapy method can delay and/or reverse growth of a subject's tumor compared to growth of the subject's tumor in the absence of administration of the immunoswitch particle. For example, the method can delay growth of the subject's tumor by at least 5%, 10%, 15%, 20%, 25%, 30%, 33%, 35%, 40%, 45%, 50%, 55%, 60%, 66%, 70%, 75%, 80%, 85%, 90%, 91%, 92%, 93%, 94%, 95%, 96%, 97%, 98%, 99% or more as compared to growth of the subject's tumor in the absence of administration of the immunoswitch particle. In some embodiments, the method can delay and/or reverse growth of the subject's tumor by at least 5%, 10%, 15%, 20%, 25%, 30%, 33%, 35%, 40%, 45%, 50%, 55%, 60%, 66%, 70%, 75%, 80%, 85%, 90%, 91%, 92%, 93%, 94%, 95%, 96%, 97%, 98%, 99% or more as compared to growth of the subject's tumor when the first and second agents are administered individually and not conjugated to a nanoparticle.

The immunotherapy method can also extend the length of survival of the subject compared to length of survival of the subject in the absence of administration of the immunoswitch particle. For example, the immunotherapy method can extend survival (e.g., progression free survival, disease free survival, overall survival, etc.) of the subject by 5%, 10%, 15%, 20%, 25%, 30%, 33%, 35%, 40%, 45%, 50%, 55%, 60%, 66%, 70%, 75%, 80%, 85%, 90%, 91%, 92%, 93%, 94%, 95%, 96%, 97%, 98%, 99%, 1-fold, 1.1-fold, 1.2-fold, 1.3-fold, 1.4-fold, 1.5-fold, 1.6-fold, 1.7-fold, 1.8-fold, 1.9-fold, 2.0 fold, 2.5-fold, 3.0-fold, 3.5-fold, 4.0-fold, 5.0-fold, 6-fold, 7-fold, 8-fold, 9-fold, 10-fold, or more as compared to survival of the subject in the absence of administration of the immunoswitch particle. In some embodiments, the immunotherapy method can extend survival (e.g., progression free survival, disease free survival, overall survival, etc.) of the subject by 5%, 10%, 15%, 20%, 25%, 30%, 33%, 35%, 40%, 45%, 50%, 55%, 60%, 66%, 70%, 75%, 80%, 85%, 90%, 91%, 92%, 93%, 94%, 95%, 96%, 97%, 98%, 99%, 1-fold, 1.1-fold, 1.2-fold, 1.3-fold, 1.4-fold, 1.5-fold, 1.6-fold, 1.7-fold, 1.8-fold, 1.9-fold, 2.0 fold, 2.5-fold, 3.0-fold, 3.5-fold, 4.0-fold, 5.0-fold, 6-fold, 7-fold, 8-fold, 9-fold, 10-fold, or more as compared to survival of the subject when the first and second agents are administered to the subject individually and not conjugated to a nanoparticle.

A "cancer" in a subject refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells. Cancer as used herein includes newly diagnosed or recurrent cancers, including without limitation, blastomas, carcinomas, gliomas, leukemias, lymphomas, melanomas, myeloma, and sarcomas. Cancer as used herein includes, but is not limited to, head cancer, neck cancer, head and neck cancer, lung cancer, breast cancer, prostate cancer, colorectal cancer, esophageal cancer, stomach cancer, leukemia/lymphoma, uterine cancer, skin cancer, endocrine cancer, urinary cancer, pancreatic cancer, gastrointestinal cancer, ovarian cancer, cervical cancer, and adenomas. In some embodiments, the cancer comprises Stage 0 cancer. In some embodiments, the cancer comprises Stage I cancer. In some embodiments, the cancer comprises Stage II cancer. In some embodiments, the cancer comprises Stage III cancer. In some embodiments, the cancer comprises Stage IV cancer. In some embodiments, the cancer is refractory and/or metastatic. For example, the cancer may be refractory to treatment with radiotherapy, chemotherapy, photodynamic therapy, proton therapy, surgery, or immunotherapy using soluble antibodies.

In some embodiments, the cancer is melanoma. In some embodiments, the cancer is colon cancer.

A "tumor," as used herein, refers to all neoplastic cell growth and proliferation, whether malignant or benign, and all precancerous and cancerous cells and tissues. A "solid tumor", as used herein, is an abnormal mass of tissue that generally does not contain cysts or liquid areas. A solid tumor may be in the brain, colon, breasts, prostate, liver, kidneys, lungs, esophagus, head and neck, ovaries, cervix, stomach, colon, rectum, bladder, uterus, testes, and pancreas, as non-limiting examples. In some embodiments, the solid tumor regresses or its growth is slowed or arrested after the solid tumor is treated with the presently disclosed methods. In other embodiments, the solid tumor is malignant.

The terms "subject" and "patient" are used interchangeably herein. The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease.

In some embodiments, the subject is selected for treatment with the immunotherapy method. In some embodiments, the subject is one who has been diagnosed with, or is at risk of developing cancer (e.g., melanoma, colon cancer, etc.). In some embodiments, the subject has failed to respond to chemotherapy. In some embodiments, the subject has failed to respond to radiotherapy. In some embodiments, the subject has failed to respond to respond to photodynamic therapy. In some embodiments, the subject has failed to respond to proton therapy.

The presently disclosed subject matter contemplates any mode of administering the presently disclosed immunoswitch particles to subjects in need of immunotherapy treatment. In some embodiments, administration of the immunoswitch particle to the subject comprises intratumoral injection.

The presently disclosed subject matter further contemplates administering the immunoswitch particle in combination with additional therapies and/or agents. Examples of combination therapies include, without limitation, co-administration of anti-inflammatory agents, biological adjuvants (e.g., interleukins, cytokines, *Bacillus* Comette-Guerin, monophosphoryl lipid A, etc.), chemotherapy, radiotherapy, photodynamic therapy, proton therapy and/or surgery. In some embodiments, the method includes administering a vaccine that works by activating the immune system to prevent or destroy cancer cell growth.

As used herein, "chemotherapy" is used to connote a compound or composition that is administered in the treatment of cancer. Chemotherapy includes, but is not limited to, alkylating agents, such as thiotepa and cyclophosphamide; alkyl sulfonates, such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas, such as carmustine, chlorozotocin, fotemustine, lomustine, nimustine, ranimustine; antibiotics, such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimidine analogs, such as ancitabine, azacitidine, 6-azauridine, carmofur, cytosine arabinoside, dideoxyuridine, doxifluridine, enocitabine, floxuridine, 5-FU; androgens, such as calusterone, dromostanolone propionate, epitiostanol, mepitiostane, testolactone; anti-adrenals, such as aminoglutethimide, mitotane, trilostane; folic acid replenishers, such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g., paclitaxel and docetaxel; chlorambucil; gemcitabine; 6-thioguanine; mercaptopurine; platinum analogs, such as cisplatin and carboplatin; vinblastine; platinum; etoposide; ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine; retinoic acid; esperamicins; capecitabine; and pharmaceutically acceptable salts, acids or derivatives of any of the above.

Chemotherapy also includes anti-hormonal agents that act to regulate or inhibit hormone action on tumors, such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, and goserelin; and pharmaceutically acceptable salts, acids or derivatives of any of the above.

In some embodiments, the chemotherapy is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide, and irinotecan, as well as pharmaceutically acceptable salts, acids, or derivatives of any of these.

In some embodiments, the chemotherapy is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these.

In certain embodiments, the chemotherapy is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain alternative embodiments, the antimitotic agent comprises a *vinca* alkaloid, such as vincristine, vinblastine, vinorelbine, or vindesine, or pharmaceutically acceptable salts, acids, or derivatives thereof.

As used herein, "radiotherapy" refers to those agents conventionally adopted in the therapeutic field of cancer treatment and includes photons having enough energy for chemical bond ionization such as, for instance, alpha (a), beta 03), and gamma (γ) rays from radioactive nuclei as well as x-rays. The radiation may be high-LET (linear energy transfer) or low-LET. LET is the energy transferred per unit length of the distance. High LET is said to be densely ionizing radiation and Low LET is said to be sparsely ionizing radiation. Representative examples of high-LET are neutrons and alpha particles. Representative examples of low-LET are x-ray and gamma rays. Low LET radiation including both x-rays and γ-rays is most commonly used for radiotherapy of cancer patients. The radiation may be used for external radiation therapy that is usually given on an outpatient basis or for internal radiation therapy that uses radiation that is placed very close to or inside the tumor. In case of internal radiation therapy, the radiation source is usually sealed in a small holder called an implant. Implants may be in the form of thin wires, plastic tubes called catheters, ribbons, capsules, or seeds. The implant is put directly into the body. Internal radiation therapy may require a hospital stay. The ionizing radiation source is provided as a unit dose of radiation and is preferably an x-ray tube since it provides many advantages, such as convenient adjustable dosing where the source may be easily turned on and off, minimal disposal problems, and the like. A unit dose of radiation is generally measured in gray (Gy). The ionizing radiation source may also comprise a radioisotope, such as a solid radioisotopic source (e.g., wire, strip, pellet, seed, bead, or the like), or a liquid radioisotopic filled balloon. In the latter case, the balloon has been specially configured to prevent leakage of the radioisotopic material from the balloon into the body lumen or blood stream. Still further, the ionizing radiation source may comprise a receptacle in the catheter body for receiving radioisotopic materials like pellets or liquids. The radioisotopic material may be selected to emit α, β and γ. Usually, α and β radiations are preferred since they may be quickly absorbed by the surrounding tissue and will not penetrate substantially beyond the wall of the body lumen being treated. Accordingly, incidental irradiation of the heart and other organs adjacent to the treatment region can be substantially eliminated. The total number of units provided will be an amount determined to be therapeutically effective by one skilled in treatment using ionizing radiation. This amount will vary with the subject and the type of malignancy or neoplasm being treated. The amount may vary but a patient may receive a dosage of about 30-75 Gy over several weeks.

Radiotherapy includes factors that cause DNA damage, such as γ-rays, X-rays, and/or the directed delivery of radioisotopes to tumor cells. Other forms of DNA damaging factors are also contemplated such as microwaves and UV-irradiation. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the target cell. In some embodiments, the radiotherapeutic agent is selected from the group consisting of $^{47}$Sc, $^{67}$Cu, $^{90}$Y, $^{109}$Pd, $^{123}$I, $^{125}$I, $^{131}$I, $^{186}$Re, $^{188}$Re, $^{199}$Au, $^{211}$At, $^{212}$Pb, $^{212}$B, $^{32}$P and $^{33}$P, $^{71}$Ge, $^{77}$As, $^{103}$Pb, $^{105}$Rh, $^{111}$Ag, $^{119}$Sb, $^{121}$Sn, $^{131}$Cs, $^{143}$Pr, $^{161}$Tb $^{177}$Lu, $^{191}$Os, $^{193}$MPt, $^{197}$H, $^{43}$K, $^{52}$Fe, $^{57}$Co, $^{67}$Cu, $^{67}$Ga, $^{68}$Ga, $^{77}$Br, $^{81}$Rb/.$^{81}$MKr, $^{87}$MSr, $^{99}$MTc, $^{111}$In, $^{113}$MIn, $^{127}$Cs, $^{129}$Cs, $^{132}$I, $^{197}$Hg, $^{203}$Pb and $^{206}$Bi, as described in U.S. Pat. No. 8,946,168, the entirety of which is incorporated herein by reference.

As used herein, "photodynamic therapy", also known as photoradiation therapy, phototherapy, and photochemotherapy, refers to a treatment that uses photosensitizing agents in combination with light to kill cancer cells. The photosensitizing agents kill cancer cells upon light activation.

As used herein, "proton therapy", also known as proton beam therapy, refers to a treatment that uses a beam of protons to irradiate and kill cancer cells.

As used herein, "anti-inflammatory agent" refers to an agent that may be used to prevent or reduce an inflammatory response or inflammation in a cell, tissue, organ, or subject. Exemplary anti-inflammatory agents contemplated for use include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecrolimus, prodrugs thereof, co-drugs thereof, and combinations thereof. The anti-inflammatory agent may also be a biological inhibitor of proinflammatory signaling molecules including antibodies to such biological inflammatory signaling molecules.

III. Immunotherapy Methods for Treating Chronic Viral Infections

Aspects of the presently disclosed subject matter relate to using the presently disclosed immunoswitch particles as an immunotherapy for the treatment of chronic viral infections.

In an aspect, the presently disclosed subject matter provides an immunotherapy method of treating a chronic viral infection in a subject in need thereof comprising administering an effective amount of a presently disclosed immunoswitch particle to the subject, thereby simultaneously targeting in the subject an immunosuppressive pathway in virus infected cells or an immunosuppressive molecule induced by the virus infected cell in the microenvironment surrounding the virus infected cell, and a co-stimulatory pathway in T cells in the subject, thereby enhancing the subject's immune system and treating the chronic viral infection in the subject. It is believed that targeting the immunosuppressive pathway in virus infected cells and/or immunosuppressive molecules induced by the virus infected cells in the microenvironment surrounding the virus infected cells, and the co-stimulatory pathway in T cells blocks, switches off, or weakens the immunosuppressive ability of the virus infected cells while simultaneously activating, switching on, or magnifying the ability of T cells to target viruses and inhibit viral infection.

Those skilled in the art will appreciate that the immunoswitch particles may target immunosuppressive pathways in virus infected cells, for example, by targeting the immunosuppressive molecules expressed on the surface of those virus infected cells, or immunosuppressive pathways activated via immunosuppressive molecules induced by the virus infected cells in the microenvironment surrounding the virus infected cells, for example, by targeting the immunosuppressive molecules expressed on non-tumor cells in the virus infected cell microenvironment, such as dendritic cells (e.g., plasmacytoid dendritic cells). The role of plasmacytoid dendritic cells in the immune response against viral infection has been described (see, e.g., Mathan et al. 2013). Examples of other non-viral infected cells in the virus infected cell microenvironment on which the immunosuppressive molecules could be expressed are known in the art (see, e.g., De Paoli et al. 2015).

In another aspect, the presently disclosed subject matter provides an immunotherapy method of treating a chronic viral infection in a subject in need thereof comprising administering an effective amount of a presently disclosed immunoswitch particle to the subject, thereby simultaneously targeting in the subject an immunosuppressive pathway in virus infected cells or an immunosuppressive molecule induced by the virus infected cell in the microenvironment surrounding the virus infected cell, and a co-inhibitory pathway in T cells, thereby enhancing the subject's immune system and treating the chronic viral infection in the subject. It is believed that targeting the immunosuppressive pathway in virus infected cells and/or immunosuppressive molecules induced by the virus infected cells in the microenvironment surrounding the virus infected cells, and the co-inhibitory pathway in T cells blocks, switches off, or weakens the immunosuppressive ability of the virus infected cells while simultaneously preventing the deactivation, switching off, and/or weakening of the ability of T cells to target viruses and inhibit viral infection.

In some embodiments, an immunotherapy method of treating a chronic viral infection in a subject in need thereof comprises administering an effective amount of a presently disclosed immunoswitch particle to the subject, thereby simultaneously targeting in the subject an immunosuppressive pathway in virus infected cells or an immunosuppressive molecule induced by the virus infected cell in the microenvironment surrounding the virus infected cell, and both a co-inhibitory and a co-stimulatory pathway in T cells, thereby enhancing the subject's immune system and treating the chronic viral infection in the subject.

As used herein, "immunotherapy" in the context of a chronic viral infection refers to ameliorating, treating, or preventing chronic viral infection in a subject (e.g., human), for example, by assisting or boosting the subject's immune system in inhibiting viral infection and/or replication. As used herein, the term "treating" in the context of a chronic viral infection can include reversing, alleviating, inhibiting the progression of, preventing or reducing the likelihood of the disease, disorder, or condition to which such term applies, or one or more symptoms or manifestations of such disease, disorder or condition (e.g., chronic viral infection). As used herein, the phrase "treating a chronic viral infection" encompasses treating diseases, disorders, and conditions associated with the chronic viral infection. One non-limiting example of a disease, condition, or disorder associated with a viral infection is acquired immune deficiency syndrome (AIDS), which is associated with infection by the human immunodeficiency virus (HIV). In some embodiments, the presently disclosed immunoswitch particles can be used to treat a cancer associated with a chronic viral infection, such as a lymphoma (e.g., non-Hodgkin's lymphoma) associated with a chronical viral infection (e.g., Epstein Barr virus (EBV), Kaposi's sarcoma herpesvirus (KSHV), human immunodeficiency virus type 1 (HIV-1), and human hepatitis C virus (HCV).

In some embodiments, the presently disclosed method for treating a chronic viral infection comprises administering multiple immunoswitch nanoparticles, e.g., at least one, at least two, or at least three immunoswitch nanoparticles to a subject in need of treatment for a chronic viral infection. In such embodiments, each immunoswitch nanoparticle can target different immunosuppressive pathways and T cell co-stimulatory and/or co-inhibitory pathways. In some embodiments, the presently disclosed method for treating a chronic viral infection comprises administering an immunoswitch nanoparticle that targets multiple immunosuppressive pathways in virus infected cells while simultaneously targeting multiple T cell co-stimulatory and/or co-inhibitory pathways.

The immunotherapy method can inhibit multiplicity of infection of the virus infected cells compared to multiplicity of infection of the virus infected cells in the absence of administration of the immunoswitch particle. For example, the method can inhibit multiplicity of infection of virus infected cells in the subject by at least 5%, 10%, 15%, 20%, 25%, 30%, 33%, 35%, 40%, 45%, 50%, 55%, 60%, 66%, 70%, 75%, 80%, 85%, 90%, 91%, 92%, 93%, 94%, 95%, 96%, 97%, 98%, 99% or more as compared to the multiplicity of infection of virus infected cells in the subject in the absence of administration of the immunoswitch particle. In some embodiments, the method can inhibit multiplicity of infection of the virus infected cells by at least 5%, 10%, 15%, 20%, 25%, 30%, 33%, 35%, 40%, 45%, 50%, 55%, 60%, 66%, 70%, 75%, 80%, 85%, 90%, 91%, 92%, 93%, 94%, 95%, 96%, 97%, 98%, 99% or more as compared to multiplicity of infection of the virus infected cells when the first and second agents are administered individually and not conjugated to a nanoparticle.

The immunotherapy method can also extend the latency of the virus in the subject compared to latency of the virus in the subject in the absence of administration of the immunoswitch particle. For example, the immunotherapy method can extend the latency of the virus in the subject by 5%, 10%, 15%, 20%, 25%, 30%, 33%, 35%, 40%, 45%, 50%, 55%, 60%, 66%, 70%, 75%, 80%, 85%, 90%, 91%, 92%, 93%, 94%, 95%, 96%, 97%, 98%, 99%, 1-fold, 1.1-fold, 1.2-fold, 1.3-fold, 1.4-fold, 1.5-fold, 1.6-fold, 1.7-fold, 1.8-fold, 1.9-fold, 2.0 fold, 2.5-fold, 3.0-fold, 3.5-fold, 4.0-fold, 5.0-fold, 6-fold, 7-fold, 8-fold, 9-fold, 10-fold, or more as compared to the latency of the virus in the subject in the absence of administration of the immunoswitch particle. In some embodiments, the immunotherapy method can extend latency of the virus in the subject by 5%, 10%, 15%, 20%, 25%, 30%, 33%, 35%, 40%, 45%, 50%, 55%, 60%, 66%, 70%, 75%, 80%, 85%, 90%, 91%, 92%, 93%, 94%, 95%, 96%, 97%, 98%, 99%, 1-fold, 1.1-fold, 1.2-fold, 1.3-fold, 1.4-fold, 1.5-fold, 1.6-fold, 1.7-fold, 1.8-fold, 1.9-fold, 2.0 fold, 2.5-fold, 3.0-fold, 3.5-fold, 4.0-fold, 5.0-fold, 6-fold, 7-fold, 8-fold, 9-fold, 10-fold, or more as compared to latency of the virus in the subject when the first and second agents are administered to the subject individually and not conjugated to a nanoparticle.

An "infection" refers to the colonization of a cell or multicellular organism (host) by a microorganism such as a virus. The process of infection encompasses invasion (entry of the virus into one or more cell(s)) and, if the infection proceeds, later steps in the viral life cycle, typically resulting in multiplication of the virus and, detrimental effects of the virus on the host. A viral infection includes any condition in which the presence of one or more virus population(s) is harmful to a host cell or organism. The term "infection" encompasses excessive replication of viruses that are normally present in a subject, or the presence and, optionally, replication, of viruses that are not normally present in the subject.

As used herein, "chronic viral infection" is meant a viral infection of humans or other animals which is able to infect a host and reproduce within the cells of a host over a prolonged period of time-usually weeks, months or years, without proving fatal. Amongst viruses giving rise to chronic infections and which may be treated in accordance with the presently disclosed subject matter are the human papilloma viruses (HPV), Herpes simplex and other herpes viruses, the viruses of hepatitis B and C (HBV and HCV) as well as other hepatitis viruses, the measles virus, all of which can produce important clinical diseases, and HIV. Prolonged infection may ultimately lead to the induction of disease which may be, e. g. in the case of hepatitis C virus liver cancer, fatal to the patient. Other chronic viral infections which may be treated in accordance with the present invention include Epstein Barr virus (EBV), as well as other viruses such as those which may be associated with tumors, or in the case of animals, various veterinary viral diseases, for example those of domestic pets or farmyard animals important in agriculture. In some embodiments, the chronic viral infection comprises a Kaposi's sarcoma herpesvirus (KSHV) infection.

In some embodiments, the chronic viral infection is HIV. In some embodiments, the chronic viral infection is HPV. In some embodiments, the chronic viral infection is HBV. In some embodiments, the chronic viral infection is HCV. In some embodiments, the chronic viral infection is Herpes simplex virus.

In some embodiments, the subject is selected for treatment with the immunotherapy method. In some embodiments, the subject is one who has been diagnosed with, or is at risk of developing a chronic viral infection (e.g., HIV, HPV, HBV, HCV, etc.). In some embodiments, the subject has failed to respond to anti-viral therapy. In some embodiments, the subject has failed to respond to anti-retroviral therapy. In some embodiments, the subject has failed to respond to respond to CAR-T therapy. In some embodiments, the subject has failed to respond to combination anti-viral therapy.

The presently disclosed subject matter further contemplates administering the immunoswitch particle in combination with additional therapies and/or agents. Examples of combination therapies for treating chronic viral infections include, without limitation, co-administration of antiviral agents, adjuvants, and combinations thereof.

Exemplary classes of antiviral agents of use herein include, without limitation, antiviral boosters, antiviral combinations, antiviral interferons, chemokine receptor antagonists, integrase strand transfer inhibitors, NNRTIs, NSSA inhibitors, nucleoside reverse transcriptase inhibitors (NRTIs), protease inhibitors, and purine nucleosides.

Examples of antirival boosters of use herein include, without limitation, ritonavir, cobicistat, and combinations thereof.

Examples of antiviral combinations of use herein include, without limitation, abacavir and lamivudine (EPZICOM), cobicistat/elvitegravir/emtricitabine/tenofovir (STRIBILD), emtricitabine/tenofovir (TRUVADA), efavirenz/emtricitabine/tenofovir (ATRIPLA), ledipasvir/sofosbuvir (HARVONI), abacavir/lamivudine/zidovudine (TRIZIVIR), emtricitabine/rilpivirine/tenofovir (COMPLERA), abacavir/dolutegravir/lamivudine (TRIUMEQ), dasabuvir/ombitasvir/paritaprevir/ritonavir (VIEKIRA PAK), elbasvir/grazoprevir (ZEPATIER), lamivudine/zidovudine (COMBIVIR), cobicistat/elvitegravir/emtricitabine/tenofovir alafenamide (GENVOYA), cobicistat/darunavir (PREZCOBIX), emtricitabine/tenofovir, emtricitabine/lopinavir/ritonavir/tenofovir, emtricitabine/nelfinavir/tenofovir, lamivudine/raltegravir (DUTREBIS), atazanavir/cobicistat (EVOTAZ), interferon alfa-2b/ribavirin (REBETRON), ombitasvir/paritaprevir/ritonavir (TECHNIVIE), and combinations thereof.

Examples of antiviral interferons of use herein include, without limitation, peginterferon alfa-2a (PEGASYS), peginterferon alfa-2b (PEGINTRON), peginterferon alfa-2b (SYLATRON), and combinations thereof.

An exemplary chemokine receptor antagonist of use herein is maraviroc (SELZENTRY).

Exemplary integrase strand transfer inhibitors of use herein include, without limitation, raltegravir, dolutegravir, elvitegravir, and combinations thereof.

Exemplary non-nucleoside reverse transcriptase inhibitors (NNRTIs) of use herein include, without limitation, nevirapine, etravirine, efavirenz, rilpivirine, delavirdine, nevirapine and combinations thereof.

An exemplary non-structural protein 5A (NSSA) inhibitor of use herein is daclatasvir (DAKLINZA).

Exemplary nucleoside reverse transcriptase inhibitors (NRTIs) of use herein include, without limitation, entecavir, lamivudine, adefovir, didanosine, tenofovir, abacavir, lamivudine, zidovudine, stavudine, emtricitabine, zalcitabine, telbivudine, didanosine, and combinations thereof.

Exemplary protease inhibitors of use herein include, without limitation, boceprevir, simeprevir, telaprevir, lopinavir/ritonavir (KALETRA), fosamprenavir, darunavir, ritonavir, tipranavir, atazanavir, nelfinavir, amprenavir, indinavir, saquinavir, and combinations thereof.

Exemplary purine nucleoside of use herein include, without limitation, ribavirin, valacyclovir, famciclovir, acyclovir, ganciclovir, valganciclovir, cidofovir and combinations thereof.

Other exemplary antiviral agents of use herein include, without limitation, sofosbuvir, enfuvirtide, enfuvirtide, fomivirsen, and combinations thereof.

IV. Immunoswitch Particles

Aspects of the presently disclosed subject matter relate to immunoswitch particles that can be used to enhance immune responses in cells, tissues, and subjects, for example, by converting immune inhibitory signals into immune stimulatory signal, for example, in the tumor microenvironment to delay and/or reverse tumor growth, or as an immunotherapy for the treatment of cancer alone, or in combination together with conventional cancer treatments. In some aspects, the immunoswitch particles can be used to enhance immune responses in subjects against viral infections, for example, to inhibit viral infection and/or replication, or as an immunotherapy for the treatment of chronic viral infections alone, or in combination together with conventional treatments for chronic viral infections.

In an aspect, the presently disclosed subject matter provides an immunoswitch particle comprising a nanoparticle comprising a first agent that targets an immunosuppressive pathway in a tumor cell or immunosuppressive molecule induced by the tumor cell in the tumor microenvironment, and a second agent that simultaneously targets a co-stimulatory pathway in a T cell.

In an aspect, the presently disclosed subject matter provides an immunoswitch particle comprising a nanoparticle comprising a first agent that targets an immunosuppressive pathway in a tumor cell or immunosuppressive molecule induced by the tumor cell in the tumor microenvironment and a second agent that simultaneously targets a co-inhibitory pathway in a T cell.

In an aspect, the presently disclosed subject matter provides an immunoswitch particle comprising a nanoparticle comprising a first agent that targets an immunosuppressive pathway in a tumor cell or immunosuppressive molecule induced by the tumor cell in the tumor microenvironment, a second agent that simultaneously targets a co-inhibitory pathway and/or a co-stimulatory pathway in a T cell.

In an aspect, the presently disclosed subject matter provides an immunoswitch particle comprising a nanoparticle comprising a first agent that targets an immunosuppressive pathway in a virus infected cell or immunosuppressive molecule induced by the virus infected cell in the microenvironment surrounding the virus infected cell and a second agent that simultaneously targets a co-stimulatory pathway in a T cell.

In some embodiments, the nanoparticle comprises a third agent, a fourth agent, and/or a fifth agent that each targets an immunosuppressive pathway in a tumor cell or immunosuppressive molecule induced by the tumor cell in the tumor microenvironment, and/or a co-inhibitory pathway or co-stimulatory pathway in a T cell.

In an aspect, the presently disclosed subject matter provides an immunoswitch particle comprising a nanoparticle comprising a first agent that targets an immunosuppressive pathway in a virus infected cell or immunosuppressive molecule induced by the virus infected cell in the microenvironment surrounding the virus infected cell, and a second agent that simultaneously targets a co-inhibitory pathway in a T cell.

In an aspect, the presently disclosed subject matter provides an immunoswitch particle comprising a nanoparticle comprising a first agent that targets an immunosuppressive pathway in a virus infected cell or immunosuppressive molecule induced by the virus infected cell in the microenvironment surrounding the virus infected cell, a second agent that simultaneously targets a co-inhibitory pathway and/or a co-stimulatory pathway in a T cell.

In some embodiments, the nanoparticle comprises a third agent, a fourth agent, and/or a fifth agent that each targets an immunosuppressive pathway in a virus infected cell or immunosuppressive molecule induced by the virus infected cell in the microenvironment surrounding the virus infected cell, and/or a co-inhibitory pathway or co-stimulatory pathway in a T cell.

The presently disclosed subject matter contemplates using any nanoparticle that can be functionalized with the first and second agents. Nanoparticles may be synthesized using any method described in the art, or disclosed herein. In certain embodiments, the nanoparticles are modified by polyethylene glycol (PEG) conjugation, a process known in the art as "PEGylation." As used herein, the term "nanoparticle," refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm and all integers and fractional integers in between). In some embodiments, the nanoparticle has at least one dimension, e.g., a diameter, of between about 50 nm and 100 nm. In some embodiments, the nanoparticle has a diameter of about 75 nm. In some embodiments, the nanoparticle has a diameter of about 76 nm. In some embodiments, the nanoparticle has a diameter of about 77 nm. In some embodiments, the nanoparticle has a diameter of about 78 nm. In some embodiments, the nanoparticle has a diameter of about 79 nm. In some embodiments, the nanoparticle has a diameter of about 80 nm. In some embodiments, the nanoparticle has a diameter of about 81 nm. In some embodiments, the nanoparticle has a diameter of about 82 nm. In some embodiments, the nanoparticle has a diameter of about 83 nm. In some embodiments, the nanoparticle has a diameter of about 84 nm. In some embodiments, the nanoparticle has a diameter of about 85 nm. In other embodiments, the nanoparticle has a diameter of about 200 nm, about 300 nm, about 400 nm, about 500 nm, about 600 nm, about 700 nm, about 800 nm, or about 900 nm. In yet other embodiments, the nanoparticle has a diameter of about 1000 nm (1 μm). In such embodiments, the particle also can be referred to as a "microparticle." Thus, the term "microparticle" includes particles having at least one dimension in the range of about one micrometer (μm), i.e., $1 \times 10^{-6}$ meters, to about 1000 μm. The term "particle" as used herein is meant to include nanoparticles and microparticles.

Nanoparticles can be made, for example, out of metals such as iron, nickel, aluminum, copper, zinc, cadmium, titanium, zirconium, tin, lead, chromium, manganese and cobalt; metal oxides and hydrated oxides such as aluminum oxide, chromium oxide, iron oxide, zinc oxide, and cobalt oxide; metal silicates such as of magnesium, aluminum, zinc, lead, chromium, copper, iron, cobalt, and nickel; alloys such as bronze, brass, stainless steel, and so forth. Nanoparticles can also be made of non-metal or organic materials such as cellulose, ceramics, glass, nylon, polystyrene, rubber, plastic, or latex. In some embodiments, nanoparticles comprise a combination of a metal and a non-metal or organic compound, for example, methacrylate- or styrene-coated metals and silicate coated metals. The base material can be doped with an agent to alter its physical or chemical properties. For example, rare earth oxides can be included in aluminosilicate glasses to create a paramagnetic glass materials with high density (see White & Day, Key Engineering Materials Vol. 94-95, 181-208, 1994). In some embodiments, nanoparticles comprise or consist of biodegradable organic materials, such as cellulose, dextran, and the like.

In some embodiments, the nanoparticle comprises a paramagnetic nanoparticle. As used herein, "paramagnetic" as used herein refers to a substance that is generally nonmagnetic under normal circumstances. However, when placed under a magnetic field, the substance possesses magnetization in direct proportion to the strength of the field. In particular embodiments, the nanoparticle comprises a paramagnetic iron-dextran nanoparticle. In particular embodiments, the nanoparticle comprises a paramagnetic iron-dextran nanoparticle having a diameter of between about 50 nm and about 100 nm. In particular embodiments, the nanoparticle comprises a paramagnetic iron-dextran nanoparticle having a diameter of about 80 nm.

The presently disclosed subject matter contemplates using any agent (i.e., first agent) that targets an immunosuppressive pathway in a tumor cell or immunosuppressive molecule induced by the tumor cell in the tumor microenvironment, and/or immunosuppressive cell or immunosuppressive molecule induced by the virus infected cell in the microenvironment surrounding the virus infected cell. Exemplary agents of use herein include, without limitation, small organic molecules (e.g., haptens) or small inorganic molecules; saccharides; oligosaccharides; polysaccharides; a biological macromolecule selected from the group consisting of peptides (e.g., aptides), proteins, peptide analogs and derivatives; peptidomimetics; nucleic acids selected from the group consisting of guide RNAs, miRNAs, siRNAs, shRNAs, antisense nucleic acids, such as antisense RNAs, ribozymes, and aptamers; an extract made from biological materials selected from the group consisting of bacteria, plants, fungi, animal cells, and animal tissues; naturally occurring or synthetic compositions; and any combination thereof.

In some embodiments, the immunosuppressive pathway comprises an inhibitory signal transmitted to an immune cell via an immune checkpoint protein. In some embodiments, the first agent comprises an agent that inhibits an immune checkpoint immune checkpoint protein. Those skilled in the art will appreciate that the first agent can be used to inhibit the immune check point receptor protein in a variety of ways, for example, by modulating the immune checkpoint protein itself or a binding and/or interacting partner of the protein, as long as the agent prevents and/or reduces interaction between the protein and its interacting partner sufficiently to prevent and/or reduce the inhibitory signal being transmitted to the immune cell.

As used herein, the term "reduce" or "inhibit," and grammatical derivations thereof, refers to the ability of an agent to block, partially block, interfere, decrease, reduce or deactivate a biological molecule, pathway or mechanism of action. Thus, one of ordinary skill in the art would appreciate that the term "inhibit" encompasses a complete and/or partial loss of activity, e.g., a loss in activity by at least 10%, in some embodiments, a loss in activity by at least 20%, 30%, 50%, 75%, 95%, 98%, and up to and including 100%.

In particular embodiments, the immune checkpoint protein is PDL1. PDL1 is a ligand for immune checkpoint receptor PD1. PD1 (Programmed Cell Death Protein 1; e.g. GenBank Accession No. NP 005009.2), also known as CD279 (Cluster of Differentiation 279), is a cell surface membrane protein that is expressed mainly on a subset of activated T lymphocytes. In humans, it is encoded by the PDCD1 gene (Entrez Gene GeneID: 5133). PD1 is a member of the immunoglobulin gene superfamily, and has an extracellular region containing immunoglobulin superfamily domain, a transmembrane domain, and an intracellular region including an immunoreceptor tyrosine-based inhibitory motif. PD1 is rapidly induced on the surface of T-cells in response to anti-CD3. PD1 is also induced on the surface of B-cells (in response to anti-IgM) and is expressed on a subset of thymocytes and myeloid cells. Two types of human PD1 ligands have been identified: PDL1 and PD-L2. PD1 ligands comprise a signal sequence, and an IgV domain, an IgC domain, a transmembrane domain, and a short cytoplasmic tail. Both PDL1 (NCBI Reference Sequence: NP_001254635.1) and PDL2 (NCBI Reference Sequence: NP_079515.2) are members of the B7 family of polypeptides.

In particular embodiments, the immune checkpoint protein is PD-L2.

In some embodiments, the first agent comprises a PDL1 antagonist.

In some embodiments, the PDL1 antagonist comprises an aptamer that targets PDL1. Aptamers are single-chained oligonucleotides (e.g., RNA or DNA) exhibiting three-dimensional folding that helps them bind targets with high specificity. Soldevilla et al. recently reviewed the use of aptamers in the context of cancer immunotherapy (Soldevilla et al. 2016).

For example, Prodeus et al. describe the development of aptamers (e.g., DNA aptamers) as synthetic, non-immunogenic agents that specifically bind to the PD-1 extracellular domain and block the PD-1:PDL1 interaction (Prodeus et al. 2015), and in particular they report an aptamer (e.g., MP7) that functionally inhibits in primary T-cells the PDL1-mediated suppression of IL-2 secretion. Further, a PEGylated version of MP7 retained PD-1:PDL1 interaction blocking capability and suppressed growth of PDL1+ colon carcinoma cells. Accordingly, in some embodiments, the PDL1 antagonist comprises an anti-PDL1 aptamer that targets PDL1. In some embodiments, the anti-PDL1 aptamer targets the extracellular domain of PD-1. In some embodiments, the anti-PDL1 aptamer is a PEGylated anti-PDL1 aptamer. In some embodiments, the anti-PDL1 aptamer is a DNA aptamer. In some embodiments, the anti-PDL1 aptamer is MP7. In some embodiments, the anti-PDL1 aptamer is PEGylated MP7. In some embodiments, the anti-PDL1 aptamer is MP5. In some embodiments, the anti-PDL1 aptamer is PEGylated MP5.

In some embodiments, the first agent comprises a PDL1 antagonist antibody, or functional variant thereof, conjugated to the nanoparticle. Examples of anti-PDL1 antibodies of use in the presently disclosed particles, compositions, and methods include, without limitation, BMS-936559, MEDI-4736, and MPDL3280A.

In particular embodiments, the immune checkpoint protein is PD-L2. In some embodiments, the first agent comprises a PDL2 antagonist. In some embodiments, the PDL2 antagonist comprises an aptamer that targets PDL2.

The presently disclosed subject matter contemplates using any agent (i.e., second agent) that targets a co-stimulatory pathway or co-inhibitory in a T cell. Exemplary agents of use herein include, without limitation, small organic molecules (e.g., haptens) or small inorganic molecules; saccharides; oligosaccharides; polysaccharides; a biological macromolecule selected from the group consisting of peptides (e.g., aptides), proteins, peptide analogs and derivatives; peptidomimetics; nucleic acids selected from the group consisting of guide RNAs, miRNAs, siRNAs, shRNAs, antisense nucleic acids, such as antisense RNAs, ribozymes, and aptamers; an extract made from biological materials selected from the group consisting of bacteria, plants, fungi, animal cells, and animal tissues; naturally occurring or synthetic compositions; and any combination thereof.

Non-limiting examples of T cell co-stimulatory pathways of use herein include, for example, the T cell co-stimulatory pathway is selected from the group consisting of the 4-1BB signaling pathway, the CD27 signaling pathway, the CD28 signaling pathway, the ICOS signaling pathway, the CD226 signaling pathway, the CRTAM signaling pathway, the TIM1 signaling pathway, the CD2 signaling pathway, the SLAM signaling pathway, the CD84 signaling pathway, the Ly9 signaling pathway, the Ox40 signaling pathway, and the CRACC signaling pathway.

In some embodiments, the T cell stimulatory pathway comprises the 4-1BB signaling pathway. In such embodiments, the second agent comprises a 4-1BB agonist. 4-1BB agonists have been reviewed recently (see, e.g., Bartkowiak and Curran 2015), and in particular describe agonist antibodies against 4-1BB and aptamers that are of use herein. In some embodiments, the second agent comprises a 4-1BB agonist aptamer. In some embodiments, the second agent comprises a 4-1BB agonist antibody, or a functional variant thereof.

In some embodiments, the T cell stimulatory pathway is the CD27 signaling pathway. In such embodiments, the second agent comprises a CD27 agonist. In some embodiments, the second agent comprises a CD27 agonist antibody or a functional variant thereof. Examples of suitable such antibodies include, without limitation, the agonist anti-human CD27 monoclonal antibodies (see, e.g., He et al. 2013).

In some embodiments, the T cell stimulatory pathway is the CD28 signaling pathway. In such embodiments, the second agent comprises a CD28 agonist. In some embodiments, the second agent comprises a CD28 agonist antibody or a functional variant thereof. Examples of suitable such antibodies include, without limitation, superagonistic anti-CD28 antibodies (see, e.g., Beyersdorf et al. 2005).

In some embodiments, the T cell stimulatory pathway comprises the ICOS signaling pathway. In such embodiments, the second agent comprises a ICOS agonist. In some embodiments, the second agent comprises an ICOS agonist antibody or a functional variant thereof.

In some embodiments, the T cell stimulatory pathway comprises the CD226 signaling pathway. In such embodiments, the second agent comprises a CD226 agonist. In some embodiments, the second agent comprises a CD226 agonist antibody or a functional variant thereof.

In some embodiments, the T cell stimulatory pathway comprises the CRTAM signaling pathway. In such embodiments, the second agent comprises a CRTAM agonist. In some embodiments, the second agent comprises a CRTAM agonist antibody or a functional variant thereof.

In some embodiments, the T cell stimulatory pathway comprises the TIM1 signaling pathway. In such embodiments, the second agent comprises a TIM1 agonist. In some embodiments, the second agent comprises a TIM1 agonist antibody or a functional variant thereof.

In some embodiments, the T cell stimulatory pathway comprises the CD2 signaling pathway. In such embodiments, the second agent comprises a CD2 agonist. In some embodiments, the second agent comprises a CD2 agonist antibody or a functional variant thereof.

In some embodiments, the T cell stimulatory pathway comprises the SLAM signaling pathway. In such embodiments, the second agent comprises a SLAM agonist. In some embodiments, the second agent comprises a SLAM agonist antibody or a functional variant thereof.

In some embodiments, the T cell stimulatory pathway comprises the CD84 signaling pathway. In such embodiments, the second agent comprises a CD84 agonist. In some embodiments, the second agent comprises a CD84 agonist antibody or a functional variant thereof.

In some embodiments, the T cell stimulatory pathway comprises the Ly9 signaling pathway. In such embodiments, the second agent comprises a Ly9 agonist. In some embodiments, the second agent comprises a Ly9 agonist antibody or a functional variant thereof.

In some embodiments, the T cell stimulatory pathway comprises the Ox40 signaling pathway. In such embodiments, the second agent comprises a Ox40 agonist. In some embodiments, the second agent comprises a Ox40 agonist antibody or a functional variant thereof.

In some embodiments, the T cell stimulatory pathway comprises the CRACC signaling pathway. In such embodiments, the second agent comprises a CRACC agonist. In some embodiments, the second agent comprises a CRACC agonist antibody or a functional variant thereof.

Exemplary T cell co-inhibitory pathways of use herein comprise a T cell co-inhibitory pathway selected from the group consisting of the CTLA4 signaling pathway, the PD1 signaling pathway, the PD1H signaling pathway, the BTLA signaling pathway, the B71 signaling pathway, the PDL1 signaling pathway, the TIGIT signaling pathway, the TIM2 signaling pathway, the TIM3 signaling pathway, the LAIR1 signaling pathway, the LAG3 signaling pathway, and the CD160 signaling pathway.

In some embodiments, the T cell co-inhibitory pathway is the CTLA-4 signaling pathway. In such embodiments, the second agent comprises a CTLA-4 antagonist. In some embodiments, the second agent comprises an aptamer that targets CTLA-4. For example, multivalent RNA aptamers that inhibit CTLA-4 and enhance tumor immunity have been reported (see, e.g., Santulli-Marotto et al. 2003). In some embodiments, the CTLA-4 antagonist comprises an aptamer used for targeted delivery of siRNA to a cell. For example, CTLA-4 aptamer-based targeted delivery of STAT-3 siRNA to T lymphocytes has been reported to inhibit tumor growth and metastasis (see, e.g., Herrmann A., et al. 2014). In some embodiments, the second agent comprises a CTLA-4 antagonist antibody, or a functional variant thereof. In some embodiments, the second agent comprises a fusion protein comprising a CTLA-4 domain (e.g., extracellular domain of CTLA-4) and an antibody fragment (e.g., Fc region of IgG1). In some embodiments, the second agent comprises abatacept. In some embodiments, the second agent comprises belatacept.

In some embodiments, the T cell co-inhibitory pathway is the PD1 signaling pathway. In such embodiments, the second agent comprises a PD1 antagonist. In some embodiments, the second agent comprises an aptamer that targets PD1. In some embodiments, the second agent comprises a PD1 antagonist antibody, or a functional variant thereof. A variety of PD1 antagonist antibodies of use herein are available to the skilled artisan.

In some embodiments, the T cell co-inhibitory pathway is the PD1H signaling pathway. In such embodiments, the second agent comprises a PD1H antagonist. In some embodiments, the second agent comprises an aptamer that targets PD1H. In some embodiments, the second agent comprises a PD1H antagonist antibody, or a functional variant thereof. A variety of PD1H antagonist antibodies of use herein are available to the skilled artisan.

In some embodiments, the T cell co-inhibitory pathway is the BTLA signaling pathway. In such embodiments, the second agent comprises a BTLA antagonist. In some embodiments, the second agent comprises an aptamer that targets BTLA. In some embodiments, the second agent comprises a BTLA antagonist antibody, or a functional variant thereof. A variety of BTLA antagonist antibodies of use herein are available to the skilled artisan.

In some embodiments, the T cell co-inhibitory pathway is the B71 signaling pathway. In such embodiments, the second agent comprises a B71 antagonist. In some embodiments, the second agent comprises an aptamer that targets B71. In some embodiments, the second agent comprises a B71 antagonist antibody, or a functional variant thereof. A variety of B71 antagonist antibodies of use herein are available to the skilled artisan.

In some embodiments, the T cell co-inhibitory pathway is the PDL1 signaling pathway. In such embodiments, the second agent comprises a PDL1 antagonist. In some embodiments, the second agent comprises an aptamer that targets PDL1. In some embodiments, the second agent comprises a PDL1 antagonist antibody, or a functional variant thereof. A variety of PDL1 antagonist antibodies of use herein are available to the skilled artisan.

In some embodiments, the T cell co-inhibitory pathway is the TIGIT signaling pathway. In such embodiments, the second agent comprises a TIGIT antagonist. In some embodiments, the second agent comprises an aptamer that targets TIGIT. In some embodiments, the second agent comprises a TIGIT antagonist antibody, or a functional variant thereof. A variety of TIGIT antagonist antibodies of use herein are available to the skilled artisan.

In some embodiments, the T cell co-inhibitory pathway is the TIM2 signaling pathway. In such embodiments, the second agent comprises a TIM2 antagonist. In some embodiments, the second agent comprises an aptamer that targets TIM2. In some embodiments, the second agent comprises a TIM2 antagonist antibody, or a functional variant thereof. A variety of TIM2 antagonist antibodies of use herein are available to the skilled artisan.

In some embodiments, the T cell co-inhibitory pathway is the TIM3 signaling pathway. In such embodiments, the second agent comprises a TIM3 antagonist. In some embodiments, the second agent comprises an aptamer that targets TIM3. In some embodiments, the second agent comprises a TIM3 antagonist antibody, or a functional variant thereof. A variety of TIM3 antagonist antibodies of use herein are available to the skilled artisan.

In some embodiments, the T cell co-inhibitory pathway is the LAIR1 signaling pathway. In such embodiments, the second agent comprises a LAIR1 antagonist. In some embodiments, the second agent comprises an aptamer that targets LAIR1. In some embodiments, the second agent comprises a LAIR1 antagonist antibody, or a functional variant thereof. A variety of LAIR1 antagonist antibodies of use herein are available to the skilled artisan.

In some embodiments, the T cell co-inhibitory pathway is the LAG3 signaling pathway. In such embodiments, the second agent comprises a LAG3 antagonist. In some embodiments, the second agent comprises an aptamer that targets LAG3. In some embodiments, the second agent comprises a LAG3 antagonist antibody, or a functional variant thereof. A variety of LAG3 antagonist antibodies of use herein are available to the skilled artisan.

In some embodiments, the T cell co-inhibitory pathway is the CD160 signaling pathway. In such embodiments, the second agent comprises a CD160 antagonist. In some embodiments, the second agent comprises an aptamer that targets CD160. In some embodiments, the second agent comprises a CD160 antagonist antibody, or a functional variant thereof. A variety of CD160 antagonist antibodies of use herein are available to the skilled artisan.

In particular embodiments, the first agent is a PDL1 antagonist antibody and the second agent is a 4-1BB agonist antibody. In particular embodiments, the immunoswitch particle comprises a nanoparticle functionalized with both a PDL1 antagonist antibody and a 4-1BB agonist antibody. In particular embodiments, the immunoswitch particle comprises a nanoparticle having a diameter of between about 50 nm and 100 nm functionalized with an effective amount of both a PDL1 antagonist antibody and a 4-1BB agonist antibody. In particular embodiments, the immunoswitch particle comprises a paramagnetic iron-dextran nanoparticle functionalized with both a PDL1 antagonist antibody and a 4-1BB agonist antibody.

In particular embodiments, the first agent is a PDL1 antagonist antibody and the second agent is a CD27 agonist antibody. In particular embodiments, the immunoswitch particle comprises a nanoparticle functionalized with both a PDL1 antagonist antibody and a CD27 agonist antibody. In particular embodiments, the immunoswitch particle comprises a nanoparticle having a diameter of between about 50 nm and 100 nm functionalized with an effective amount of both a PDL1 antagonist antibody and a CD27 agonist antibody. In particular embodiments, the immunoswitch particle comprises a nanoparticle having a diameter of between about 80 nm functionalized with an effective amount of both a PDL1 antagonist antibody and a CD27 agonist antibody. In particular embodiments, the immunoswitch particle comprises a paramagnetic iron-dextran nanoparticle functionalized with both a PDL1 antagonist antibody and a CD27 agonist antibody.

In particular embodiments, the first agent is a PDL1 antagonist antibody and the second agent is a CD28 agonist antibody. In particular embodiments, the immunoswitch particle comprises a nanoparticle functionalized with both a PDL1 antagonist antibody and a CD28 agonist antibody. In particular embodiments, the immunoswitch particle comprises a nanoparticle having a diameter of between about 50 nm and 100 nm functionalized with an effective amount of both a PDL1 antagonist antibody and a CD28 agonist antibody. In particular embodiments, the immunoswitch particle comprises a nanoparticle having a diameter of between about 80 nm functionalized with an effective amount of both a PDL1 antagonist antibody and a CD28 agonist antibody. In particular embodiments, the immunoswitch particle comprises a paramagnetic iron-dextran nanoparticle functionalized with both a PDL1 antagonist antibody and a CD28 agonist antibody.

In particular embodiments, the first agent is a CD73 antagonist antibody and the second agent is a 4-1BB agonist antibody. In particular embodiments, the immunoswitch particle comprises a nanoparticle functionalized with both a CD73 antagonist antibody and a 4-1BB agonist antibody. In particular embodiments, the immunoswitch particle comprises a nanoparticle having a diameter of between about 50 nm and 100 nm functionalized with an effective amount of both a CD73 antagonist antibody and a 4-1BB agonist antibody. In particular embodiments, the immunoswitch particle comprises a nanoparticle having a diameter of between about 80 nm functionalized with an effective amount of both a CD73 antagonist antibody and a 4-1BB agonist antibody. In particular embodiments, the immunoswitch particle comprises a paramagnetic iron-dextran nanoparticle functionalized with both a CD73 antagonist antibody and a 4-1BB agonist antibody.

In particular embodiments, the first agent is a PDL1 antagonist antibody and the second agent is a PD1 antagonist antibody. In particular embodiments, the immunoswitch particle comprises a nanoparticle functionalized with both a PDL1 antagonist antibody and a PD1 antagonist antibody. In particular embodiments, the immunoswitch particle comprises a nanoparticle having a diameter of between about 50 nm and 100 nm functionalized with an effective amount of both a PDL1 antagonist antibody and a PD1 antagonist antibody. In particular embodiments, the immunoswitch particle comprises a nanoparticle having a diameter of between about 80 nm functionalized with an effective amount of both a PDL1 antagonist antibody and a PD1 antagonist antibody. In particular embodiments, the immunoswitch particle comprises a paramagnetic iron-dextran nanoparticle functionalized with both a PDL1 antagonist antibody and a PD1 antagonist antibody.

In particular embodiments, the first agent is a CD73 antagonist antibody and the second agent is a CD27 agonist antibody. In particular embodiments, the immunoswitch particle comprises a nanoparticle functionalized with both a CD73 antagonist antibody and a CD27 agonist antibody. In particular embodiments, the immunoswitch particle comprises a nanoparticle having a diameter of between about 50 nm and 100 nm functionalized with an effective amount of both a CD73 antagonist antibody and a CD27 agonist antibody. In particular embodiments, the immunoswitch particle comprises a nanoparticle having a diameter of between about 80 nm functionalized with an effective amount of both a CD73 antagonist antibody and a CD27 agonist antibody. In particular embodiments, the immunoswitch particle comprises a paramagnetic iron-dextran nanoparticle functionalized with both a CD73 antagonist antibody and a CD27 agonist antibody.

In particular embodiments, the first agent is a CD73 antagonist antibody and the second agent is a CD28 agonist antibody. In particular embodiments, the immunoswitch particle comprises a nanoparticle functionalized with both a CD73 antagonist antibody and a CD28 agonist antibody. In particular embodiments, the immunoswitch particle comprises a nanoparticle having a diameter of between about 50 nm and 100 nm functionalized with an effective amount of both a CD73 antagonist antibody and a CD28 agonist antibody. In particular embodiments, the immunoswitch particle comprises a nanoparticle having a diameter of between about 80 nm functionalized with an effective amount of both a CD73 antagonist antibody and a CD28 agonist antibody. In particular embodiments, the immunoswitch particle comprises a paramagnetic iron-dextran nanoparticle functionalized with both a CD73 antagonist antibody and a CD28 agonist antibody.

The term "antibody," also known as an immunoglobulin (Ig), is a large Y-shaped protein produced by B cells that is used by the immune system to identify and neutralize foreign objects such as bacteria and viruses by recognizing a unique portion (epitope) of the foreign target, called an antigen. As used herein, the term "antibody" also includes an "antigen-binding portion" of an antibody (or simply "antibody portion"). The term "antigen-binding portion," as used herein, refers to one or more fragments of an antibody that retain the ability to specifically bind to an antigen (e.g., PDL1). It has been shown that the antigen-binding function of an antibody can be performed by fragments of a full-length antibody. Examples of binding fragments encompassed within the term "antigen-binding portion" of an antibody include: (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment, which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv)). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and V1 can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (e.g., Holliger et al. (1993) *Proc. Natl. Acad. Sci. USA* 90:6444-6448; Poljak et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the presently disclosed subject matter bind specifically or substantially specifically to an immune checkpoint receptor ligand or functional variants thereof. The terms "monoclonal antibodies" and "monoclonal antibody composition," as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the presently disclosed subject matter may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

An "isolated antibody", as used herein, is intended to refer to an antibody that is substantially free of other antibodies having different antigenic specificities (e.g., an isolated antibody that specifically binds an immune checkpoint receptor ligand is substantially free of antibodies that specifically bind antigens other than the immune checkpoint receptor ligand). Moreover, an isolated antibody may be substantially free of other cellular material and/or chemicals.

An isolated immune checkpoint receptor ligand or functional variant thereof (or a nucleic acid encoding such polypeptides), can be used as an immunogen to generate antibodies that bind to the respective immune checkpoint receptor ligands or functional variants thereof using standard techniques for polyclonal and monoclonal antibody preparation. A full-length immune checkpoint receptor ligand can be used, or alternatively, the presently disclosed subject matter relates to antigenic peptide fragments of an immune checkpoint protein (e.g., receptor or ligand) or functional variants thereof for use as immunogens. An antigenic peptide of an immune checkpoint receptor ligand or a functional variant thereof comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptides are regions of an immune checkpoint receptor ligand or a functional variant thereof that are located on the surface of the protein, e.g., hydrophilic regions. A standard hydrophobicity analysis of the polypeptide molecule can be performed to identify hydrophilic regions. Highly preferred epitopes encompassed by the antigenic peptides are the regions of the polypeptide molecule which are in the extracellular domain, and therefore are involved in binding. In one embodiment, such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

An immunogen comprising an immune checkpoint receptor ligand or a functional variant thereof typically is used to prepare antibodies by immunizing a suitable subject, (e.g., rabbit, goat, mouse or other mammal) with the immunogen. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256:495-497; Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; and Yeh et al. (1982) *Int. J. Cancer* 29:269-75), a human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner (1981) *Yale J. Biol. Med.* 54:387-402; Gefter et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well-known protocols used for fusing lymphocytes and immortalized cell lines can be applied for the purpose of generating a monoclonal antibody to an immune checkpoint receptor ligand (e.g., Galfre, G. et al. (1977) *Nature* 266:55052; Kenneth, R. H. in *Monoclonal Antibodies: A New Dimension In Biological Analyses*, Plenum Publishing Corp., New York, N.Y. (1980); Lerner (1981) *Yale J. Biol. Med.* 54:387-402; Gefter et al. (1977) *Somatic Cell Genet.* 3:231-36). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present presently disclosed subject matter with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O—Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the presently disclosed subject matter are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides antibody can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening an antibody display library can be found in, for example, U.S. Pat. No. 5,223,409; PCT Patent App. Pub. No. WO 92/18619; PCT Patent App. Pub. No. WO 91/17271; PCT Patent App. Pub. No. 92/20791; PCT Patent App. Pub. No. WO 92/15679; PCT Patent App. Pub. No. WO 93/01288; PCT Patent App. Pub. No. WO 92/01047; PCT Patent App. Pub. No. WO 92/09690; PCT Patent App. Pub. No. WO 90/02809; Fuchs et al. (1991) *Biotechnology* (NY) 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992)*J Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology* (NY) 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Additionally, recombinant agents, such as immune checkpoint receptor ligands and chimeric and humanized monoclonal antibodies, comprising both human and non-human portions, which can be made using standard recombinant DNA techniques, are within the scope of the presently disclosed subject matter. Such chimeric and humanized monoclonal antibodies can be produced by recombinant DNA techniques known in the art, for example using methods described in PCT Patent App. Pub. No. PCT/US86/02269; European Patent App. No. 184,187; European Patent App. No. 171,496; European Patent App. No. 173,494; PCT Application WO 86/01533; U.S. Pat. No. 4,816,567; European Patent App. No. 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *Biotechniques* 4:214; U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (e.g., Carlson (1988) *Mol. Cell. Biol.* 8:2638-2646; Biocca et al. (1990) *EMBO J.* 9:101-108; Werge et al. (1990) *FEBS Lett* 274:193-198; Carlson (1993) *Proc. Natl. Acad. Sci. USA* 90:7427-7428; Marasco et al. (1993) *Proc. Natl. Acad. Sci. USA* 90:7889-7893; Biocca et al. (1994) *Biotechnology* (NY) 12:396-399; Chen et al. (1994) *Hum. Gene Ther.* 5:595-601; Duan et al. (1994) *Proc. Natl. Acad. Sci. USA*

91:5075-5079; Chen et al. (1994) *Proc. Natl. Acad. Sci. USA* 91:5932-5936; Beerli et al. (1994) *J. Biol. Chem.* 269:23931-23936; Beerli et al. (1994) *Biochem. Biophys. Res. Commun.* 204:666-672; Mhashilkar et al. (1995) *EMBO J.* 14:1542-1551; Richardson et al. (1995) *Proc. Natl. Acad. Sci. USA* 92:3137-3141; PCT Publication No. WO 94/02610; and PCT Publication No. WO 95/03832).

Additionally, fully human antibodies could be made against an immune checkpoint receptor ligand or a functional variant thereof. Fully human antibodies can be made in mice that are transgenic for human immunoglobulin genes, e.g. according to Hogan, et al., "Manipulating the Mouse Embryo: A Laboratory Manual," Cold Spring Harbor Laboratory. Briefly, transgenic mice are immunized with a purified immune checkpoint protein or a functional variant thereof. Spleen cells are harvested and fused to myeloma cells to produce hybridomas. Hybridomas are selected based on their ability to produce antibodies which bind to an immune checkpoint receptor ligand or a functional variant thereof. Fully human antibodies would reduce the immunogenicity of such antibodies in a human.

In one embodiment, an antibody for use in the instant presently disclosed subject matter is a bispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA,* 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to an immune checkpoint receptor ligand or a functional variant thereof.

Yet another aspect of the presently disclosed subject matter pertains to antibodies that are obtainable by a process comprising, immunizing an animal with an immunogenic immune checkpoint receptor ligand or a functional variant thereof, or an immunogenic portion thereof unique to the immune checkpoint receptor ligand, and then isolating from the animal antibodies that specifically bind to the polypeptide.

In some embodiments, other immunoregulatory entities can be combined with the presently disclosed antibodies. Such immunoregulatory entities may include, for example, immunostimulatory cytokines such as GM-CSF, Interleukin-12 (IL-12), and IL-15.

As used herein, "functional variants", for example of PDL1 antagonist antibodies, 4-1BB agonist antibodies, CD27 agonist antibodies, CD28 agonist antibodies, CD73 antagonist antibodies, CTLA-4 antagonist antibodies, etc., include functional fragments, functional mutant proteins, and/or functional fusion proteins. A functional variant of a selected polypeptide refers to an isolated and/or recombinant protein or polypeptide which has at least one property, activity and/or functional characteristic of the selected polypeptide (e.g., PDL1 antagonism, 4-1BB agonism, CD27 agonism, CD28 agonism, CD73 antagonism, CTLA-4 antagonism). As used herein, the term "activity," when used with respect to a polypeptide, e.g., PDL1 antagonist antibody, includes activities which are inherent in the structure of the wild-type protein.

Generally, fragments or portions of antibodies encompassed by the presently disclosed subject matter (e.g., PDL1 antagonist antibodies, 4-1BB agonist antibodies, CD27 agonist antibodies, CD28 agonist antibodies, CD73 antagonist antibodies, CTLA-4 antagonist antibodies, etc.) include those having a deletion (i.e. one or more deletions) of an amino acid (i.e., one or more amino acids) relative to the antibodies (e.g., PDL1 antagonist antibodies, 4-1BB agonist antibodies, CD27 agonist antibodies, CD28 agonist antibodies, CD73 antagonist antibodies, CTLA-4 antagonist antibodies, etc.) (such as N-terminal, C-terminal or internal deletions). Similarly, fragments or portions of antibodies include those having a deletion (i.e., one or more deletions) of an amino acid i.e., one or more amino acids) relative to the wild-type proteins (such as N-terminal, C-terminal or internal deletions). Fragments or portions in which only contiguous amino acids have been deleted or in which non-contiguous amino acids have been deleted relative to a wild-type proteins are also envisioned. Generally, mutants or derivatives of proteins encompassed by the present presently disclosed subject matter include natural or artificial variants differing by the addition, deletion and/or substitution of one or more contiguous or non-contiguous amino acid residues, or modified polypeptides in which one or more residues is modified, and mutants comprising one or more modified residues. Preferred mutants are natural or artificial variants of proteins differing by the addition, deletion and/or substitution of one or more contiguous or non-contiguous amino acid residues.

Generally, a functional variant of a PDL1 antagonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a PDL1 antagonist antibody amino acid sequence over the length of the variant.

Generally, a functional variant of an 4-1BB agonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a 4-1BB agonist antibody amino acid sequence over the length of the variant.

Generally, a functional variant of an CD27 agonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a CD28 agonist antibody amino acid sequence over the length of the variant.

Generally, a functional variant of an CD28 agonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a CD28 agonist antibody amino acid sequence over the length of the variant.

Generally, a functional variant of a CD73 antagonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a CD73 antagonist amino acid sequence over the length of the variant.

Generally, a functional variant of an CTLA-4 antagonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a CTLA-4 antagonist antibody amino acid sequence over the length of the variant.

Generally, a functional variant of an PD1 antagonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a PD1 antagonist antibody amino acid sequence over the length of the variant.

Generally, a functional variant of a PD1H antagonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a PD1H antagonist antibody amino acid sequence over the length of the variant.

Generally, a functional variant of a BTLA antagonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a BTLA antagonist antibody amino acid sequence over the length of the variant.

Generally, a functional variant of a B71 antagonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a B71 antagonist antibody amino acid sequence over the length of the variant.

Generally, a functional variant of a TIGIT antagonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a TIGIT antagonist antibody amino acid sequence over the length of the variant.

Generally, a functional variant of a TIM2 antagonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a TIM2 antagonist antibody amino acid sequence over the length of the variant.

Generally, a functional variant of a TIM3 antagonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a TIM3 antagonist antibody amino acid sequence over the length of the variant.

Generally, a functional variant of a LAIR1 antagonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a LAIR1 antagonist antibody amino acid sequence over the length of the variant.

Generally, a functional variant of a LAG3 antagonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a LAG3 antagonist antibody amino acid sequence over the length of the variant.

Generally, a functional variant of a CD160 antagonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a CD160 antagonist antibody amino acid sequence over the length of the variant.

Generally, a functional variant of an ICOS agonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a ICOS agonist antibody amino acid sequence over the length of the variant.

Generally, a functional variant of an CD226 agonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a CD226 agonist antibody amino acid sequence over the length of the variant.

Generally, a functional variant of an CRTAM agonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a CRTAM agonist antibody amino acid sequence over the length of the variant.

Generally, a functional variant of an TIM1 agonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a TIM1 agonist antibody amino acid sequence over the length of the variant.

Generally, a functional variant of an CD2 agonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a CD2 agonist antibody amino acid sequence over the length of the variant.

Generally, a functional variant of an SLAM agonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a SLAM agonist antibody amino acid sequence over the length of the variant.

Generally, a functional variant of an CD84 agonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a CD84 agonist antibody amino acid sequence over the length of the variant.

Generally, a functional variant of an Ly9 agonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a Ly9 agonist antibody amino acid sequence over the length of the variant.

Generally, a functional variant of an Ox40 agonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a Ox40 agonist antibody amino acid sequence over the length of the variant.

Generally, a functional variant of an CRACC agonist antibody has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to a CRACC agonist antibody amino acid sequence over the length of the variant.

"Sequence identity" or "identity" in the context of proteins or polypeptides refers to the amino acid residues in two amino acid sequences that are the same when aligned for maximum correspondence over a specified comparison window.

Thus, "percentage of sequence identity" refers to the value determined by comparing two optimally aligned sequences over a comparison window, wherein the portion of the amino acid sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized. The "Clustal V method of alignment" corresponds to the alignment method labeled Clustal V (described by Higgins and Sharp (1989) CABIOS 5:151-153; Higgins et al. (1992) Comput. Appl. Biosci. 8:189-191) and found in the MegAlign™ program of the LASERGENE bioinformatics computing suite (DNASTAR Inc., Madison, Wis.).

It is well understood by one skilled in the art that many levels of sequence identity are useful in identifying proteins or polypeptides (e.g., from other species) wherein the proteins or polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%. Indeed, any integer amino acid identity from 50% to 100% may be useful in describing the present presently disclosed subject matter, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

V. Pharmaceutical Compositions

The presently disclosed subject matter also contemplates pharmaceutical compositions comprising one or more immunoswitch particles for the treatment of cancer. In some embodiments, the presently disclosed methods comprise the use of the presently disclosed immunoswitch particles for the manufacture of a medicament for the treatment of cancer.

Accordingly, in some embodiments, the presently disclosed subject matter provides a pharmaceutical composition comprising an effective amount of at least one immunoswitch particle that treats a cancer, and a pharmaceutically acceptable carrier, diluent, or excipient.

In some embodiments, the immunoswitch particle composition comprises one or more additional therapeutic agents described herein (e.g., chemotherapeutic agents, immunotherapeutic agents, anti-inflammatory agents, and vaccines). Generally, the presently disclosed compositions (e.g., comprising at least one immunoswitch particle) can be administered to a subject for therapy by any suitable route of administration, including orally, nasally, transmucosally, ocularly, rectally, intravaginally, parenterally, including intramuscular, intratumorally, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art. In some embodiments, the immunoswitch particle or composition thereof is administered to a subject intratumorally in an amount effective for treating cancer. In some embodiments, the immunoswitch particle is administered once daily. In some embodiments, the immunoswitch particle is administered every other day. In some embodiments, the immunoswitch particle is administered every third, every fourth, every fifth, or every sixth day. In some embodiments, the immunoswitch particle is administered once a week. In some embodiments, the immunoswitch particle is administered twice daily. In some embodiments, the immunoswitch particle is administered twice a week. In some embodiments, the immunoswitch particle is administered once a month. In some embodiments, the immunoswitch particle is administered twice a month. In some embodiments, the immunoswitch particle is administered after completion of a conventional cancer regiment (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days post completion of treatment with the conventional cancer regiment).

The phrases "systemic administration," "administered systemically," "peripheral administration" and "administered peripherally" as used herein mean the administration of compositions comprising at least one immunoswitch particle, such that it enters the patient's system and, thus, are subject to metabolism and other like processes, for example, subcutaneous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

The presently disclosed pharmaceutical compositions can be manufactured in a manner known in the art, e.g., by means of conventional mixing, dissolving, granulating, dragee-making, levitating, emulsifying, encapsulating, entrapping or lyophilizing processes.

In some embodiments, the presently disclosed pharmaceutical compositions can be administered by rechargeable or biodegradable devices. For example, a variety of slow-release polymeric devices have been developed and tested in vivo for the controlled delivery of drugs, including proteinacious biopharmaceuticals. Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., Biopolymers 22:547, 1983), poly (2-hydroxyethyl-methacrylate) (Langer et al. (1981) *J. Biomed. Mater. Res.* 15:167; Langer (1982), *Chem. Tech.* 12:98), ethylene vinyl acetate (Langer et al. (1981) *J Biomed. Mater. Res.* 15:167), or poly-D-(-)-3-hydroxybutyric acid (EP 133,988A). Sustained release compositions also include liposomally entrapped compositions comprising at least one immunoswitch particle which can be prepared by methods known in the art (Epstein et al. (1985) *Proc. Natl. Acad. Sci. U.S.A.* 82:3688; Hwang et al. (1980) *Proc. Natl. Acad. Sci. U.S.A.* 77:4030; U.S. Pat. Nos. 4,485, 045 and 4,544,545; and EP 102,324A). Ordinarily, the liposomes are of the small (about 200-800 angstroms) unilamelar type in which the lipid content is greater than about 30 mol % cholesterol, the selected proportion being adjusted for the optimal therapy. Such materials can comprise an implant, for example, for sustained release of the presently disclosed compositions, which, in some embodiments, can be implanted at a particular, pre-determined target site.

In another embodiment, the presently disclosed pharmaceutical compositions may comprise PEGylated therapeutics (e.g., PEGylated antibodies). PEGylation is a well-established and validated approach for the modification of a range of antibodies, proteins, and peptides and involves the attachment of polyethylene glycol (PEG) at specific sites of the antibodies, proteins, and peptides (Chapman (2002) *Adv. Drug Deliv. Rev.* 54:531-545). Some effects of PEGylation include: (a) markedly improved circulating half-lives in vivo due to either evasion of renal clearance as a result of the polymer increasing the apparent size of the molecule to above the glomerular filtration limit, and/or through evasion of cellular clearance mechanisms; (b) improved pharmacokinetics; (c) improved solubility—PEG has been found to be soluble in many different solvents, ranging from water to many organic solvents, such as toluene, methylene chloride, ethanol and acetone; (d) PEGylated antibody fragments can be concentrated to 200 mg/mL, and the ability to do so opens up formulation and dosing options, such as subcutaneous administration of a high protein dose; this is in contrast to many other therapeutic antibodies which are typically administered intravenously; (e) enhanced proteolytic resistance of the conjugated protein (Cunningham-Rundles et. al. (1992) *J. Immunol. Meth.* 152:177-190); (0 improved bioavailability via reduced losses at subcutaneous injection sites; (g) reduced toxicity has been observed; for agents where toxicity is related to peak plasma level, a flatter pharmacokinetic profile achieved by sub-cutaneous administration of PEGylated protein is advantageous; proteins that elicit an immune response which has toxicity consequences may also benefit as a result of PEGylation; and (h) improved thermal and mechanical stability of the PEGylated molecule.

Pharmaceutical compositions for parenteral administration include aqueous solutions of compositions comprising at least one immunoswitch particle. For injection, the presently disclosed pharmaceutical compositions can be formulated in aqueous solutions, for example, in some embodiments, in physiologically compatible buffers, such as Hank's solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of compositions include fatty oils, such as sesame oil, or synthetic fatty acid esters, such as ethyl oleate or triglycerides, or liposomes. Optionally, the suspension also can contain suitable stabilizers or agents that increase the solubility of the compositions comprising at least one immunoswitch particle to allow for the preparation of highly concentrated solutions.

For nasal or transmucosal administration generally, penetrants appropriate to the particular barrier to be permeated are used in the formulation. Such penetrants are generally known in the art.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

Regardless of the route of administration selected, the presently disclosed compositions are formulated into pharmaceutically acceptable dosage forms, such as described herein or by other conventional methods known to those of skill in the art.

In general, the "effective amount", "amount effective to treat" or "therapeutically effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like. Generally, the "effective amount" or "amount effective" to treat a cognitive deficit is less than the effective amount needed to treat cancer. It should be appreciated that the amount of at least one immunoswitch particle or composition thereof effective to treat cancer comprises the maximal non-toxic dose that is sufficient for delaying or preventing tumor growth or extending a length of survival (e.g., progression free survival) of particular cancer in a subject. It should further be appreciated that the amount of at least one immunoswitch particle or composition thereof effective to treat chronic viral infection comprises the maximal non-toxic dose that is sufficient for inhibiting viral infection, replication, and/or multiplicity of infection of virus infected cells in a subject. In some embodiments, the effective amount of at least one immunoswitch particle or composition thereof includes about 2-fold less, 5-fold less, 10-fold less, 20-fold less, 25-fold less, 33-fold less, 50-fold less, 75-fold less, 80-fold less, 90-fold less, or 100-fold less total antibody than is typically used for treatment when soluble antibody is injected intraperitoneally. In some embodiments, the effective amount of at least one immunoswitch particle comprises 0.1-100 μg total antibody conjugated to the immunoswitch nanoparticles. In other embodiments, the effective amount of at least one immunoswitch particle comprises 1-10 μg total antibody conjugated to the immunoswitch particles.

The term "combination" is used in its broadest sense and means that a subject is administered at least two agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the presently disclosed compositions can be administered alone or in combination with adjuvants that enhance stability of the agents, facilitate administration of pharmaceutical compositions containing them in certain embodiments, provide increased dissolution or dispersion, increase activity, provide adjuvant therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of at least one immunoswitch particle can be varied so long as the beneficial effects of the combination of these agents are achieved. Accordingly, the phrase "in combination with" refers to the administration of at least one immunoswitch particle, and optionally additional agents either simultaneously, sequentially, or a combination thereof. Therefore, a subject administered a combination of at least one immunoswitch particle, and optionally additional agents can receive at least one immunoswitch particle, and optionally additional agents at the same time (i.e., simultaneously) or at different times (i.e., sequentially, in either order, on the same day or on different days), so long as the effect of the combination of all agents is achieved in the subject.

When administered sequentially, the agents can be administered within 1, 5, 10, 30, 60, 120, 180, 240 minutes or longer of one another. In other embodiments, agents administered sequentially, can be administered within 1, 2, 3, 4, 5, 10, 15, 20 or more days of one another. Where the agents are administered simultaneously, they can be administered to the subject as separate pharmaceutical compositions, each comprising at least one immunoswitch particle, and optionally additional agents, or they can be administered to a subject as a single pharmaceutical composition comprising all agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of an agent and at least one additional therapeutic agent is greater than the sum of the biological activities of the respective agents when administered individually.

Synergy can be expressed in terms of a "Synergy Index (SI)," which generally can be determined by the method described by F. C. Kull et al. Applied Microbiology 9, 538 (1961), from the ratio determined by:

$$Q_a Q_A + Q_b Q_B = \text{Synergy Index (SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

In another aspect, the presently disclosed subject matter provides a pharmaceutical composition including at least one immunoswitch particle, and optionally additional agents, alone or in combination with one or more additional therapeutic agents in admixture with a pharmaceutically acceptable excipient.

More particularly, the presently disclosed subject matter provides a pharmaceutical composition comprising at least one immunoswitch particle, and optionally additional agents, and a pharmaceutically acceptable carrier. In therapeutic and/or diagnostic applications, the compounds of the disclosure can be formulated for a variety of modes of administration, including systemic and topical or localized administration. Techniques and formulations generally may be found in Remington: The Science and Practice of Pharmacy (20$^{th}$ ed.) Lippincott, Williams and Wilkins (2000).

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

VI. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Throughout the specification and claims, a given chemical formula or name shall encompass all tautomers, congeners, and optical- and stereoisomers, as well as racemic mixtures where such isomers and mixtures exist.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Immunoswitch Particle Synthesis and Characterization

Immunoswitch particles were synthesized by functionalizing 80 nm iron-dextran nanoparticles with the desired antibodies. Anti-biotin coated iron-dextran 50-100 nm particles were purchased from Miltenyi (Miltenyi Biotec; Auburn, CA). Anti-PDL1 antibody clone 10F.9G2, anti-4-1BB clone 3H3, and their respective isotype controls were purchased from BioXCell (West Lebanon, NH) and were biotinylated using EZ-Link sulfo-NHS-biotin (Thermo Fisher Scientific; Waltham, MA) according to the manufacturer's protocol. Particles and a 2-fold molar excess of biotinylated antibody were combined and allowed to conjugate for 24 hours at 4° C. Unbound antibody was removed by running the particles over an MS column (Miltenyi Biotec, Auburn, CA) and washing according to the manufacturer's protocol. Anti-4-1BB only, anti-PDL1 only, and isotype particles were synthesized by the above protocol, but substituting for the antibody of interest.

Particle size was determined by nanoparticle tracking analysis using a Nanosight LM10. To characterize particle conjugation, a standard curve relating absorbance to particle concentration was made using a Beckman Coulter AD340 plate reader and Nanosight LM10. Particles were then subsequently measured for absorbance to determine concentration, and all particles were brought to a concentration of $1.4 \times 10^{12}$ particles/mL. The amount of specific antibody per particle was determined by staining the particles with fluorescently-labeled secondary antibodies against the antibody of interest. Excess antibody was removed by running the particles over an MS column (Miltenyi Biotec, Auburn, CA), and antibody concentration was measured by comparing particle fluorescence to a standard curve and correlating with the total bead concentration.

Example 2

In Vitro CD8 Activation Model

On day −8, primary splenocytes were isolated from naïve 2C transgenic mouse (Jackson Labs; Bar Harbor, ME) spleens through cell straining. Cells were treated with 4 mL of ACK lysis buffer for 1 minute to lyse red blood cells. CD8+ T cells were isolated by negative selection with the Miltenyi CD8a+ isolation kit IIa following the manufacturer's protocol (Miltenyi, Auburn, CA). Micro Kb-SIY dimer/anti-CD28 (37.51, BioXCell; West Lebanon, NH) aAPC were synthesized on 4.5 µm M-450 Epoxy Dynabeads (Life Technologies; Grand Island, NY) at a 1:1 protein ratio, following manufacturer's protocol. Kb-SIY dimer was produced as previously described (Dal Porto, et al., 1993), and anti-CD28 antibody was purchased from BioXCell (West Lebanon, NH). 2C CD8 T cells were mixed with micro aAPC at a 1:1 ratio and cultured in RPMI supplemented with L-glutamine, non-essential amino acids, vitamin solution, sodium pyruvate, β-mercaptoethanol, 10% FBS, ciproflaxin, and a cocktail of T cell growth factors. On day −4, additional T cell growth factors and Kb-SIY/anti-CD28 beads were added at a 2:1 bead:cell ratio. On day −2, B16-SIY and B16-F10 cells were cultured in RPMI supplemented with L-glutamine, non-essential amino acids, vitamin solution, sodium pyruvate, β-mercaptoethanol, 10% FBS, ciproflaxin, and 20 ng/ml recombinant murine IFN-γ (R&D Systems, Minneapolis, MN).

On day 0, B16-F10 and B16-SIY were harvested and washed three times to remove all IFN-γ, as confirmed by ELISA. 2C cells were also harvested, washed three times, and aAPC were removed with a magnet. Live CD8+ cells were isolated by density centrifugation using Ficoll-Paque PLUS (GE Healthcare Life Sciences; Pittsburgh, PA). Surface marker expression on both cell types was measured using a BD FacsCalibur flow cytometer and analyzed in FlowJo (TreeStar). 2C cells and B16-SIY or B16-F10 cells were mixed at a 1:1 effector target ratio in the presence of particles or soluble antibody. The cells were incubated for 18 hours at 37°, then supernatants were collected. IFN-γ was measured by ELISA using the ebioscience murine IFN-γ Ready-SET-Go! Kit (San Diego, CA).

Example 3

B16-SIY In Vivo Tumor Growth Experiment with Adoptive Transfer

Immunoswitch and isotype particles were synthesized and characterized as described above. Amount of antibody on the particles was quantified and a solution of equal concentration non-biotinylated antibody was diluted in PBS. Particles and soluble antibody were put to a concentration of 13 µg/mL total antibody (6.3 µg/mL anti-PDL1 and 6.3 µg/mL anti-4-1BB) and treated mice received 100 µl each.

C57BL/6 (Jackson Labs; Bar Harbor, ME) mice were injected with $1 \times 10^6$ B16-SIY cells subcutaneously on the right flank on day 0 and cages were randomly assigned to one of five groups: 1) no treatment, 2) CD8 adoptive transfer (AT), 3) AT+ isotype particles, 4) AT+ soluble anti-4-1BB and anti-PDL1 antibody, or 5) AT+ immunoswitch particles (n=4 isotype group, n=8 immunoswitch group, n=9/other groups). In parallel, CD8+ cells were harvested from naïve 2C splenocytes and stimulated with Kb-SIY/anti-CD28 aAPC on days 0 and 4 as described above. On day 8, when all mice had palpable tumor, aAPC were isolated from CD8+ cells and live cells were isolated by density centrifugation using Ficoll-Paque PLUS (GE Healthcare Life Sciences; Pittsburgh, PA). $5 \times 10^5$ 2 C CD8+ cells were intravenously injected into all groups (except no treatment group) through the tail vein. On days 8, 11, and 15, isotype particles, immunoswitch particles, or soluble antibody were injected intratumorally. Beginning on day 8, tumors were measured every 2-3 days using digital calipers, and tumor size was computed by multiplying the longest dimension by the length of the perpendicular dimension. Mice were sacrificed when tumor area surpassed 200 mm².

Example 4

B16-SIY In Vivo Tumor Growth without Adoptive Transfer

Immunoswitch particles, anti-4-1BB only particles, and anti-PDL1 only particles were synthesized as described above. Amount of antibody on all particles was quantified by the methods described above, and immunoswitch particles were put at a concentration of 13 µg/mL total antibody. Anti-4-1BB only and anti-PDL1 only particles were combined and also put at 13 µg/mL total antibody. Treated mice received 100 µl particles/mouse.

C57BL/6 mice (Jackson Labs; Bar Harbor, ME) were injected with $1 \times 10^6$ B16-SIY cells subcutaneously on day 0 and cages were randomly assigned to one of three groups: 1) no treatment, 2) immunoswitch particles, or 3) anti-4-1BB only and anti-PDL1 only particle mixture (n=6 separate particle treatment, n=11/other groups). No CD8+ cell adoptive transfer was given at any time. Particle injections were given to the treated groups intratumorally on days 8, 11, and 15, and tumors were measured every 2-3 days as above.

Example 5

B16-SIY Tumor Infiltrating Lymphocyte Analysis

Immunoswitch particles were synthesized and characterized as above and put at a concentration of 13 µg/mL total antibody. Treated mice received 100 µl of particles/mouse. C57BL/6 (Jackson Labs; Bar Harbor, ME) mice were injected with $1 \times 10^6$ B16-SIY cells subcutaneously on day 0 and cages were randomly assigned to one of two groups: 1) no treatment or 2) immunoswitch particles (n=5/group). Immunoswitch particle treatment was administered intratumorally on days 8 and 11.

On day 14, tumors were measured and tumors and tumor draining lymph nodes were isolated from all mice. Tumor draining lymph nodes were brought to a single cell suspension using a cell strainer, washed, then resuspended in PBS. Tumors were coarsely sectioned using scissors then also brought to a single cell suspension using a cell strainer. Tumor infiltrating lymphocytes (TILS) were isolated by density centrifugation using Ficoll-Paque PLUS (GE Healthcare Life Sciences; Pittsburgh, PA) then washed three times and resuspended in PBS. Cell counts were taken using a hemocytometer.

Isolated cells were stained with a fluorescently labeled with a live/dead stain (Thermo Fish Scientific; Waltham, MA), CD8 antibody (BioLegend; San Diego, CA), and biotinylated Kb-SIY dimer followed by fluorescently labeled streptavidin. Cells were run on a BD LSR II flow cytometer and analyzed using FlowJoe (TreeStar). CD8 cell density was measured by multiplying the CD8 purity measured by flow cytometry by the total cell count, and dividing by the tumor volume (longest dimension squared and multiplied by the perpendicular dimension).

Example 6

MC38-OVA In Vivo Tumor Model

Immunoswitch particles and isotype particles were synthesized as described above. Amount of antibody on all particles was quantified by the methods described above, and particles were put at a concentration of 13 µg/mL total antibody. Treated mice received 100 µl particles/mouse.

C57BL/6 (Jackson Labs; Bar Harbor, ME) mice were injected with $1 \times 10^6$ MC38-OVA cells subcutaneously on day 0 and cages were randomly assigned to one of three groups: 1) no treatment, 2) isotype particles, or 3) immunoswitch particles. On days 8, 11, 15, and 18 treated mice received intratumoral injections of immunoswitch or isotype particles and tumors were measured every 2-3 days.

Example 7

Immunoswitch Biodistribution

Immunoswitch particles were synthesized as described earlier. Immunoswitch particles and a mixture of soluble anti-4-1BB and anti-PDL1 antibody were labeled with IRDye 680RD protein labeled kits from LI-COR Biosciences (Lincoln, Nebraska) according to the manufacturer's protocol.

Nude mice (Jackson Labs; Bar Harbor, ME) were injected with equal protein amounts of either IR-labeled soluble antibody or immunoswitch particles subcutaneously on the right flank (n=3/group). Dorsal, ventral, right, and left images of the mice were taken at 3, 24, 48, and 72 hours post injection. Only right images which show the injection area are shown. All images from any individual mouse had matched thresholding to each other. Images were analyzed in ImageJ by defining a region of interest (ROI) around the initial injection site which was then duplicated in all images. The mean gray value of each ROI was then measured in ImageJ. The mean grey value for an image of an individual mouse at time T was then normalized to the mean grey value at 3 hours using the following equation:

$$\text{Mean gray value (normalized)} = \frac{\text{mean gray } value_{t=T}}{\text{mean gray } value_{t=3}}$$

Example 8

Conjugation Assay

2C CD8 cells were isolated from naïve splenoctyes and stimulated on days −8 and −4 with aAPC as previously described. B16-F10 cells were incubated with media supplemented with 20 ng/ml recombinant murine IFN-γ (R&D Systems; Minneapolis, MN) on day −2 for 48 hours.

On day 0, CD8 cells and B16-F10 cells were isolated from aAPC and IFN-γ respectively, as previously described. CD8 cell membranes were labeled with the PKH26 red fluorescent cell linker kit and B16-F10 cell membranes were labeled with the PKH67 green fluorescent cell linker kit (Sigma-Aldrich; St. Louis, MO) according to the manufacturer's protocol. Effector and target cells were co-incubated at a 1:1 ratio with immunoswitch or isotype particles. After 1 hour, cells were briefly vortexed and fixed. For flow cytometry experiments, cells were fixed in 0.5% paraformaldehyde for 20 min at room temperature. Cells were then read on a BD FacsCalibur and conjugates were analyzed by gating on double red/green positive events using FlowJo (TreeStar). Flow cytometry experiments were repeated 3 independent times. For confocal microscopy experiments, cells were fixed in 2% paraformaldehyde for 20 min at room temperature. Cells were then read on a Zeiss LSM510-Meta laser scanning confocal microscope at 100× magnification. Two to three non-overlapping images were taken per experiment, and the experiment was repeated three times, each independently of one another. Conjugate formation was determined manually by observing red/green overlap/contact using ImageJ. Each image was taken as an independent data point. For both flow cytometry and confocal microscopy studies, conjugation was measured as the percent of CD8 cells forming conjugates with B16-F10 cells divided by the total number of CD8 cells.

Example 9

Immunoswitch Particles Activate PD1$^{hi}$ CD8 Cells In Vitro

Figure 1A:
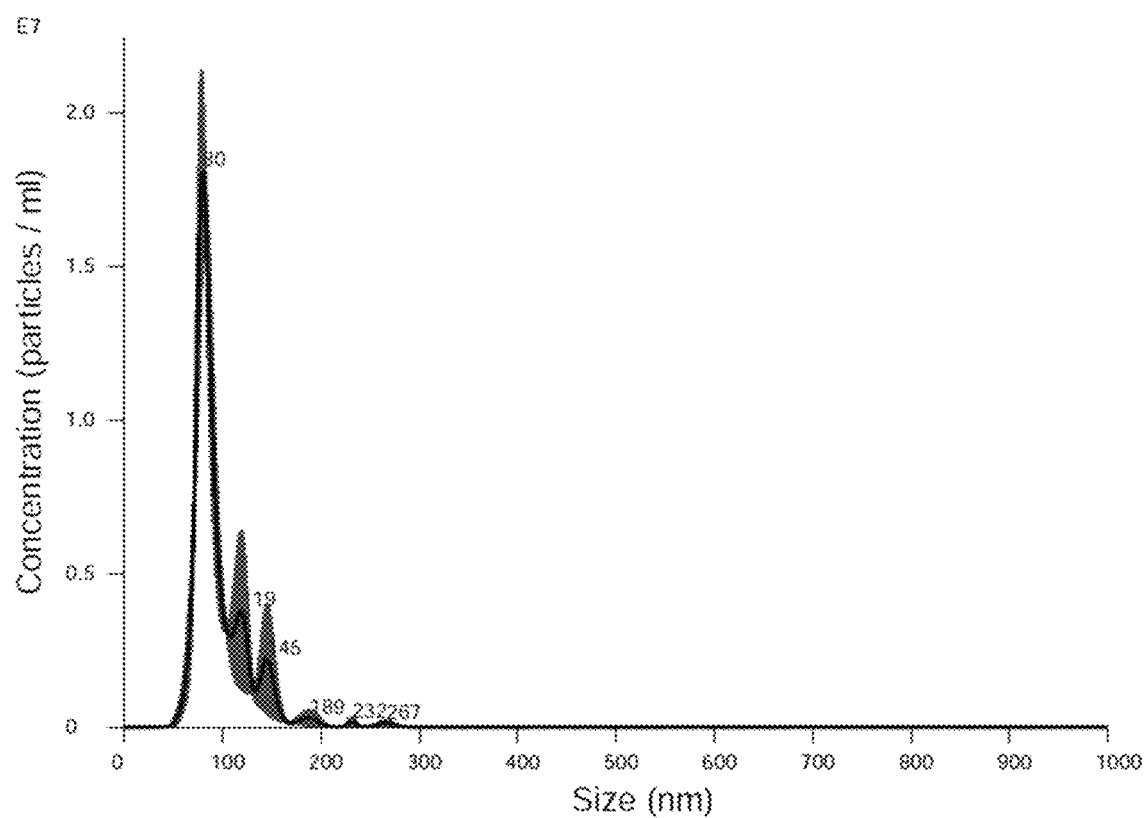
Figure 1B:
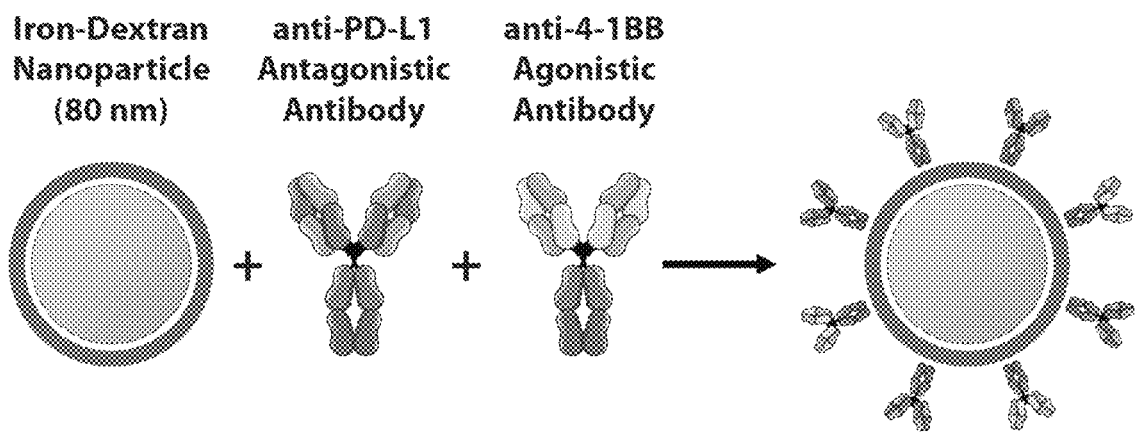
Figure 1C:
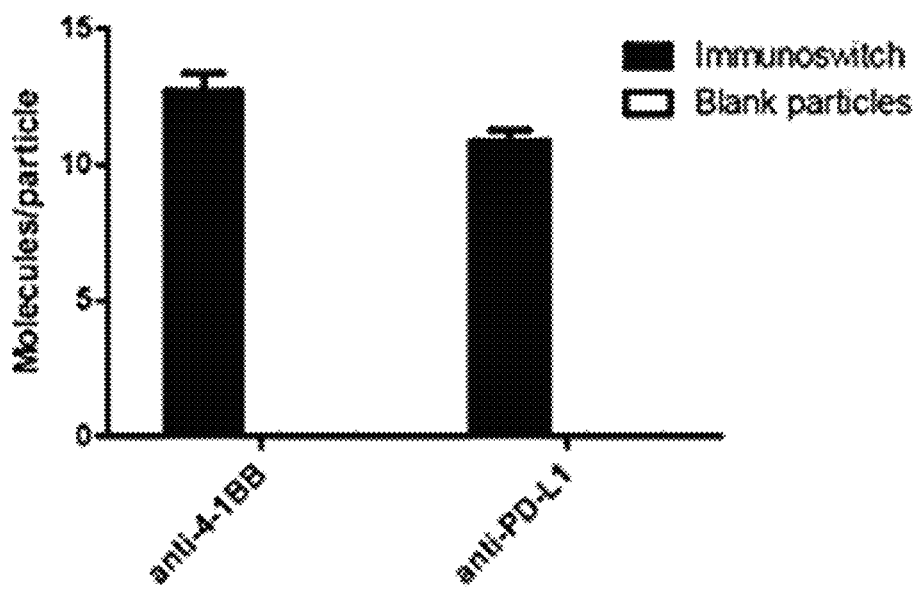
Figure 1D:
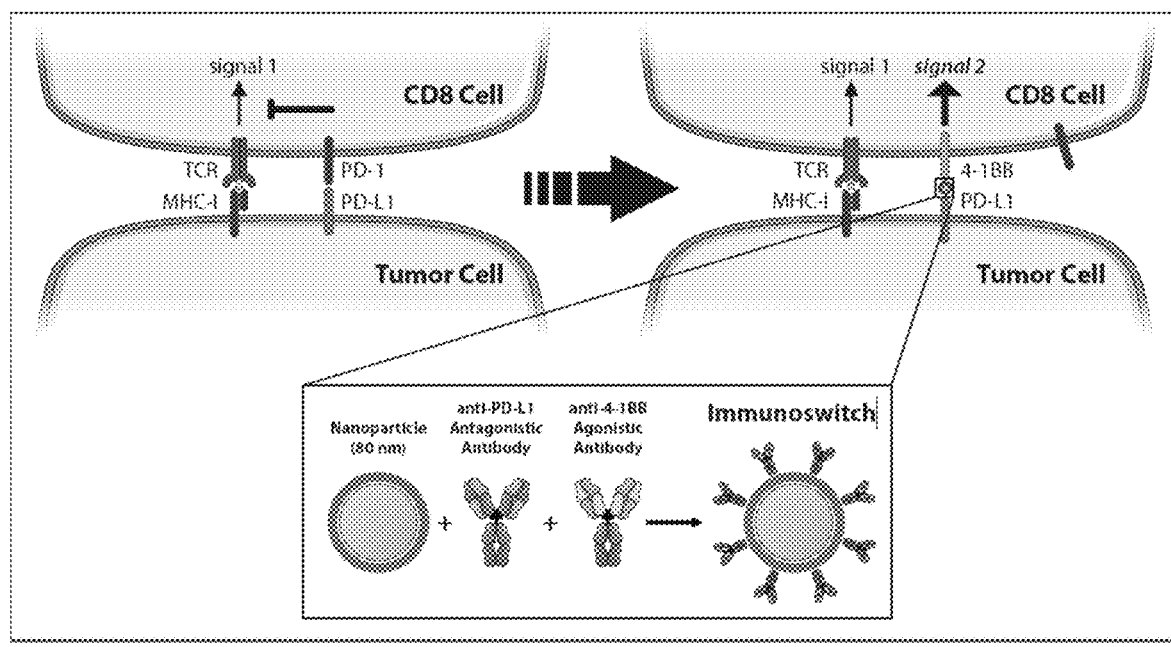

Immunoswitch particles link checkpoint blockade with T cell co-stimulation on a single platform. The particles are synthesized by conjugating 80 nm iron dextran nanoparticles (FIG. 1A) with agonistic antibodies against 4-1BB (found on the effector T cells) and antagonistic antibodies against PDL1 (found on the cancer cells) (FIG. 1B). A 1:1 molar ratio of the antibodies are conjugated to particles and quantified using fluorescently labeled secondary antibodies (FIG. 1C). The hypothesized mechanism of action of the immunoswitch particles is shown in a schematic in FIG. 1D—the particles bind to both 4-1BB on the CD8 cell and PDL1 on the tumor cell, thereby switching a negative signal into a co-stimulatory signal while the clonotypic TCR on CD8+ T cells receive their cognate signal 1 stimulation from the tumor cell itself. If the immunoswitch particles are shown to interact with CD8+ T cells in this fashion, they could activate a polyclonal population of tumor-specific T cells and eliminate the requirement for a priori knowledge of the tumor-antigen to target. This would result in a more durable therapeutic resistant to antigenic escape.

Figure 1E:
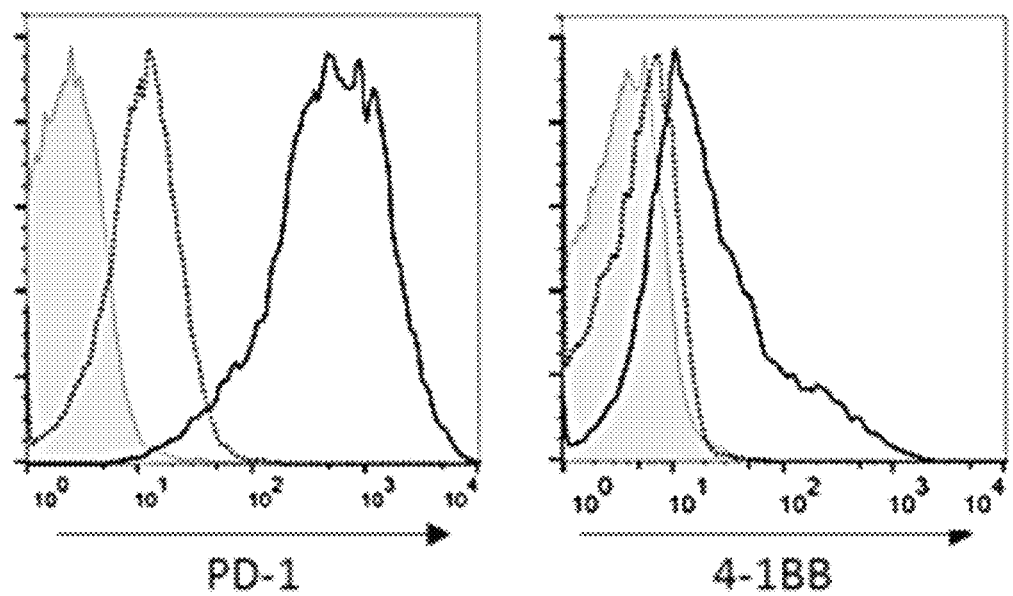
Figure 1F:
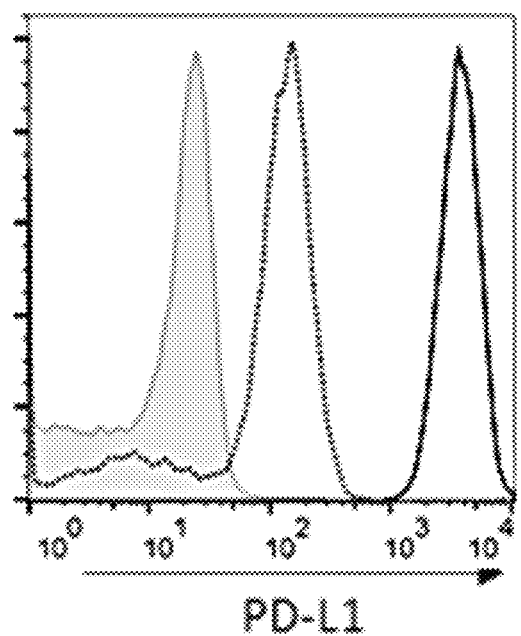
Figure 1G:
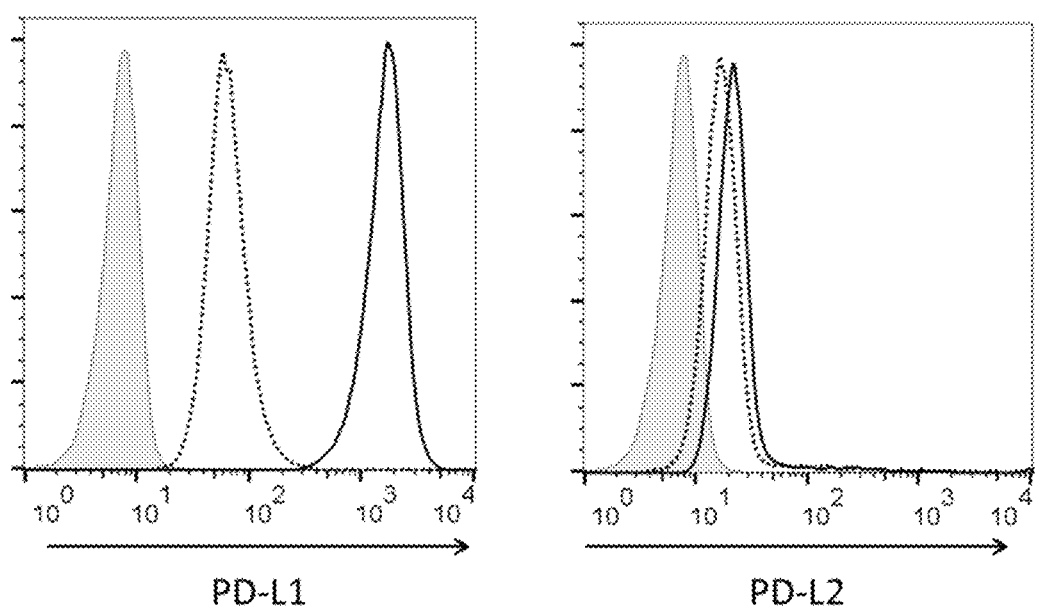
Figure 1H:
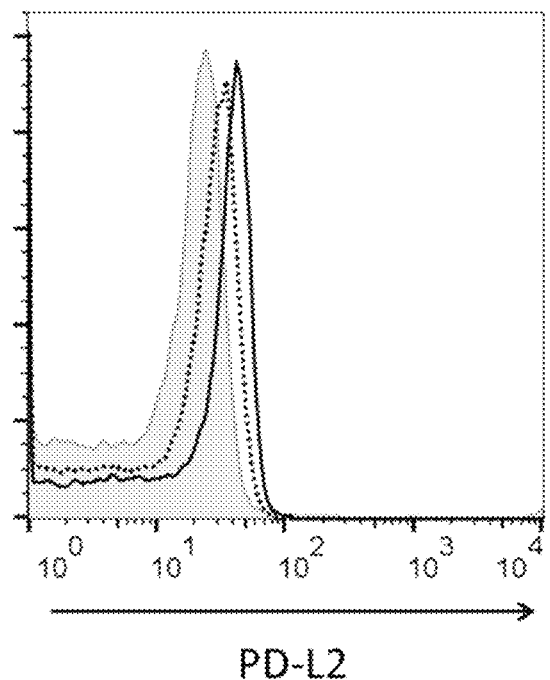
Figure 1I:
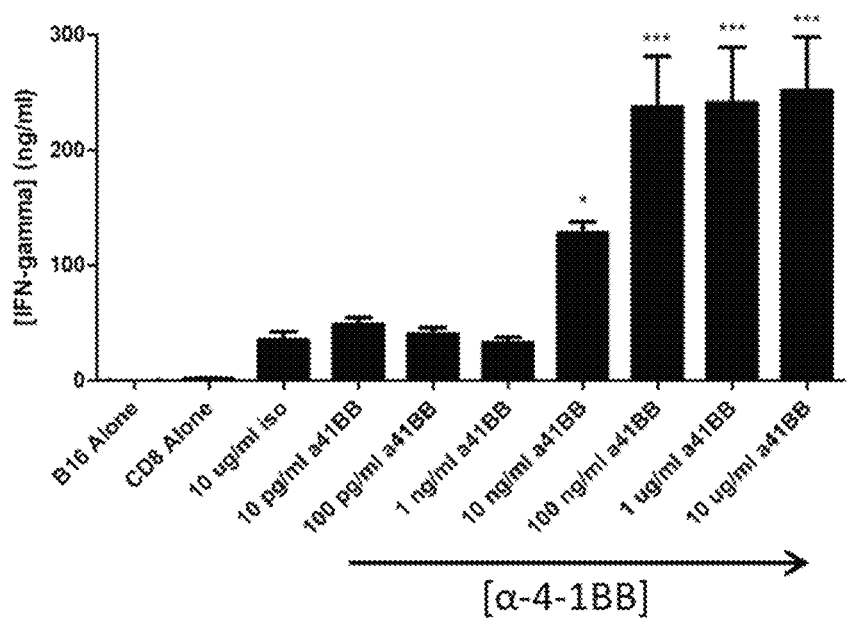
Figure 1J:
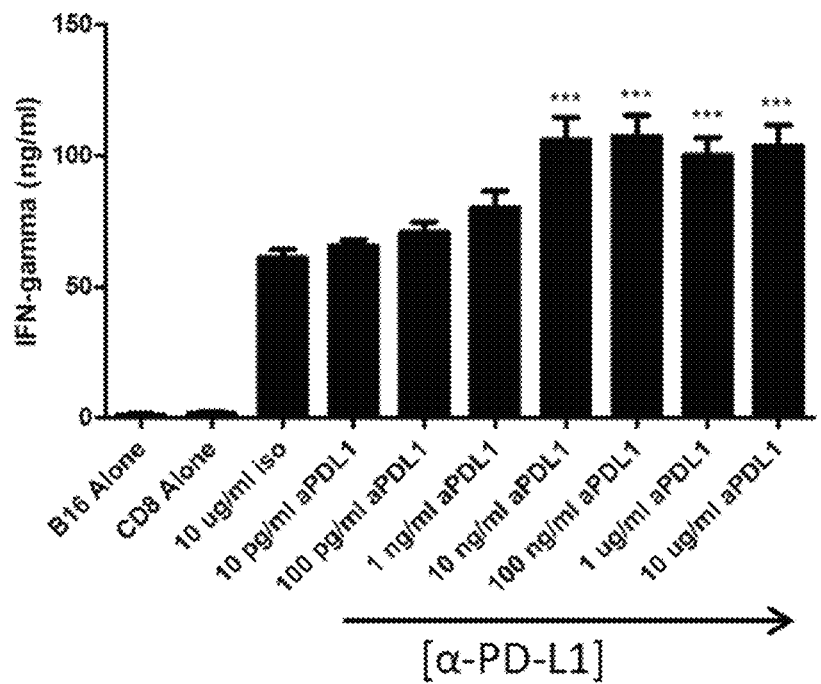

To study immunoswitch particle activity in vitro, we adapted a model of repetitive antigen stimulation which is known to upregulate expression of PD-1 on T cells, thus mimicking the tumor microenvironment[33]. 2C TCR transgenic CD8+ T cells, specific for the peptide SIY presented in the context of H-2 Kb, were stimulated with anti-CD3/anti-CD28 expander beads at a 1:1 bead to cell ratio on days 0 and 4. As expected, this protocol upregulated PD-1 on the 2C CD8+ T cells on day 8 (FIG. 1E). 4-1BB, which is also known to be expressed by tumor infiltrating lymphocytes[34], was upregulated as well (FIG. 1E). Cognate B16-SIY cells, a murine melanoma cell line expressing the SIY antigen in the context of the tumor's H-2 Kb MHC, and non-cognate B16-F10 cells were treated with 20 ng/ml IFN-γ for 48 hours to upregulate expression of the inhibitory ligand for PD-1, PDL1 (FIG. 1F, FIG. 1G). An irrelevant cell surface molecule, PD-L2, was not increased after INF-γ treatment (FIG. 1H). This model of upregulated PD-1 and 4-1BB on CD8+ T cells and high PDL1 expression on tumor cells has been used to study the T cell response in vitro in a system which mimics the tumor microenvironment. Both soluble anti-4-1BB monoclonal antibody (mAb) and anti-PDL1 mAb were confirmed to increase CD8+ cell activation in a dose dependent manner in this system (FIG. 1I, FIG. 1J).

Figure 1K:
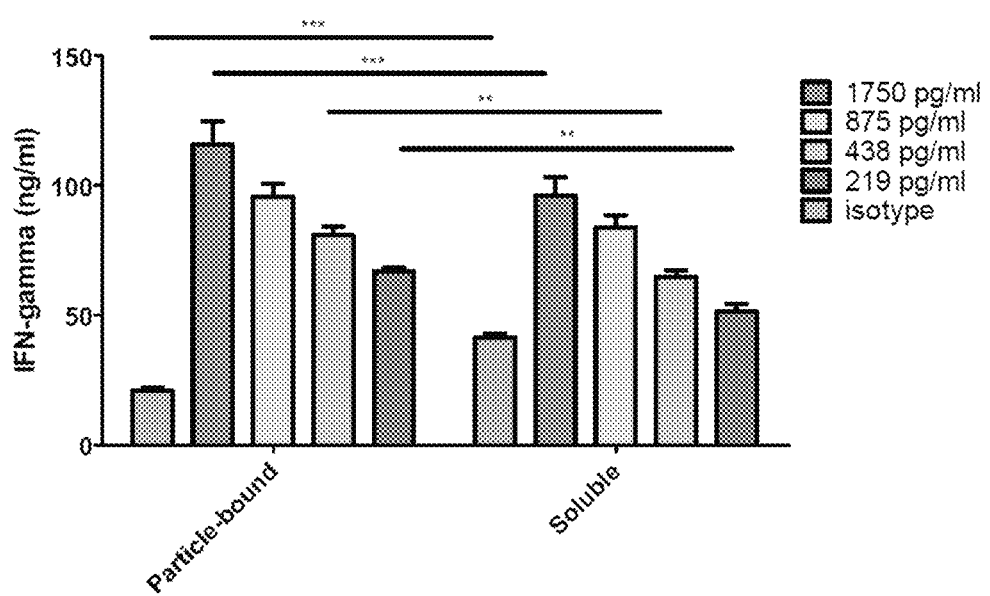

PD-1$^{hi}$ CD8+ T cells and PDL1$^{hi}$ B16-SIY cells were co-incubated with immunoswitch particles and T cell stimulation was measured by IFN-γ secretion. A dose dependent response was seen in cultures treated with immunoswitch particles (FIG. 1K). Compared to cultures treated with isotype control particles, there was over a 6 fold increase in IFN-γ secretion by immunoswitch particle-treated cultures (FIG. 1K). As expected, cultures treated with soluble anti-4-1BB and anti-PDL1 also led to increased IFN-γ secretion, although only a 2 to 3 fold increase as compared to control soluble isotype treated cultures. Thus, immunoswitch particle treated cultures worked better than or comparable to soluble antibody treated cultures. This data shows that antibody functionality is not lost by fixation of the antibodies to nanoparticles and in fact potentially improved.

Figure 1L:
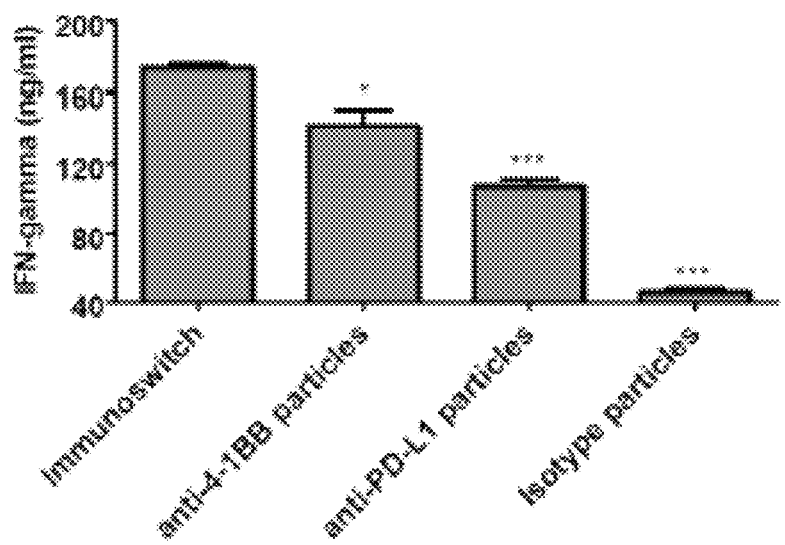

To investigate the requirement for both antibodies on the surface of the particle, we compared CD8+ T cell activation in response to co-incubation with immunoswitch particles, anti-4-1BB mAb only particles, or anti-PDL1 mAb only particles (FIG. 1L). Mechanistically, if stimulation is driven by antibody fixation to the nanoparticle resulting in increased avidity of one or both of the antibodies, we would expect one or the other individually-conjugated particles to have equal effectiveness to immunoswitch particles which have both. The greatest IFN-γ secretion, maximally 173±3 ng, was measured in immunoswitch particle treated cultures (FIG. 1L). In contrast, only 141±18 ng and 107±8 ng of IFN-γ was produced by cultures treated with anti-4-1BB and anti-PD-L1 only particles, respectively.

Example 10

Immunoswitch Particles Enhance T Cell-Tumor Cell Conjugation

To understand the mechanism of immunoswitch particle activity, we studied their cellular interactions. We sought to investigate both their ability to mediate CD8+ T cell-tumor cell conjugation as well as requirements for cognate peptide-MHC stimulation.

Figure 1M:
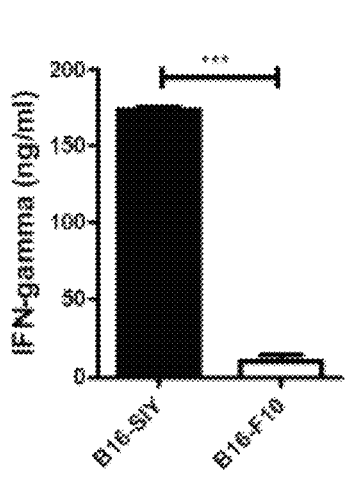
Figure 1N:
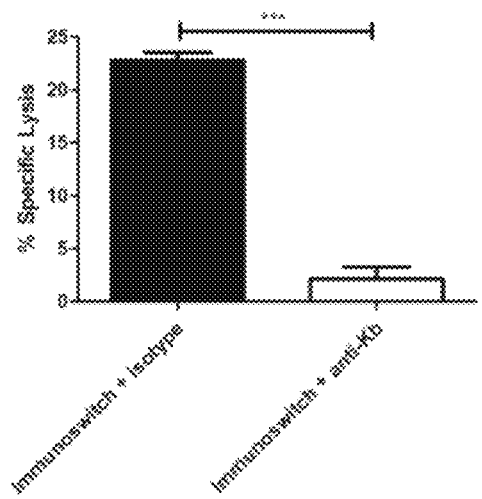

We investigated the requirement for peptide-MHC recognition by comparing 2C CD8+ T cell activation when co-incubated with immunoswitch particles and cognate B16-SIY or non-cognate B16-F10 tumor cells. In the presence of B16-SIY cells, immunoswitch particles resulted in robust IFN-γ secretion (FIG. 1M). There was no IFN-γ secretion in response to immunoswitch particles when 2C CD8+ T cells were stimulated with B16-F10 tumor cells lacking the cognate antigen. We further investigated the signal 1 dependence of immunoswitch activation by measuring cytotoxicity of cognate tumor cells in vitro. 2C CD8+ T cells were co-incubated with cognate B16-SIY cells, immunoswitch particles, and an anti-Kb mAb to block the signal 1 peptide-MHC interaction. At a 1:1 effector-target cell ratio, immunoswitch particles resulted in 22.8% specific lysis of B16-SIY cells (FIG. 1N). This was reduced to only 2.16% when an anti-Kb mAb was included during the co-incubation. Immunoswitch particle stimulation and cytotoxicity is dependent on the CD8+ T cell receiving a cognate signal 1 from the tumor cell itself.

In addition to requiring a cognate tumor cell for CD8+ T cell activation, we also investigated the hypothesis that immunoswitch particles increase effector-target cell conjugation. 2C CD8+ T cells and B16-F10 melanoma cells were labeled with a red and green membrane dye, respectively. Non-cognate B16-F10 cells were chosen to eliminate conjugate formation mediated by the T cell receptor-peptide-MHC interaction.

Figure 2A:
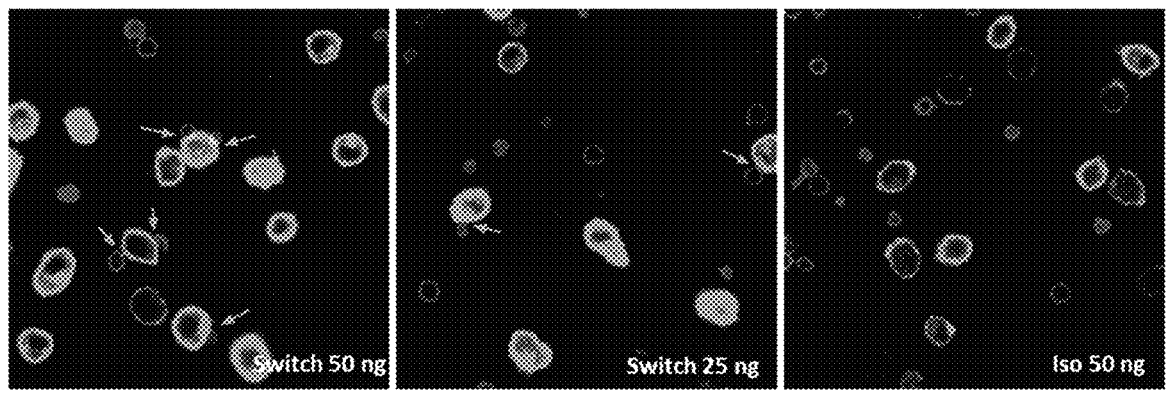
Figure 2B:
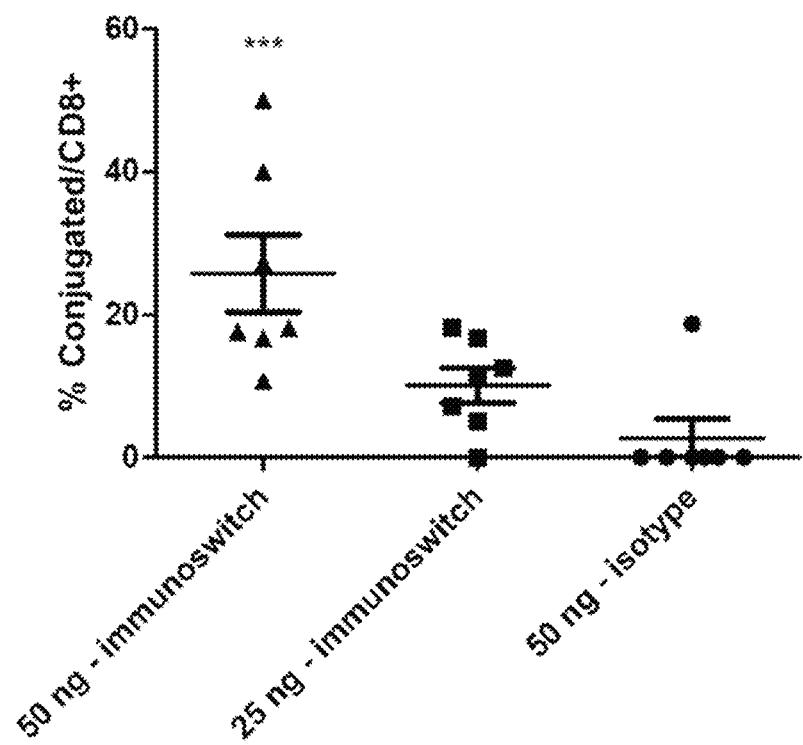

Labeled 2C CD8+ T cells and B16-F10 cells were co-incubated in the presence of immunoswitch or isotype particles. After 1 hour, cells were fixed and conjugate formation was measured by confocal microscopy or flow cytometry. Confocal microscopy showed an increase in effector-target cell conjugation mediated by immunoswitch particles (FIG. 2A, FIG. 2B). At a 420 ng/ml total antibody dose, immunoswitch particles resulted in significantly higher conjugate formation than isotype particles, nearing 30% of CD8+ T cells conjugated to tumor targets. Isotype particles resulted in minimal conjugate formation, indicating that PD-1/PD-L1 expression plays little to no role in effector-target cell conjugation in this system. These results of confocal microscopy were validated by a flow cytometry-based conjugation assay. 420 ng/ml of immunoswitch particles resulted in significantly greater effector-target cell conjugation as compared to isotype (FIG. 2D). These results indicate that immunoswitch particles increase conjugation by physically linking effector and target cells in an antigen independent fashion.

Example 11

Immunoswitch Particle-Activated CD8+ T Cells Receive Signal 1 from Cognate Tumor Cell We entertained two alternative hypotheses for how immunoswitch particles promote CD8+ T cell recognition of tumor cells. The first hypothesis is that the immunoswitch particles simply link the two cells and that obviates the need for cognate TCR-peptide-MHC interaction. Alternatively, while immunoswitch particles may link the two cells, cognate TCR-peptide-MHC interaction is still required for activation.

This was studied by comparing CD8+ T cell activation when co-incubated with the cognate tumor cell, B16-SIY, versus non cognate B16-F10 tumor cells which simply lack the cognate SIY antigen. Only in the presence of the cognate peptide-MHC-TCR interaction with B16-SIY cells do immunoswitch particles have activity (FIG. 1M). Thus, immunoswitch particle stimulation is signal 1-dependent as there was no CD8+ T cell stimulation in response to immunoswitch or control particles when the cells were stimulated with B16-F10 tumor cells expressing a non-cognate peptide-MHC signal 1 (FIG. 1M).

Example 12

Immunoswitch Particles Increase Effector-Target Cell Conjugation

Next we sought to investigate the mechanism by which immunoswitch particles link checkpoint blockade with co-stimulation to increase CD8+ T cell activation beyond that caused by soluble antibody. We hypothesized that combining both antibodies on a single platform may further increase CD8 cell activation by physically linking it to a target cell. The immunoswitch particles have antibodies against both 4-1BB, expressed by CD8 cells, and PDL1, expressed by tumor cells, and may increase conjugation between the two when both antibodies are bound simultaneously. We first investigated this question by asking whether the immunoswitch particles increase effector-target cell conjugation in vitro and thus increase the chance that a CD8 cell binds its target cell.

To test this hypothesis, 2C transgenic CD8 cells and non-cognate B16-F10 melanoma cells were labeled with a red and green membrane dye, respectively. Non-cognate B16-F10 cells were chosen to eliminate the signal 1 TCR-peptide-MHC interaction so that any effector-target cell conjugation could be attributed to the immunoswitch particles.

Labeled 2C CD8 cells and B16-F10 cells were combined at a 1:1 ratio in the presence of isotype particles or titrating doses of immunoswitch particles. After 1 hour, cells were fixed and conjugation formation was measured by confocal microscopy or flow cytometry. For confocal microscopy, conjugation formation was visually determined by overlap between the two cell types (FIG. 2A and FIG. 2B). At a 50 ng dose, immunoswitch particles resulted in significantly higher conjugate formation, nearing 30%, than isotype particles. Importantly, isotype particles resulted in almost no conjugate formation which is expected between a CD8 cell and non-cognate target cell.

Figure 2C:
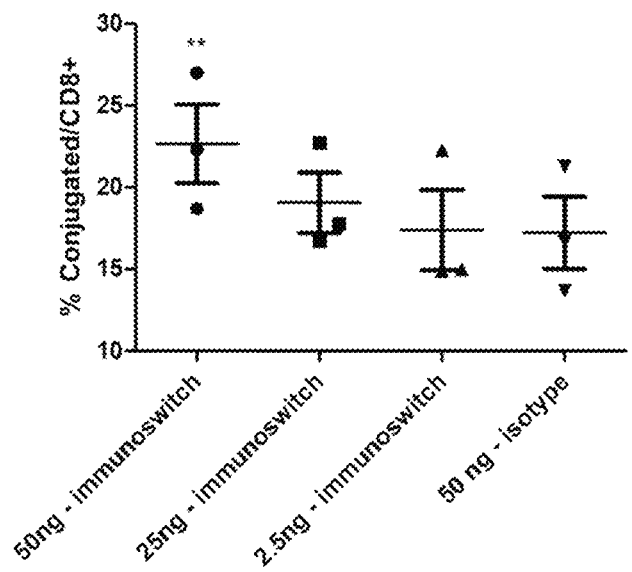
Figure 2D:
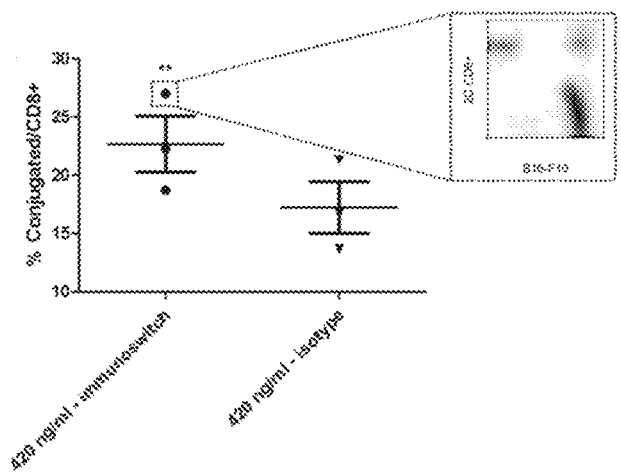

Similarly, conjugate formation was measured by gating on double red/green positive events on flow cytometry (FIG. 2C). Again, at 50 ng immunoswitch particles resulted in significantly greater effector-target cell conjugation as compared with isotype. These results show that the antibodies on immunoswitch particles have an additional effect past their interaction with cell signaling events—by combining both on the same platform, the particles also increase conjugation by physically linking effector and target cells.

Example 13

Immunoswitch Particles Inhibit Tumor Growth In Vivo

Because of the complexity of the tumors and their microenvironment, we investigated immunoswitch efficacy in vivo in multiple model systems. Our first model, based on our in vitro model system, entailed an adoptive transfer of a small number of PD-1$^{hi}$ cognate 2C CD8+ T cells into mice with pre-established B16-SIY melanoma tumors. Adoptively transferred cells were used as a model of exhausted tumor-specific cells that would likely be present in a patient's tumor microenvironment prior to treatment.

Figure 3A:
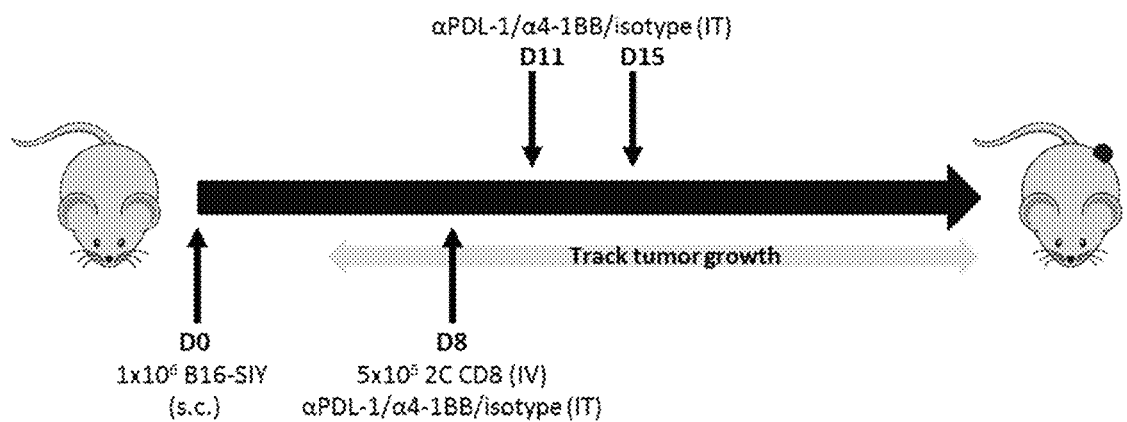

To study this, C57BL/6 mice were injected with B16-SIY tumor cells on day 0 and PD-1$^{hi}$ 2 C CD8+ T cells were adoptively transferred on day 8, except for a no treatment group (see schematic, FIG. 3A). Mice were then treated with immunoswitch particle on days 8, 11 and 15, or with various control regimens including: 1) no treatment, 2) CD8+ T cells only, 3) CD8+ T cells+ isotype-conjugated particle injection, or 4) CD8+ T cells+ soluble anti-4-1BB mAb+ soluble anti-PDL1 mAb. All treatment groups received a total of 1.3 ug of antibody per mouse per treatment intratumorally, approximately 100-fold less than the amount typically used for systemic intraperitoneal treatment. Tumor size was measured every 2-3 days and mice were sacrificed when tumor area was greater than 200 mm$^2$.

Figure 3B:
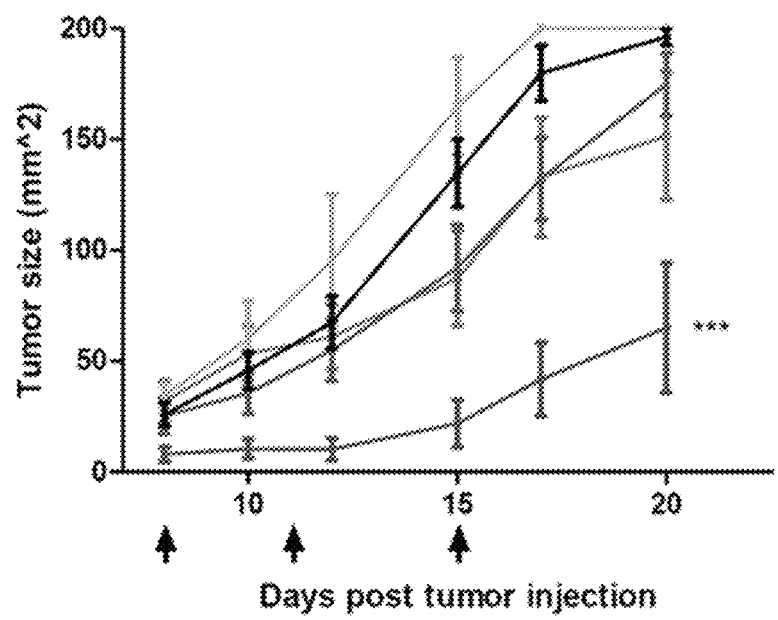
Figure 3C:
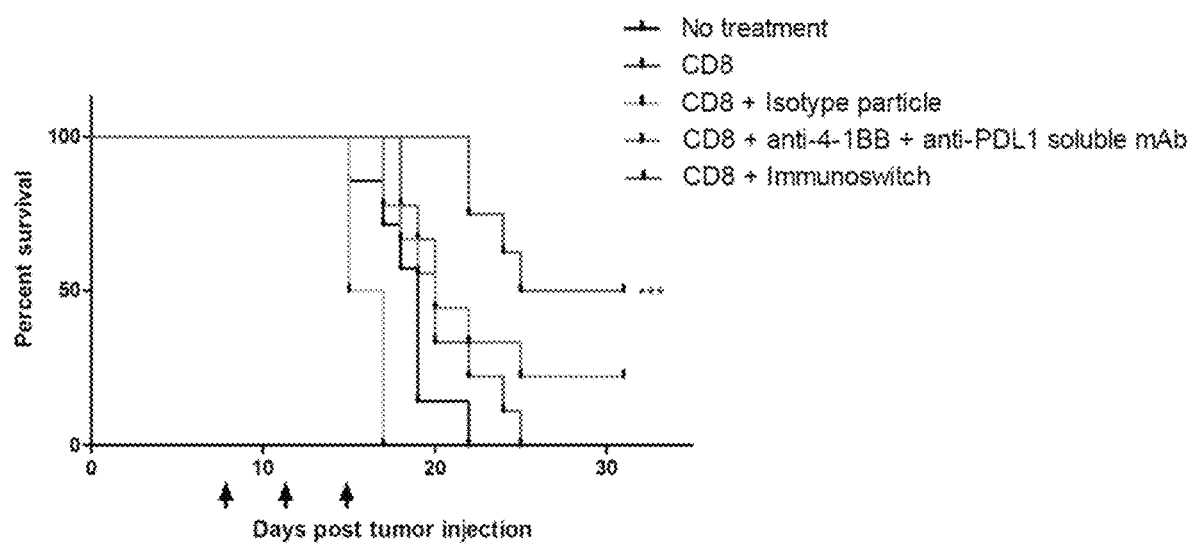

Only immunoswitch particle treatment significantly delayed tumor growth as compared to no treatment ($p<0.001$ by two way ANOVA with Bonferroni posttest). CD8+ T cell adoptive transfer alone, isotype particles, and soluble antibody did not result in any significant slowing of tumor growth (FIG. 3B). Immunoswitch particles were also the only treatment to significantly extend survival compared to no treatment ($p<0.001$ by Log-rank test) (FIG. 3C)—mice tended to die later or not at all. Soluble antibody also seemed to extend survival in a small number of mice, although this change was not significant.

Example 14

Immunoswitch Particles Target the Endogenous CD8 Cell Repertoire

If immunoswitch particles work by engaging and activating endogenous TILs, then we expect to see in vivo immunoswitch particle activity even in the absence of adoptively transferred CD8+ T cells. Thus in our second model, pre-established B16-SIY was developed to look at immunoswitch particle activity in the absence of adoptively transferred 2C CD8+ T cells.

Figure 4A:
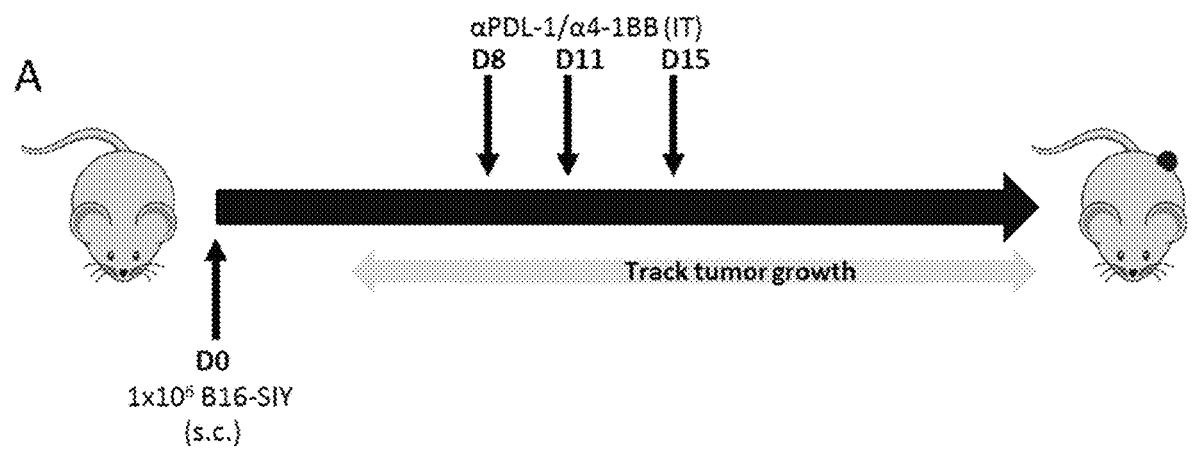

C57BL/6 mice were injected subcutaneously with B16-SIY tumors and treated, as before, on days 8, 11, and 15, when all mice had palpable tumor (FIG. 4A, schematic). Control groups for this experiment included no treatment or animals co-injected with a mixture of anti-4-1BB only and anti-PDL1 only particles. This second control was entertained to determine if the fact that the antibodies are immobilized on a rigid platform contributes to their efficacy—if the nanoparticles remaining at the injection site longer contribute to the in vivo activity, we would expect immunoswitch particles and the co-injection to act equivalently. However, if the presence of the antibodies on the same particle is important for effector-target killing by endogenous TILs, then we expect only immunoswitch particles to delay tumor growth.

Figure 4B:
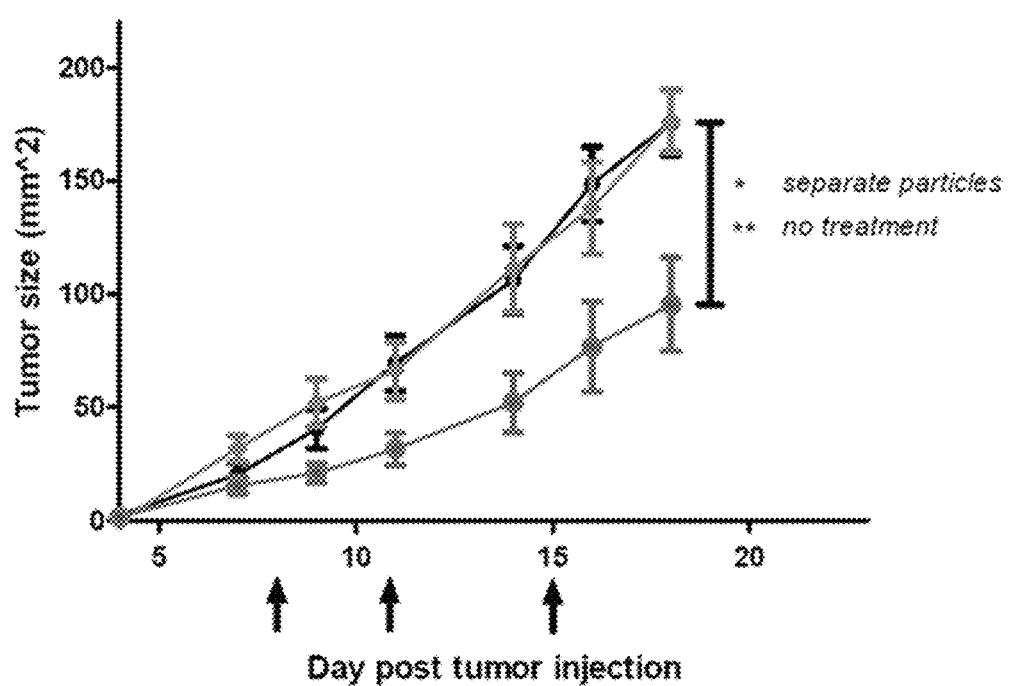
Figure 4C:
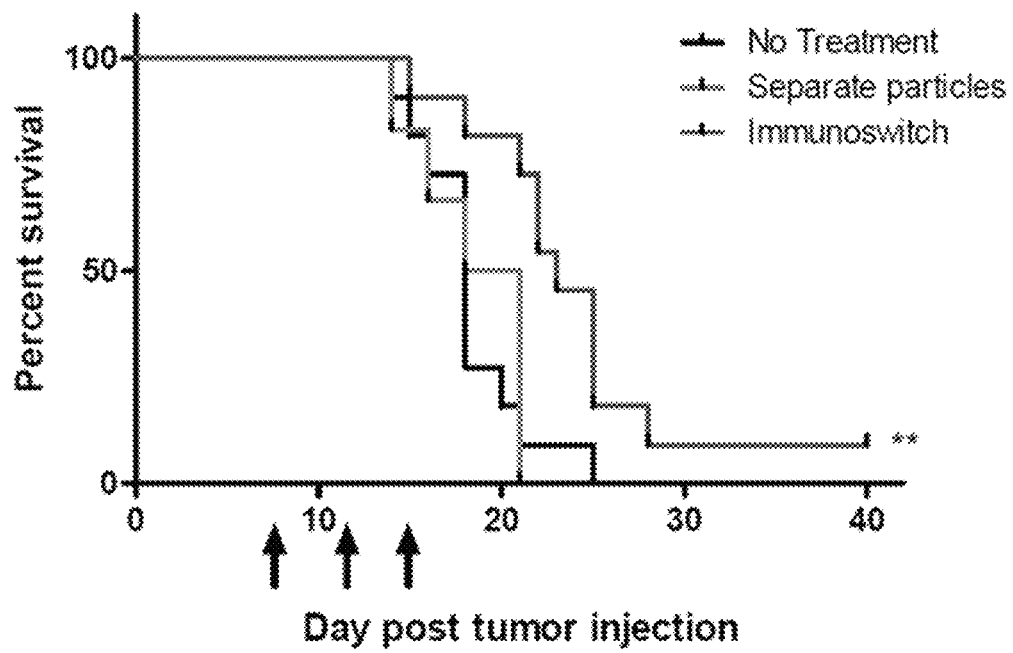
Figure 4D:
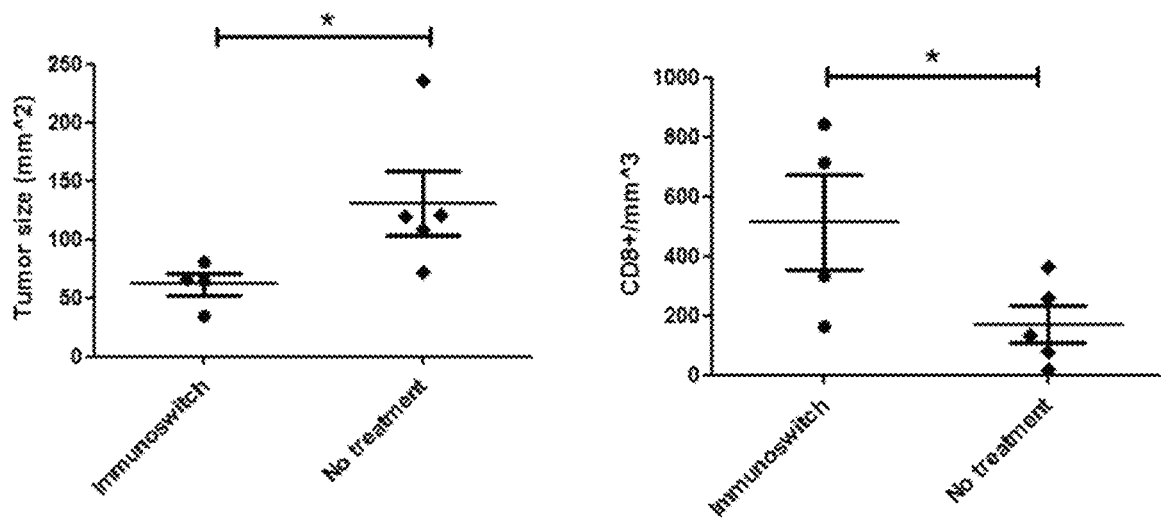
Figure 4E:
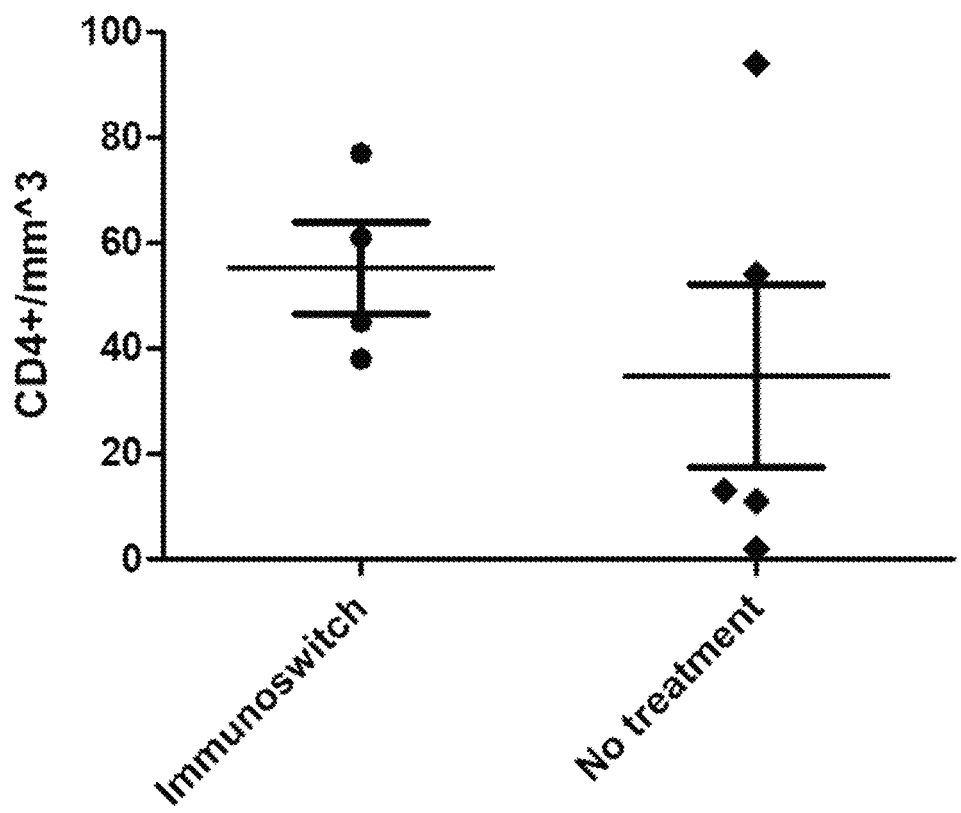
Figure 4F:
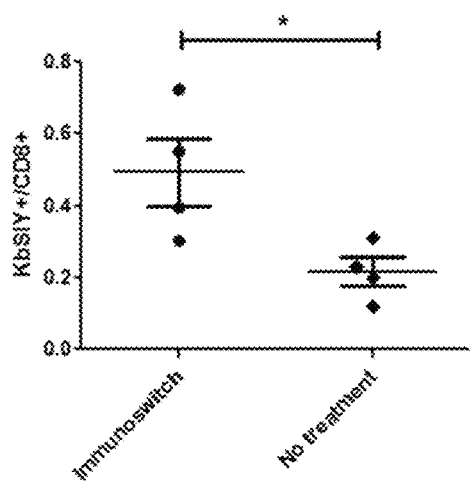
Figure 4G:
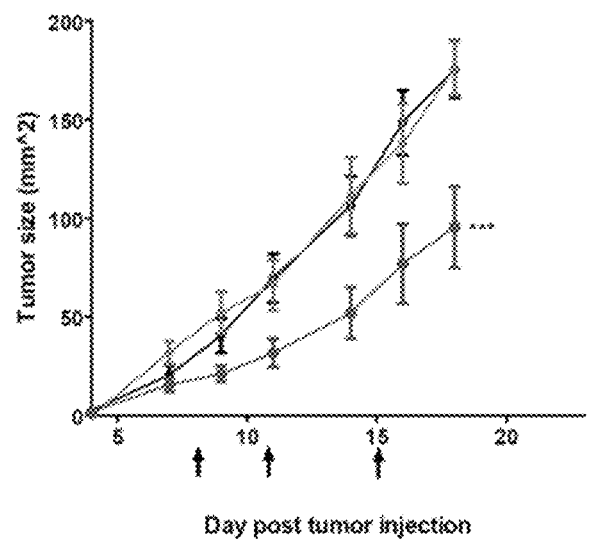

Only immunoswitch treated animals had delayed tumor growth and extended survival as compared to no treatment and control treated animals (FIG. 4B and FIG. 4C and FIG. 4G). This indicates that immunoswitch particles stimulate the endogenous repertoire of CD8+ T cells in TILs. Also, the rigid platform alone is not responsible for enhanced tumor control—both cell types must be engaged by the same particle. Delayed tumor growth in immunoswitch particle treated animals indicates that immunoswitch treatment targets polyclonal T cells already present within the tumor which can be rescued and re-activated without a prior knowledge of their antigen specificity.

Because the immunoswitch particles have antibodies on their surface against molecules expressed by both CD8+ and CD4+ T cells, we analyzed both cell types in TILs and tumor draining lymph nodes in immunoswitch treated animals. C57BL/6 mice (n=5/group) were injected with B16-SIY tumor on day 0, and assigned to one of two groups—no treatment or immunoswitch particles. Immunoswitch particles were administered days 8 and 11 and tumors and tumor draining lymph nodes were harvested and analyzed on day 14.

Figure 4H:
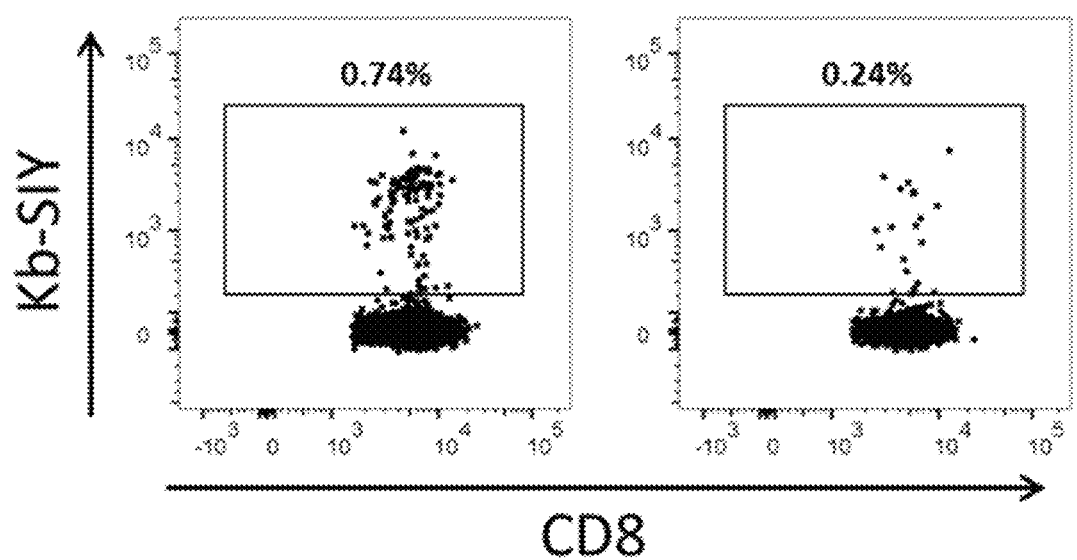

As expected, tumor size followed the same trend as in past experiments, where immunoswitch particle treated mice had significantly smaller tumors (FIG. 4D). TILs were stained for antibodies against CD4 and CD8, and total numbers of these subtypes were analyzed. CD8 cell density increased more than double in the immunoswitch treated group compared to no treatment (FIG. 4D), while CD4 density remained unchanged (FIG. 4E). The impact of immunoswitch treatment on antigen-specific CD8 cells was analyzed by determining the amount of T cells that recognize the Kb-SIY MHC complex, a tumor-specific cognate complex presented by B16-SIY tumors. There was a greater percentage of Kb-SIY positive CD8 cells within the tumor draining lymph nodes in immunoswitch treated animals (FIG. 4F and FIG. 4H). Together, this data indicates that CD8 cells but not CD4 cells are targeted by immunoswitch particles, consistent with the findings that anti-4-1BB primarily targets the CD8 T cells[35], and that they act to increase the number and specificity of CD8 cells within the tumor microenvironment.

To mechanistically study how immunoswitch particles activate an immune response, we analyzed tumor-infiltrating lymphocytes and tumor draining lymph nodes of immunoswitch treated animals. C57BL/6 mice were injected with B16-SIY tumor on day 0. Immunoswitch particles were administered days 8 and 11 and tumors and tumor draining lymph nodes were harvested and analyzed on day 14.

Figure 9A:
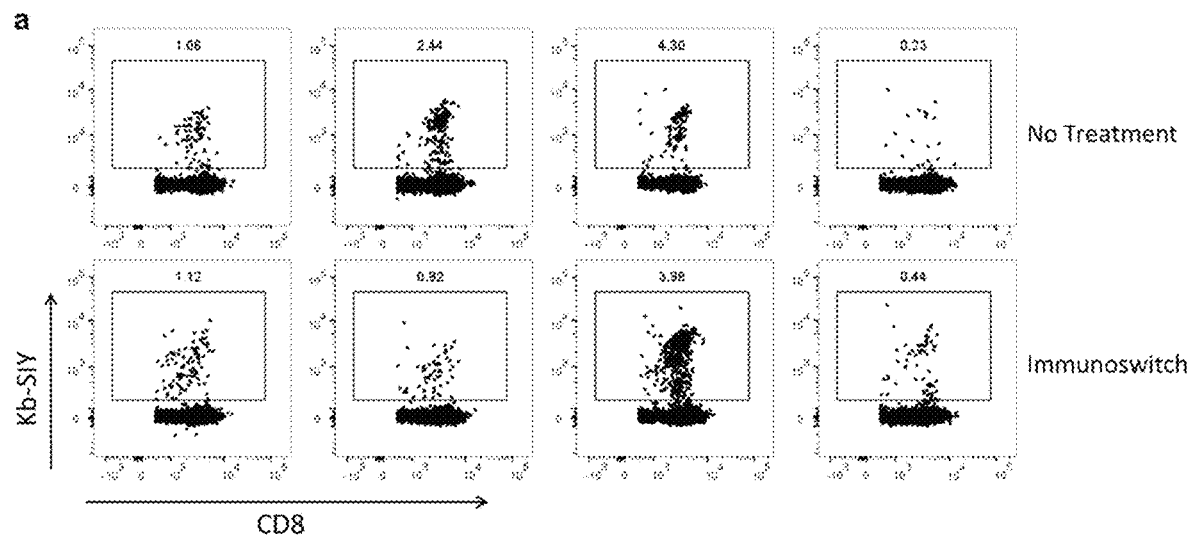
FIG. 9A and FIG. 9B shows that tumor specific CD8+ T cells are present in the periphery at the same levels in treated and non-treated mice.
Figure 9B:
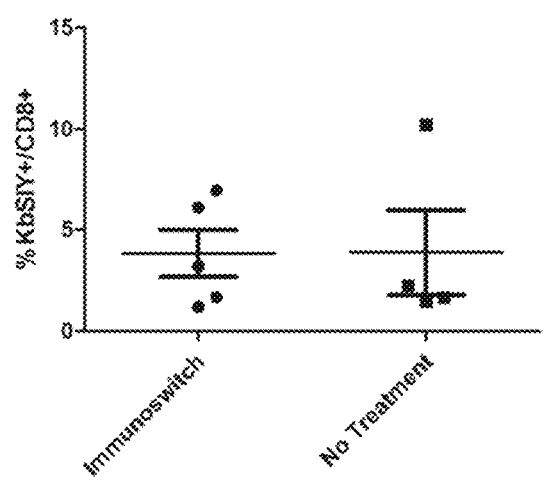

As expected, immunoswitch treated mice had significantly smaller tumors (FIG. 4D). The density of CD8+ T cells within the tumor-infiltrating lymphocytes compartment more than doubled in the immunoswitch treated group compared to no treatment (FIG. 4D), while CD4+ T cell density remained unchanged (FIG. 4E). The impact of immunoswitch treatment on antigen-specific T cells was analyzed by determining the Kb-SIY-specific CD8+ T cell response to the B16-SIY tumors. There were approximately double the percentage of Kb-SIY positive CD8+ T cells within the tumor draining lymph node of immunoswitch treated animals compared to non-treated animals-0.49±0.2% and 0.22±0.1%, respectively (FIG. 4F, FIG. 4H), while no difference in Kb-SIY positive CD8+ T cells were seen within the spleen, peripheral blood (FIG. 9), or tumor-infiltrating lymphocytes (FIG. 10).

Since immunoswitch treated mice have significantly delayed tumor growth, we hypothesized that treatment may increase the functionality of tumor infiltrating lymphocytes. To study the functionality of Kb-SIY+CD8+ tumor-infiltrating lymphocytes following immunoswitch treatment, mice were treated and tumor-infiltrating lymphocytes harvested on day 14 as above. Tumor-infiltrating lymphocytes were re-stimulated in vitro with SIY pulsed RMA-S cells and cytokine and CD107 production analyzed.

Immunoswitch treated animals had more than double the percentage of CD8+ tumor-infiltrating lymphocytes expressing CD107, a degranulation marker and indicator of the ability of T cells to lyse target tumor cells (FIG. 11A). CD8+ tumor-infiltrating lymphocytes also produced more IFN-γ compared to tumor-infiltrating lymphocytes from non-treated mice (FIG. 11B, FIG. 11C). This was seen by both an increase in the percent of IFN-γ+ cells (FIG. 11B) and a 38% increase in the mean fluorescence intensity of IFN-γ+ cells, indicating greater per-cell production (FIG. 11C). Together, these data indicate that immunoswitch particles stimulate an anti-tumor CD8+ T cell response by increasing their density, local tumor specificity, and in vivo functionality, consistent with findings that anti-4-1BB mAb primarily targets CD8+ T cells.

Example 15

Immunoswitch Particles Remain at Injection Site Longer than Soluble Antibody

Next, we sought to understand the pharmacokinetics of immunoswitch particles in vivo. Because immunoswitch particles are much larger than soluble antibody, we hypothesized that they would diffuse away from the injection site more slowly and thus result in a higher average treatment concentration over time.

Figure 5A:
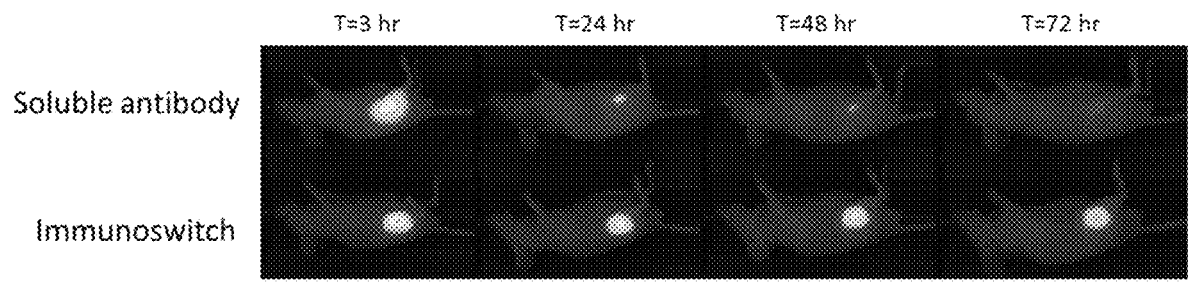
Figure 5B:
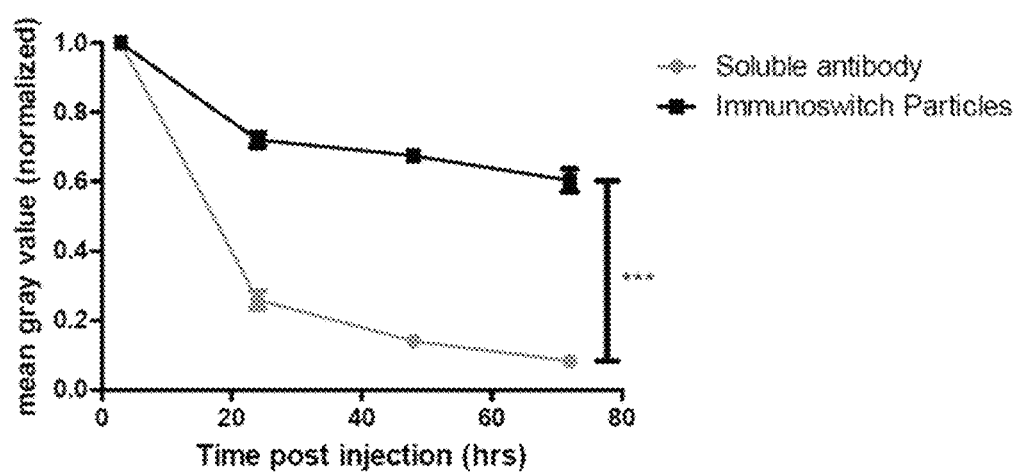

To investigate this, immunoswitch particles or an equivalent amount of soluble anti-4-1BB an anti-PDL1 antibody were labeled with an infrared (IR) dye and injected subcutaneously into nude mice (n=3/group). Mice were imaged using a full body IR imager after 3, 24, 48, and 72 hours to quantify the biodistribution of the particles and soluble antibody. Analysis was performed by defining a region of interest around the injection site and tracking the change in mean gray value from 3 hours (FIG. 5A and FIG. 5B).

Soluble antibody was cleared from the injection site significantly quicker than immunoswitch particles. By 24 hours, approximately 72% of immunoswitch particles remained at the injection site, while only 26% of soluble antibody remained at the injection site. Within 72 hours, this decreased to 60% of immunoswitch particles and 8% of soluble antibody. Thus, the prolonged retention of the immunoswitch particles at the tumor site may lead to their increased efficacy over soluble antibody.

Similarly sized nanoparticles have been shown to drain to the proximal tumor draining lymph node following intratumoral injection but not to more distal sites, minimizing systemic toxicity. We therefore examined the organ biodistribution of immunoswitch particles following intratumoral injection. C57BL/6 mice were injected with IR-labeled immunoswitch particles 8 days after B16-SIY tumor inoculation. 48 hours after treatment, the tumor, tumor draining lymph node, contralateral lymph node, and spleen were dissected and imaged by an IR imager. Immunoswitch particles were found in the tumor and tumor draining lymph node (FIG. 13), consistent with our finding that tumor-specific CD8+ T cells are present at higher levels in the tumor draining lymph node of immunoswitch treated mice. There were little to no detectable levels immunoswitch particles in the contralateral lymph node or spleen. Prolonged retention of the immunoswitch particles at the tumor site and tumor draining lymph node may contribute to their increased efficacy over soluble antibody. This sequestration of immunostimulatory ligands in the tumor site is consistent with the findings of others in the development of nanocarriers for tumor microenvironment immunomodulation.

Example 16

Immunoswitch Particles Reverse Tumor Growth in Murine Colon Cancer Model

Figure 6A:
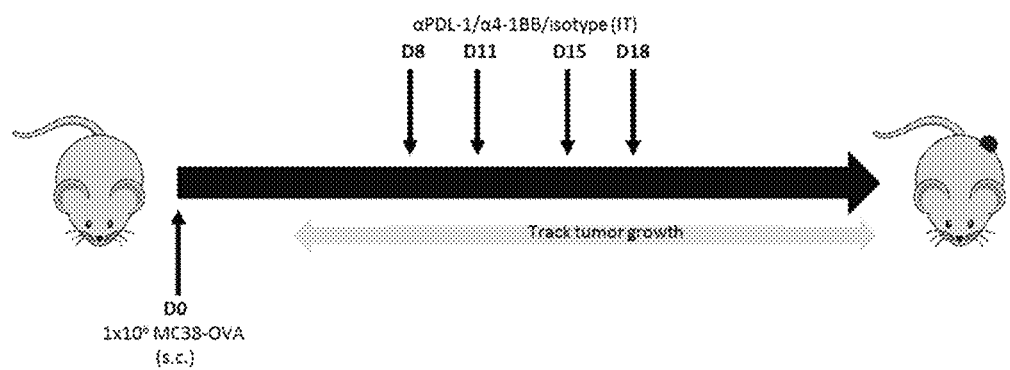

Lastly, we sought to investigate the effectiveness of immunoswitch particle treatment in another cancer model. We chose the MC38-OVA murine colon cancer line which expresses the Kb-OVA, but not Kb-SIY, peptide MHC. C57BL/6 mice (n=6-10/group) were injected subcutaneously with MC38-OVA tumors on day 0 and were assigned to one of three groups: 1) no treatment, 2) isotype particles, or 3) immunoswitch particles. Particle-treated mice received intratumoral injections on days 8, 11, 15, and 18, and tumors were measured every 2-3 days (FIG. 6A).

Figure 6B:
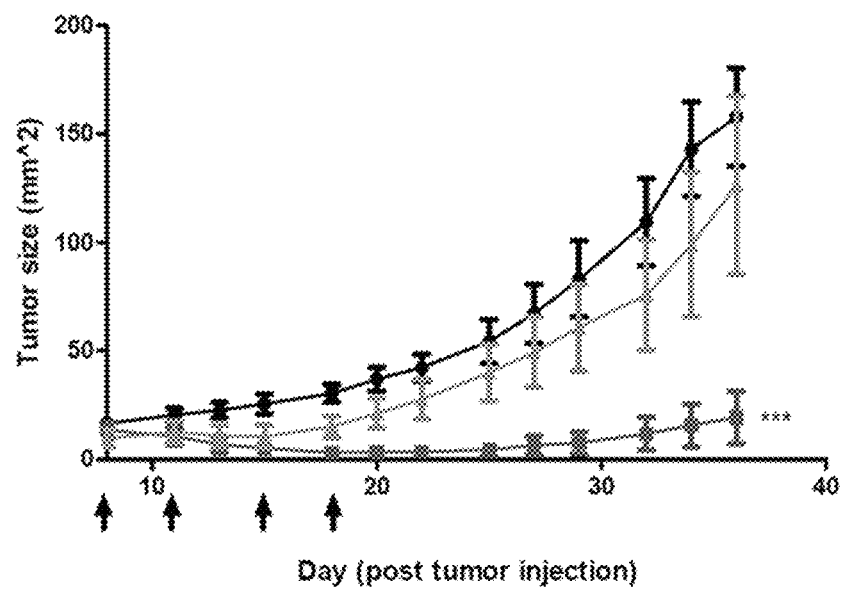
Figure 6C:
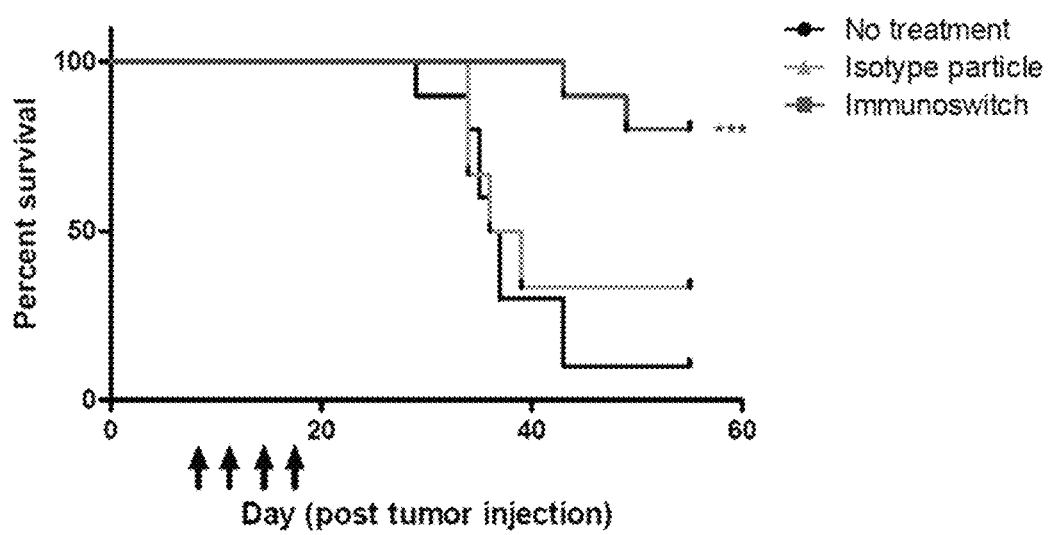

Only immunoswitch particle treated mice had significantly delayed tumor growth, averaging 19 mm$^2$ on day 36, as compared to 158 mm$^2$ for non-treated mice and 126 mm$^2$ for isotype treated mice (FIG. 6B). 70% of immunoswitch-treated mice survived past day 55, as compared with 10% of non-treated mice and 33% of isotype treated mice (FIG. 6C). These effects were even more pronounced than those seen in the B16-SIY model.—four doses of immunoswitch particles alone were able to reverse tumor growth in mice with palpable colon cancer tumors. The MC38-OVA cell line also expresses different peptide-MHC from B16-SIY, demonstrating the robustness of immunoswitch treatment. Again, this study lacked any adoptively transferred cells and demonstrates the ability for immunoswitch particles to activate the endogenous repertoire and mount an effective anti-tumor response as a single treatment strategy.

Example 17

We have developed immunoswitch particles that convert a blockade of tumor-expressing inhibitory signals to the delivery of a T cell stimulatory signal, such as 4-1BB ligand (FIG. 1B and FIG. 1C). To accomplish this, we conjugate 80 nm iron dextran nanoparticles with agonistic antibodies against 4-1BB (found on the effector T cells) and antagonistic antibodies against PDL1 (found on the cancer cells). Anti-biotin antibody-coated particles are purchased, and biotinylated anti-PDL1 and anti-4-1BB antibodies (clone 10F.9G2 and 3H3, respectively) are bound to their surface (FIG. 1B). The number of particle-bound molecules is quantified using a fluorescently labeled secondary antibody (FIG. 1C).

Efficacy of the immunoswitch particles was first confirmed in an in vitro chronic CD8 cell activation model. We chose to focus on CD8 T cell activation since 4-1BB has been shown to primarily activate this T cell subtype. Briefly, CD8 cells were harvested from 2C TCR transgenic (all CD8 cells recognize the Kb-SIY peptide-MHC complex) splenocytes. CD8 cells were stimulated on days −8 and −4 with a 1:1 ratio of anti-CD3/anti-CD28 artificial antigen presenting cells (aAPCs) to cause upregulation of PD-1 and 4-1BB on day 0 (FIG. 1E). B16-SIY murine melanoma cells expressing the Kb-SIY cognate 2C peptide MHC complex were incubated with 20 ng/ml IFN-γ on day −2 to upregulate PDL1 expression on day 0 (FIG. 1F).

On day 0, CD8 and B16-SIY cells were isolated from aAPCs and IFN-γ, respectively, and co-incubated with immunoswitch particles or an equivalent amount of soluble antibody to compare efficacy. CD8 cell stimulation was measured by IFN-γ secretion by ELISA after 18 hours. Immunoswitch particles stimulated CD8 cells just as well or better at all doses studied (FIG. 1K). To investigate the requirement for both antibodies on the surface of the particle, we compared CD8 cell activation in response to co-incubation with immunoswitch particles, anti-4-1BB only particles, or anti-PDL1 particles (FIG. 1L). Immunoswitch particles resulted in the greatest IFN-γ secretion, indicating that both antibodies are necessary. Importantly, we show that particle-stimulation is signal 1 dependent, as there was no CD8 cell stimulation in response to immunoswitch particles in the presence of B16-F10 cells expressing a non-cognate peptide-MHC signal 1 (FIG. 1L).

In addition to combining checkpoint blockade with CD8 cell co-stimulation, immunoswitch particles also enhance effector-target cell conjugation to increase T cell cytotoxicity. PD-1$^{hi}$ 2 C CD8 cells and PDL1$^{hi}$ B16-F10 cells were labeled with a red and green membrane dye, respectively. Effector and target cells were co-incubated for one hour in the presence of immunoswitch particles or isotype particles, fixed, and conjugate formation was quantified by two independent methods. First, conjugate formation was visually inspected and quantified by confocal microscopy (FIG. 2A, FIG. 2B). Secondly, conjugates were quantified by measuring the percentage of double (red and green) positive events by flow cytometry (FIG. 2C). In all cases, the highest dose of immunoswitch particles (50 ng) resulted in significantly increased effector-target cell conjugation as compared to isotype particles.

Immunoswitch particles have been shown to significantly delay tumor growth in an in vivo murine melanoma model. To investigate this, wild-type C57BL/6 mice were given B16-SIY tumors subcutaneously on day 0, and PD-1$^{hi}$ cognate 2C CD8 cells eight days later (FIG. 3A). On days 8, 11, and 15, mice were treated intratumorally with immunoswitch particles, an equivalent amount of soluble antibody, isotype particles, or no treatment in addition to the adoptively transferred cells. Tumors were measured every 2-3 days (FIG. 3B). Only immunoswitch particles significantly delayed tumor growth and extended survival as compared to non-treated mice. Isotype particles and soluble antibody had no effect.

Figure 7A:
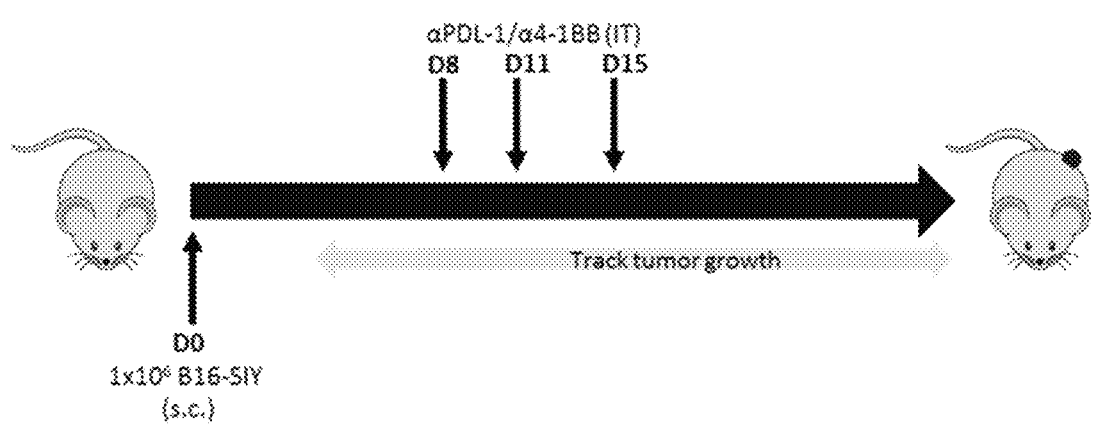
Figure 7B:
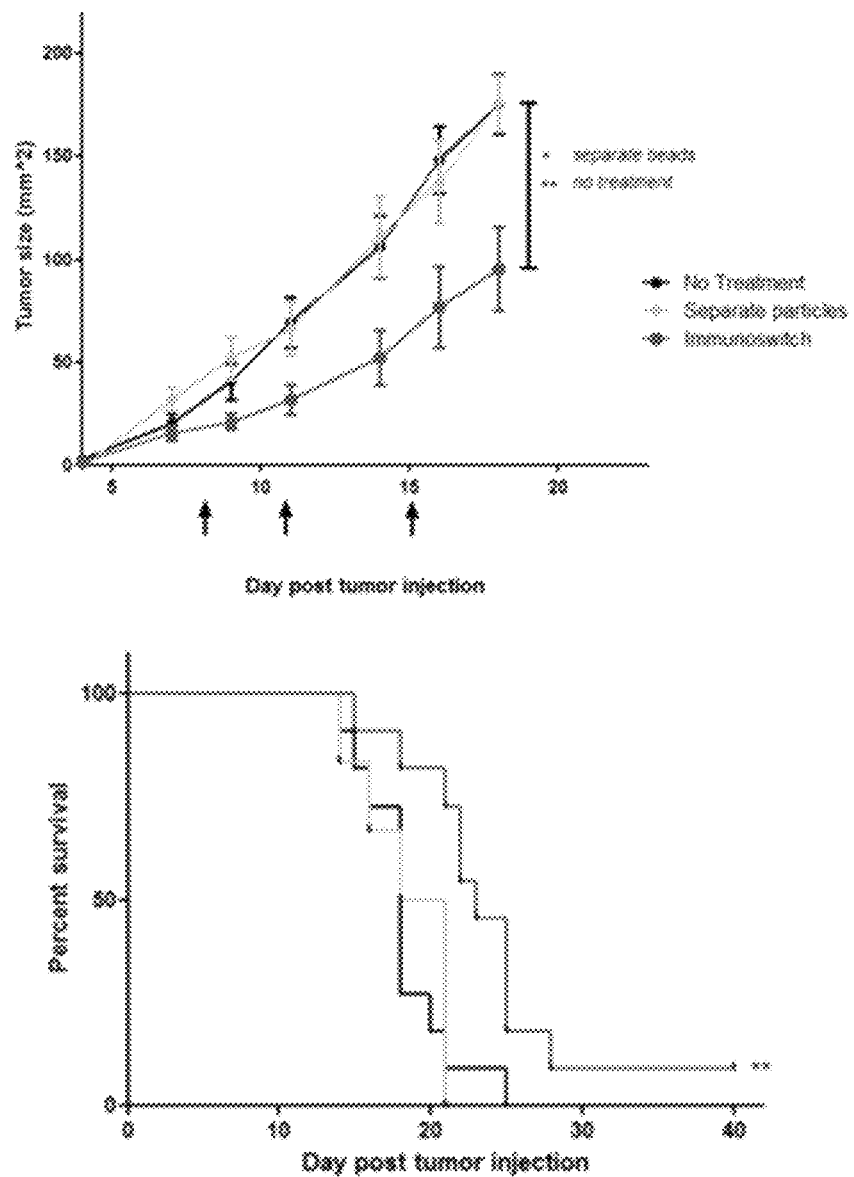

To investigate whether immunoswitch particles are superior to soluble antibody simply because the antibodies are conjugated to a rigid platform, or if it is necessary for the antibodies to be present on the same particle for increased conjugation, we compared immunoswitch particles to a mixture of anti-4-1BB only and anti-PDL1 only particles in vivo. C57BL/6 mice were injected with B16-SIY tumors subcutaneously on day 0, and given intratumoral treatments of immunoswitch particles or separate particles on days 8, 11, and 15 (FIG. 7A). Immunoswitch particles, but not co-injected anti-4-1BB and anti-PDL1 particles, delayed tumor growth and extended survival demonstrating the importance of these dual targeting antibodies being on the same particle.

Example 18

Experimental Setup

CD8+ cells were isolated from naïve mice at day 0 for co-incubation, and stimulated twice, including at day 4 using a 2:1 Dynal bead:cell ratio (aCD3/aCD28) and at day 8 using a 1:1 Dynal bead:cell ratio (aCD3/aCD28). Target tumor cells were incubated with 20 ng/ml IFN-γ for 48 hours prior to co-incubation. CD8+ cells and target cells isolated from aAPC and IFN-γ on D0 were co-incubated at a 1:1 effector: target cell ratio and particles were added at $4.67e^{11}$ beads/mL. After 18 hours, supernatant was harvested and IFN-γ release was quantified by ELISA.

In Vitro System Overview

A population of MC38-OVA cells express CD73 (~12%), and such population increases after IFN-γ treatment (~20%). MC38-OVA cells express high levels of PDL1 in response to IFN-γ treatment. OT-I CD8+ T cells express CD28, PD-1, and 4-1BB on day 0, after two stimulations on day 4 and day 8. Immunoswitch nanoparticles beads were tested, including anti-4-1BB/anti-PDL1 immunoswitch nanoparticles and anti-CD73/anti-4-1BB immunoswitch nanoparticles.

Results

Figure 8:
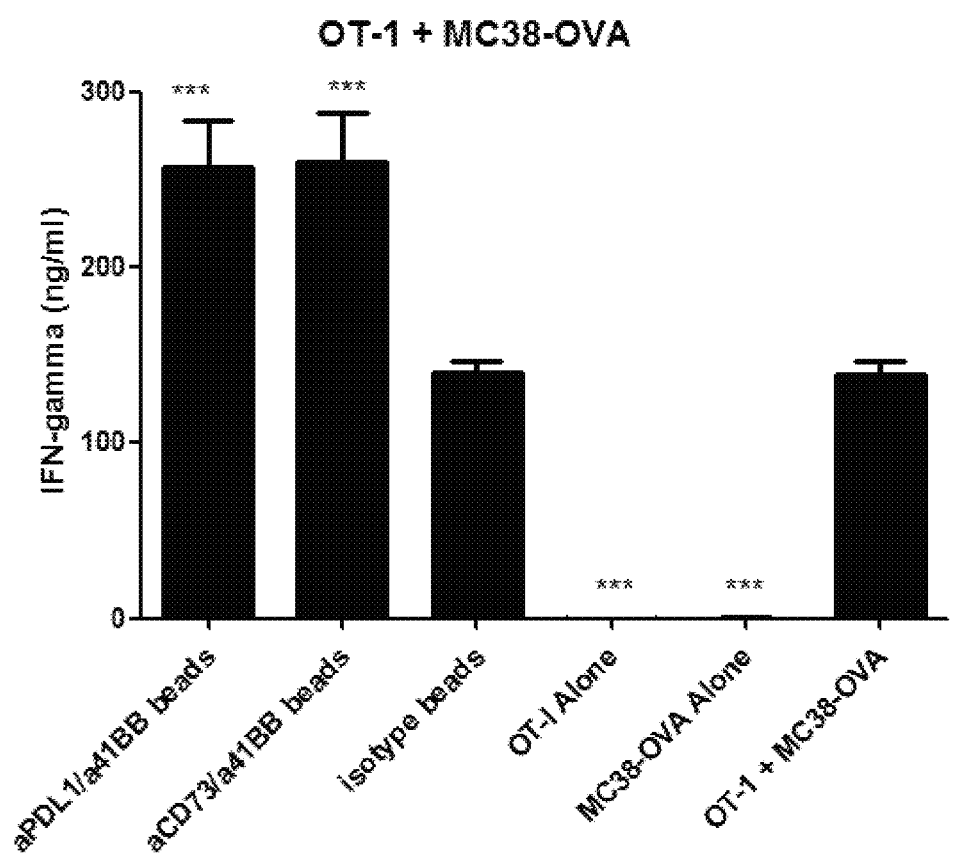
FIG. 8 shows that OT-I T cells secreted approximately 2-fold more IFN-γ in the presence of target cells and immunoswitch particles, as compared to target cells and isotype particles, for example, anti-CD73/anti-4-1BB particles increased IFN-γ secretion approximately 2-fold over isotype. Significance was measured by one-way ANOVA with Dunnett's posttest comparing all conditions to isotype beads.

As shown in FIG. 8, OT-I T cells secreted approximately 2-fold more IFN-γ in the presence of target cells and immunoswitch particles, as compared to target cells and isotype particles, for example, anti-CD73/anti-4-1BB nanoparticles and anti-PDL1/anti-4-1BB nanoparticles increased IFN-γ secretion approximately 2-fold over isotype.

Example 19

Immunoswitch Particles Alter the T Cell Receptor Repertoire

To gain a deeper understanding of the mechanism of action of immunoswitch particles, we analyzed the T cell receptor repertoire of the tumor infiltrating CD8+ T cells. As described above, tumors were harvested on day 14 and tumor-infiltrating CD8+ T cells were sorted and T cell receptors sequenced to determine amino acid sequence of the CDR3 region of the T cell receptor beta chains (T cell receptor V-beta). V-beta usage by the tumor-infiltrating lymphocytes of each treatment group was compared to usage in a naïve C57BL/6 mouse and to a Kb-SIY-specific response obtained by using a previously established CD8+ T cell activation protocol to expand Kb-SIY-specific cells from splenocytes of naïve C57BL/6 mice. After a 7 day stimulation, Kb-SIY+CD8+ T cells were sorted and sequenced (FIG. 10). As seen previously by Kb-SIY peptide-MI-IC staining of the tumor-infiltrating lymphocytes, the primary response of both immunoswitch-treated and tumor-bearing non-treated mice was dominated by V-beta 13 which is characteristic of a Kb-SIY response (FIG. 12A).

Despite the similarity in V-beta usage, the T cell receptor repertoire of these cells was significantly altered by immunoswitch treatment. T cell receptor clones, defined by the amino acid sequence of the CDR3 region, present in the tumor-infiltrating lymphocytes of immunoswitch treated mice appear at significantly lower levels in non-treated mice (FIG. 12B). Similarly, T cell receptor clones present in non-treated mice are present at significantly lower levels than in immunoswitch treated mice (FIG. 12B). This indicates that although a majority of the response both in the presence and absence of treatment is specific for the tumor-expressed Kb-SIY model antigen, the clones making up this response are changed by immunoswitch therapy.

Next, we investigated the conservation of this changed CD8+ T cell response after immunoswitch treatment. The clones that make up the majority of the response between pairs of immunoswitch-treated mice overlap by 44.1±4.3% (FIG. 12C). This contrasts with only 6.43±6.92% of an overlapping response between pairs of non-treated mice. Thus, immunoswitch particle treatment selects for a highly conserved anti-tumor response. This indicates that treatment delays tumor growth by inducing expansion of a specific population of anti-tumor CD8+ T cells with an altered T cell receptor sequence signature.

Example 20

Immunoswitch Particles Delay Tumor Growth when Injected Intravenously

The tumor models, B16-SIY and MC38-OVA, both express strong model foreign antigens. Thus, we next sought to investigate the efficacy of immunoswitch particle therapy in a less immunogenic tumor model, B16-F10, which is identical to B16-SIY except that it lacks expression of the Kb-SIY model foreign antigen, to demonstrate broader therapeutic relevance.

C57BL/6 mice were injected subcutaneously with B16-F10 tumors on day 0. Mice were treated with immunoswitch particles intratumorally on days 8, 11, and 15 and tumors were measured. Immunoswitch particle therapy resulted in significantly delayed tumor growth compared to non-treated mice (FIG. 14). By day 15, the tumor size was nearly halved by immunoswitch treatment—tumors averaged 112 mm² for immunoswitch-treated mice compared to 205 mm² for non-treated mice. Immunoswitch particle treatment also resulted in significantly extended survival compared to no treatment. This data demonstrates the broader applicability of immunoswitch particle therapy to less immunogenic tumor models.

Finally, we further investigated the route of administration by studying their effect on tumor growth when injected intravenously. C57BL/6 mice were injected subcutaneously with B16-SIY tumors and were treated with immunoswitch particles intravenously on days 4, 8, 11, and 15. Mice treated with immunoswitch particles intravenously were given one additional early dose on day 4, a standard time point used for checkpoint inhibition studies in the B16-SIY model. Intravenous treatment resulted in similar anti-tumor efficacy to our standard intratumoral treatment (FIG. 14). In contrast, similar doses of IV administered soluble antibody had no effect on tumor growth as was seen with intratumoral injection of soluble antibodies.

Example 21

Immunoswitch Particle Treatment Results in Systemic Immunity in Cured Animals

C57BL/6 mice were inoculated with 1×10$^6$ MC38-OVA murine colon cancer cells on day 0. Mice were treated intratumorally with immunoswitch particles on days 8, 11, 15, and 18. On day 28, mice that were either (1) cured (i.e. disappearance of palpable tumor), (2) not cured (i.e. palpable tumor) by treatment, or (3) never inoculated with MC38-OVA tumors, were injected retro-orbitally with fluorescently labeled OVA (cognate) and SIY (non-cognate) pulsed splenocytes. Mice were sacrificed and spleens were harvested after 18 hours. Killing of the OVA-pulsed splenocytes was measured by running the cells on flow cytometry.

The results (FIG. 15) indicate that after intra-tumoral treatment, animals that were "cured" (i.e., palpable tumor had disappeared) had developed systemic immune responses to the tumor. This indicates that (1) one lesion may be treated with an immunoswitch particle intra-tumorally and distant metastases would be cured; (2) immunoswitch treatment of a single lesion may lead to long term memory and immunosurveillance so that new tumors, even at distant sites, will not arise; and (3) immunoswitch treatment leads to antigen specific memory so that if a new tumor starts to develop that shares the same antigens, such as Her2, BRCA1, BRCA2, or K-Ras, immunoswitch treatment would slow or prevent new tumors from developing. A single solitary lesion may be treated intratumorally with the nanoparticles as detailed herein, and the nanoparticles may induce a systemic immune response. The systemic immune response may be due to memory immune responses. The nanoparticles may provide protection to the patient for any new tumors that could otherwise arise.

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Ahmad, M., Rees, R. C. & Ali, S. a. Escape from immunotherapy: Possible mechanisms that influence tumor regression/progression. *Cancer Immunol. Immunother.* 53, 844-854 (2004).

Ascierto, P. a. & Marincola, F. M. 2015: The Year of Anti-PD-1/PDL1s Against Melanoma and Beyond. *EBioMedicine* 2, 92-93 (2015).

Barrett, D. M., Singh, N., Porter, D. L., Grupp, S. A. & June, C. H. Chimeric Antigen Receptor Therapy for Cancer. *Annu Rev Med* 65, 333-347 (2014).

Barthkowiak T. and Curren M. A. 4-1BB Agonists: Multi-Potent Potentiators of Tumor Immunity. *Front Oncol.* 5: 117 (2015).

Beyersdorf, N., et al. Superagonistic anti-CD28 antibodies: potent activators of regulatory T cells for the therapy of autoimmune diseases. *Ann Rheum Dis.* 64:iv91-iv95 (2005).

Black C M, Armstrong T D, Jaffee E M. Apoptosis-Regulated Low-Avidity Cancer-Specific CD8+ T Cells Can Be Rescued to Eliminate HER2/neu-Expressing Tumors by Costimulatory Agonists in Tolerized Mice. *Cancer Immunol Res.* 2014; 2(4):307-319. doi:10.1158/2326-6066.CIR-13-0145.

Bono, M. R., Fernández, D., Flores-Santibáñez, F., Rosemblatt, M. & Sauma, D. CD73 and CD39 ectonucleotidases in T cell differentiation: Beyond immunosuppression. *FEBS Lett.* (2015). doi:10.1016/j.febslet.2015.07.027

Brahmer, J. R. et al. Safety and activity of anti-PDL1 antibody in patients with advanced cancer. *J. Urol.* 188, 2148-9 (2012).

Callahan, M. K. & Wolchok, J. D. At the bedside: CTLA-4- and PD-1-blocking antibodies in cancer immunotherapy. *J. Leukoc. Biol.* 94, 41-53 (2013).

Carreno, B. M. et al. A dendritic cell vaccine increases the breadth and diversity of melanoma neoantigen-specific T cells. *Science* 348, 1-9 (2015).

Chen, D. S. & Mellman, I. The Cancer-Immunity Cycle. 1-10 (2013). doi:10.1016/j.immuni.2013.07.012

Dal Porto, J. et al. A soluble divalent class I major histocompatibility complex molecule inhibits alloreactive T cells at nanomolar concentrations. *Proc. Natl. Acad. Sci. U S. A.* 90, 6671-5 (1993).

Freeman, G. J., Sharpe, A. H. & Kuchroo, V. K. Protect the killer: CTLs need defenses against the tumor. *Nat. Med.* 8, 787-9 (2002).

Gajewski T F, Schreiber H, Fu Y-X. Innate and adaptive immune cells in the tumor microenvironment. *Nat Immunol.* 2013; 14(10):1014-1022. doi:10.1038/ni.2703.

Gubin, M. M. et al. Checkpoint blockade cancer immunotherapy targets tumour-specific mutant antigens. (2014). doi:10.1038/nature13988

Gubin, M. M., Artyomov, M. N., Mardis, E. R. & Schreiber, R. D. Tumor neoantigens: building a framework for personalized cancer immunotherapy. *J Clin Invest* 125, 1-9 (2015).

Hurwitz A A, Cuss S M, Stagliano K E, Zhu Z. T cell avidity and tumor immunity: Problems and solutions. *Cancer Microenviron.* 2014; 7(1-2):1-9. doi:10.1007/s12307-013-0143-1.

Iwai, Y. et al. Involvement of PDL1 on tumor cells in the escape from host immune system and tumor immunotherapy by PDL1 blockade. *Proc Natl Acad Sci USA* 99, 12293-7 (2002).

Kamphorst, A. O. & Ahmed, R. Manipulating the PD-1 pathway to improve immunity. *Curr. Opin. Immunol.* 1-8 (2013). doi:10.1016/j.coi.2013.03.003

Karwacz, K. et al. PDL1 co-stimulation contributes to ligand-induced T cell receptor down-modulation on CD8+ T cells. *EMBO Mol. Med.* 3, 581-92 (2011).

Khong, H. T. & Restifo, N. P. Natural selection of tumor variants in the generation of [ldquo]tumor escape[rdquo] phenotypes. *Nat Immunol* 3, 999-1005 (2002).

Meyer, R. a et al. Biodegradable Nanoellipsoidal Artificial Antigen Presenting Cells for Antigen Specific T-Cell Activation. *Small* 11, 1519-1525 (2014).

Oelke, M. & Schneck, J. P. Overview of a HLA-Ig based 'Lego-like system' for T cell monitoring, modulation and expansion. *Immunol. Res.* 47, 248-56 (2010).

Peggs, K. S. & Quezada, S. a. PD-1 blockade: promoting endogenous anti-tumor immunity. *Expert Rev. Anticancer Ther.* 12, 1279-82 (2012).

Perica, K. et al. Nanoscale artificial antigen presenting cells for T cell immunotherapy. *Nanomedicine* 10, 119-29 (2014).

Pilon-Thomas, S., Mackay, A., Vohra, N. & Mule, J. J. Blockade of programmed death ligand 1 enhances the therapeutic efficacy of combination immunotherapy against melanoma. *J. Immunol.* 184, 3442-9 (2010).

Rabinovich, G. a, Gabrilovich, D. & Sotomayor, E. M. Immunosuppressive strategies that are mediated by tumor cells. *Annu. Rev. Immunol.* 25, 267-96 (2007).

Robert, C. et al. Anti-programmed-death-receptor-1 treatment with pembrolizumab in ipilimumab-refractory advanced melanoma: a randomised dose-comparison cohort of a phase 1 trial. *Lancet* 384, 1109-1117 (2014).

Robert, C. et al. Nivolumab in previously untreated melanoma without BRAF mutation. *N. Engl. J. Med.* 372, 320-30 (2015).

Rosenberg, S. A. & Restifo, N. P. Adoptive cell transfer as personalized immunotherapy for human cancer. *Science (80-.).* 348, 62-68 (2015).

Sasawatari, S. et al. Efficient priming and expansion of antigen-specific CD8+ T cells by a novel cell-based artificial APC. *Immunol. Cell Biol.* 84, 512-21 (2006).

Shen, C. et al. Latex bead-based artificial antigen-presenting cells induce tumor-specific CTL responses in the native T-cell repertoires and inhibit tumor growth. *Immunol. Lett.* 150, 1-11 (2013).

Shindo Y, Yoshimura K, Kuramasu A, et al. Combination Immunotherapy with 4-1BB Activation and PD-1 Blockade Enhances Antitumor Efficacy in a Mouse Model of Subcutaneous Tumor. *Anticancer Res.* 2015; 136:129-136.

Shuford W W, Klussman K, Tritchler D D, et al. 4-1BB costimulatory signals preferentially induce CD8+ T cell proliferation and lead to the amplification in vivo of cytotoxic T cell responses. *J Exp Med.* 1997; 186(1):47-55.

Topalian, S. L. et al. Safety, Activity, and Immune Correlates of Anti-PD-1 Antibody in Cancer. *New Engl. J. Med.* 366, 2187-2198 (2012).

Turtle, C. J. & Riddell, S. R. Artificial antigen presenting cells for use in adoptive immunotherapy. 16, 374-381 (2011).

Vasievich, E. a & Huang, L. The suppressive tumor microenvironment: a challenge in cancer immunotherapy. *Mol. Pharm.* 8, 635-41 (2011).

Weder, P., Schumacher, T. N. M., Spits, H. & Luiten, R. M. Testing for HLA/peptide tetramer-binding to the T cell receptor complex on human T lymphocytes. *Results Immunol.* 2, 88-96 (2012).

Yadav, M. et al. Predicting immunogenic tumour mutations by combining mass spectrometry and exome sequencing. *Nature* 515, 572-6 (2014).

Zhou, Q. et al. Blockade of programmed death-1 pathway rescues the effector function of tumor-infiltrating T cells and enhances the antitumor efficacy of lentivector immunization. *J. Immunol.* 185, 5082-92 (2010).

Soldevilla M. M., et al. Aptamers: A Feasible Technology in Cancer Immunotherapy. *J Immunol Res. doi:* 10.1155/2016/1083738; PMCID: PMC4931050 (2016).

Prodeus, A. et al. Targeting the PD-1/PD-L1 Immune Evasion Axis With DNA Aptamers as a Novel Therapeutic Strategy for the Treatment of Disseminated Cancers. *Molecular Therapy Nucleic Acids* 4, e237 (2015).

Santulli-Marotto S, et al. Multivalent RNA aptamers that inhibit CTLA-4 and enhance tumor immunity. *Cancer Res.* 63(21):7483-9 (2003).

Herrmann A., et al. CTLA4 aptamer delivers STAT3 siRNA to tumor-associated and malignant T cells. *The Journal of Clinical Investigation.* 124(7):2977-2987 (2014).

Arruebo M., et al. Antibody-Conjugated Nanoparticles for Biomedical Applications. *Journal of Nanomaterials.* Article ID 439389, (2009).

He L Z., et al. Agonist anti-human CD27 monoclonal antibody induces T cell activation and tumor immunity in human CD27-transgenic mice. *J Immunol.* 191(8):4174-83 (2013).

Mathan T S M, et al. Human Plasmacytoid Dendritic Cells: From Molecules to Intercellular Communication Network. *Front Immunol.* 4: 372 (2013).

De Paoli P, et al. Microenvironmental abnormalities induced by viral cooperation: Impact on lymphomagenesis. *Seminars in Cancer Biology* 34:70-80 (2015).

Although the foregoing subject matter has been described in some detail by way of illustration and example for purposes of clarity of understanding, it will be understood by those skilled in the art that certain changes and modifications can be practiced within the scope of the appended claims.

The invention claimed is:

1. An immunoswitch particle comprising a nanoparticle comprising:
   a first agent that indirectly modulates an immunosuppressive pathway in a tumor cell or immunosuppressive molecule induced by the tumor cell in the tumor microenvironment; and
   a second agent that simultaneously targets a co-stimulatory pathway or co-inhibitory pathway in a T cell,
   wherein the first agent is a CD73 antagonist antibody or a functional variant thereof that is a CD73 antagonist; and the second agent is a 4-1BB agonist antibody or a functional variant thereof that is a 4-1BB agonist.

2. The immunoswitch particle of claim 1, wherein the T cell is selected from the group consisting of a CD4+ T cell and a CD8+ T cell.

3. The immunoswitch particle of claim 1, wherein the nanoparticle has a diameter ranging from approximately 50 nm to approximately 100 nm.

4. The immunoswitch particle of claim 1, wherein the nanoparticle has a diameter of approximately 80 nm.

5. The immunoswitch particle of claim 1, wherein the nanoparticle has an increased retention time in a subject relative to the first agent alone, the second agent alone, a nanoparticle comprising the first agent alone, or a nanoparticle comprising the second agent alone.

6. An immunotherapy method of treating a cancer or a chronic viral infection in a subject in need thereof, the method comprising administering an effective amount of an immunoswitch particle to the subject, wherein:

the immunoswitch particle comprises a nanoparticle comprising:
a first agent that indirectly modulates an immunosuppressive pathway in a tumor cell or immunosuppressive molecule induced by the tumor cell in the tumor microenvironment; and
a second agent that simultaneously targets a co-stimulatory pathway or co-inhibitory pathway in a T cell,
wherein the first agent is a CD73 antagonist antibody or a functional variant thereof that is a CD73 antagonist; and the second agent is a 4-1BB agonist antibody or a functional variant thereof that is a 4-1BB agonist.

7. The method of claim 6, wherein the method extends the length of survival of the subject compared to length of survival of the subject in the absence of administration of the immunoswitch particle.

8. The method of claim 6, wherein the tumor is a melanoma or a colon cancer.

9. The method of claim 6, wherein the subject is a human subject.

10. The method of claim 6, wherein the immunoswitch particle is administered to the subject intratumorally.

11. The method of claim 6, wherein the immunoswitch particle is administered to the subject intravenously.

12. The method of claim 6, wherein administration of the immunoswitch particle reduces or prevents tumor metastasis.

13. The method of claim 6, wherein administration of the immunoswitch particle inhibits the growth of tumor metastases.

14. The method of claim 6, wherein tumor-specific CD8+ T cell activation is increased.

15. The method of claim 6, wherein administration of the immunoswitch particle induces a local immune response.

16. The method of claim 6, wherein administration of the immunoswitch particle induces a systemic immune response.

17. The method of claim 6, wherein administration of the immunoswitch particle induces T cell memory, CD4 cell memory, or CD8 cell memory, or a combination thereof.

18. The method of claim 6, wherein administration of the immunoswitch particle induces T cell memory, inhibits tumor growth, prevents tumor growth, or delays tumor growth.

* * * * *